US010793533B2

(12) United States Patent
Boi et al.

(10) Patent No.: US 10,793,533 B2
(45) Date of Patent: Oct. 6, 2020

(54) DIMERIC CONTRAST AGENTS

(71) Applicant: BRACCO IMAGING S.P.A., Milan (IT)

(72) Inventors: Valeria Boi, Strambino (IT); Roberta Napolitano, Albiano D'Ivrea (IT); Luciano Lattuada, Cassina De'Pecchi (IT); Giovanni Battista Giovenzana, Novara (IT)

(73) Assignee: BRACCO IMAGING S.P.A., Milan (IT)

(*) Notice: Subject to any disclaimer, the term of this patent is extended or adjusted under 35 U.S.C. 154(b) by 0 days.

(21) Appl. No.: 16/468,035

(22) PCT Filed: Dec. 11, 2017

(86) PCT No.: PCT/EP2017/082153
§ 371 (c)(1),
(2) Date: Jun. 10, 2019

(87) PCT Pub. No.: WO2018/108780
PCT Pub. Date: Jun. 21, 2018

(65) Prior Publication Data
US 2020/0017453 A1 Jan. 16, 2020

(30) Foreign Application Priority Data

Dec. 12, 2016 (WO) .................. PCT/EP2016/080621
Jun. 6, 2017 (EP) ...................................... 17174473

(51) Int. Cl.
*C07D 257/02* (2006.01)
*A61K 49/10* (2006.01)
*C07D 403/12* (2006.01)
*A61K 49/12* (2006.01)

(52) U.S. Cl.
CPC .......... *C07D 257/02* (2013.01); *A61K 49/108* (2013.01); *A61K 49/122* (2013.01); *C07D 403/12* (2013.01)

(58) Field of Classification Search
CPC .. C07D 257/02; C07D 403/12; A61K 49/122; A61K 49/108
See application file for complete search history.

(56) References Cited

U.S. PATENT DOCUMENTS

| | | |
|---|---|---|
| 4,647,447 A | 3/1987 | Gries et al. |
| 4,885,363 A | 12/1989 | Tweedle et al. |
| 4,916,246 A | 4/1990 | Felder et al. |
| 5,132,409 A | 7/1992 | Felder et al. |
| 5,277,895 A | 1/1994 | Platzek et al. |
| 5,876,698 A | 3/1999 | Schmitt-Willich et al. |
| 5,980,864 A | 11/1999 | Platzek et al. |
| 6,149,890 A | 11/2000 | Uggeri et al. |
| 7,208,140 B2 | 4/2007 | Schirmer et al. |
| 2011/0177002 A1* | 7/2011 | Zitzmann-Kolbe ......................... A61K 49/0043 424/9.3 |
| 2013/0296539 A1 | 11/2013 | Bhushan |
| 2014/0086846 A1 | 3/2014 | Grimmond et al. |
| 2015/0065711 A1* | 3/2015 | Davis ................. A61K 49/0043 544/363 |
| 2018/0362476 A1 | 12/2018 | Lattuada et al. |
| 2018/0362511 A1 | 12/2018 | Boi et al. |

FOREIGN PATENT DOCUMENTS

| | | | |
|---|---|---|---|
| CN | 102727911 | * 7/2012 | ............. A61K 49/12 |
| DE | 19849465 A1 | 4/2000 | |
| DE | 10117242 C1 | 5/2002 | |
| EP | 0230893 A2 | 8/1987 | |
| EP | 0512661 A1 | 11/1992 | |
| EP | 0872479 A1 | 10/1998 | |
| EP | 1854792 A1 | 11/2007 | |
| EP | 2842940 A1 | 3/2015 | |
| WO | 9509848 A2 | 4/1995 | |
| WO | 9848844 A2 | 11/1998 | |
| WO | 9856775 A1 | 12/1998 | |
| WO | 2006002874 A1 | 1/2006 | |
| WO | 2008126034 A2 | 10/2008 | |
| WO | 2016193748 A1 | 12/2016 | |
| WO | 2017098044 A1 | 6/2017 | |

OTHER PUBLICATIONS

Bechara, G. et al. "Polyazamacrocycles based on a tetraaminoacetate moiety and a (poly)pyridine intracyclic unit: direct synthesis and application to the photosensitization of Eu(III) and Tb(III) ions in aqueous solutions," Tetrahedron 2010 66:8594-8604.
Bordunov et al., "Synthesis of New Pyridinoazacrown Ethers Containing Aromatic and Heteroaromatic Proton Ionizable Substituents" J. Org. Chem. 1995, 60, 6097-6102.
Caravan et al., "Gadolinium (III) Chelates as MRI Contrast Agents: Structure, Dynamics, and Applications," Chem. Rev. 1999, 99, 2293-2352.
Douglass, et al., "Intramolecular Hydrophosphination/Cyclization of Phosphinoalkenes and Phosphinoalkynes Catalyzed by Organolanthanides: Scope, Selectivity, and Mechanism" J. Am. Chem. Soc. 2001, 123, 10221-10238.
Formanovsky, et al., "One Stage Monosubstitution in Cyclen-Two Novel Examples" Synthetic Communications, 1996 26(8), 1595-1603.
Fukase, K. et al "Oligosaccharide Synthesis by Affinity Separation Based on Molecular Recognition between Podand Ether and Ammonium Ion" SYNLETT, 15:2342-2346 (2005).
Fulton D. et al, "Efficient relaxivity enhancement in dendritic gadolinium complexes: effective motional coupling in medium molecular weight conjugates," Chem. Comm. 2005, 474-476.
Gartiser, T. et al. "Reduction d'azides en amines par le formiate d'ammonium par transfert d'hydrogene catalyse (CTH)," Tetrahedron Lett., 24:1609-1610 (1983) (English Abstract).

(Continued)

*Primary Examiner* — Michael G. Hartley
*Assistant Examiner* — Leah H Schlientz
(74) *Attorney, Agent, or Firm* — Vivicar Law, PLLC

(57) ABSTRACT

The present invention relates to new class of dimeric macrocycles capable of chelating paramagnetic metal ions, their chelated complexes with the paramagnetic metal ions and the use thereof as contrast agents, particularly suitable for Magnetic Resonance Imaging (MRI) analysis.

22 Claims, No Drawings

(56) References Cited

OTHER PUBLICATIONS

Geant et al., "Highly Enantioselective Access to α-Dibenzylamino Ketones from Chiral Nonracemic α-Bromo α'-Sulfinyl Ketones by Dynamic Kinetic Resolution: Synthesis of (2R,1'S)-2[1-(Dibenzylamino)alkyl]oxiranes" Eur. J. Org. Chem. 2011, 1300-1309.

Glogard, et al., "Novel radical-responsive MRI contrast agent based on paramagnetic liposomes" Magnetic Resonance in Chemistry 2003, vol. 41, 585-588.

Greene et al. (Eds.), Protective Groups in Organic Synthesis, John Wiley & Sons, Inc., Chapter 5, pp. 152-179 (1981).

Greene et al. (Eds.), Protective Groups in Organic Synthesis, Third Edition, John Wiley & Sons, Inc., Chapter 7, pp. 494-653 (1999).

Hovland et al., "Gadolinium DO3A derivatives mimicking phospholipids; preparation and in vitro evaluation as pH responsive MRI contrast agents" J. Chem. Soc. Perkin Trans. 2, 2001; 929-933.

Maeda et al., "Intramolecular Cyclization of N,N-di(oligooxyethylene)amines: A New Synthesis of Monoaza Crown Ethers" Tetrahedron 1982, vol. 38, No. 22, 3359-3362.

Manning et al., "Expeditious synthesis of 'P'-protected macrocycles en route to lanthanide chelate metal complexes" Tetrahedron Letters 46, (2005) 4707-4710.

Moore, "Selective Trialkylation of Cyclen with tert-Butyl Bromoacetate [1,4,7,10-Tetraazacyclododecane-1,4,7-triacetic acid, Tri-tert-butyl Ester Hydrobromide]" Org. Synth. 2008, 85,10-14.

PCT Search Report and Written Opinion for PCT/EP2016/080592, dated Jan. 23, 2017.

PCT Search Report and Written Opinion for PCT/EP2016/080621, dated Feb. 7, 2017.

PCT Search Report and Written Opinion for PCT/EP2017/082153, dated Mar. 15, 2018.

Pinsker et al., "A Highly Efficient Type I β-Turn Mimetic Simulating an Asx-Pro-Turn-Like Structure." Organic Letters 2011; vol. 13, No. 13: 3502-3505.

Placidi, et al., "Aryl-phosphonate lanthanide complexes and their fluorinated derivatives: investigation of their unusual relaxometric behavior and potential application as dual frequency 1H/19F MRI probes" Chem. Eur. J. 2013, 19, 11644-11660.

Pubchem Entry for 6-bromohexane-1,2,3,4,5-pentol.

Suthagar, K. et al, "Synthesis of arabinose glycosyl sulfamides as potential inhibitors of mycobacterial cell wall biosynthesis," Eur. J. Med. Chem., 102:153-166 (2015).

Tei, et al., "Thermodynamic stability, kinetic inertness, and relaxometric properties of monoamide derivatives of lanthanide(III) DOTA complexes" Dalton Transactions, 2015 vol. 44, 5467-5478.

Wyatt, et al., "An enantioselective synthesis of (R)-2-amino-1-hydroxyethylphosphonic acid by hydrolytic kinetic resolution of (±)-diethyl oxiranephosphonate" Tetrahedron Letters 40 (1999) 6481-6483.

Yuan et al., "Studies on Organophosphorus Compounds 91: A Novel Synthesis of 1-Hydrazinoalkylphosphonic Acids and Derivatives Thereof" 1996, 507-510.

Lee, et al., "Viscosities of Poly(ethylene glycols)," J. Chem. Eng. Data, 35:385-387 (1990).

* cited by examiner

DIMERIC CONTRAST AGENTS

CROSS-REFERENCE TO RELATED APPLICATIONS

This application is the national stage application of corresponding international application number PCT/EP2017/082153, filed Dec. 11, 2017, which claims priority to and the benefit of European application no. 17174473.3, filed Jun. 6, 2017, and international application number PCT/EP2016/080621, filed Dec. 12, 2016, all of which are hereby incorporated by reference in their entirety.

FIELD OF THE INVENTION

The present invention relates to the field of diagnostic imaging and to novel contrast agents possessing improved relaxivity. More in particular, it relates to dimeric macrocycles capable of chelating paramagnetic metal ions, their chelated complexes with metal ions and the use thereof as contrast agents in Magnetic Resonance Imaging (MRI).

STATE OF THE ART

Magnetic Resonance Imaging (MRI) is a renowned diagnostic imaging technique increasingly used in clinical diagnostics for growing number of indications.

The undisputed success of this technique is determined by the advantages it offers, including a superb temporal and spatial resolution, the outstanding capacity of differentiating soft tissues and its safety, due to its non-invasiveness and the absence of any ionizing radiation, in contrast to, for instance, X-ray, PET and SPECT.

In MRI imaging the contrast is basically due to differences existing in the longitudinal T1 and the transverse T2 relaxation times of the water protons in the different body organs and tissues, which allows the in-vivo acquisition of high-resolution, three-dimensional images of the distribution of water.

The intensity of the signal recorded in MRI imaging stems, essentially, from the local value of the longitudinal relaxation rate 1/T1, and the transverse rate, 1/T2 of water protons, and increases with increasing of the 1/T1 value (of the longitudinal relaxation rate of water protons) while decreases with the increase of 1/T2. In other words, the shorter is T1, the higher is the intensity of the recorded signal in MRI, the better is the diagnostic image.

The strong expansion of medical MRI has further benefited from the development of a class of compounds, the MRI contrast agents, that act by causing a dramatic variation of nearby water proton relaxation rates in the tissues/organs/fluids wherein they distributes, thus adding relevant physiological information to the impressive anatomical resolution commonly obtained in the uncontrasted MRI images.

Contrast agents used in the MRI imaging technique typically include a paramagnetic metal ion which is complexed with a cyclic or acyclic chelating ligand, more typically a polyaminopolycarboxylic chelator. The most important class of MRI contrast agents is represented by the Gd(III) chelates which are currently used in about ⅓ of the clinical tests. Indeed, Gd(III) is highly paramagnetic with seven unpaired electrons and a long electronic relaxation time, making it an excellent candidate as a relaxation agent. On the other hand, the free metal ion $[Gd(H_2O)_8]^{3+}$ is extremely toxic for living organism even at low doses (10-20 micromol/Kg). Thus, in order to be considered as a potentially valuable MRI contrast agent, a Gd(III) complex shall display a high thermodynamic (and possibly kinetic) stability in order to prevent the release of toxic metal ion.

Preferred MRI contrast agent should furthermore display optimal relaxivity. Relaxivity ($r_{1p}$, $r_{2p}$), expressed in $mM^{-1}s^{-1}$ and usually measured at 298K and 20 MHz (approx. 0.5 T), is the intrinsic property of a paramagnetic complex which characterizes its capability to increase the nuclear magnetic relaxation rate, longitudinal ($1/T_1$) and transverse ($1/T_2$) respectively, of vicinal water protons and, thus, its efficacy as MRI contrast enhancing agent. In general terms, the higher the relaxivity of an MRI contrast agent, the greater its contrast enhancing capability and the stronger the contrast provided in recorded MRI images.

A number of complexes of paramagnetic metal ions are known in the art (see for instance: Caravan P. et al. *Chem. Rev.* 1999, 99, 2293-2352 and U.S. Pat. Nos. 4,647,447, 4,885,363; 4,916,246; 5,132,409; 6,149,890; and 5,980,864).

Dimeric complexes are disclosed for instance in U.S. Pat. No. 5,277,895, DE10117242, and DE19849465.

Examples of commercially available MRI contrast agents include the complex compound of the $Gd^{3+}$ ion with the DTPA ligand, marketed as MAGNEVIST®; the $Gd^{3+}$ complex of the DTPA-BMA ligand, marketed as OMNISCAN®; the $Gd^{3+}$ complex of BOPTA, known as gadobenate Dimeglumine and marketed as MultiHance™; the $Gd^{3+}$ complex of the DOTA ligand, marketed as DOTAREM®; the $Gd^{3+}$ complex of the hydroxylated tetraaza macrocyclic ligand known as HPDO3A, long time marketed as ProHance®, and that of the corresponding butyl-triol derivative, known as Gadobutrol and marketed ad Gadavist®. All the above contrast agents comprise a single chelating unit, and are Non-Specific Agents (NSA), designed for a general use.

While known compounds generally provide a quality of the imaging capable of meeting and satisfying the present needs of radiologists resulting in accurate and detailed diagnostic information, there is nevertheless still the need for new compounds with improved contrast imaging features, such as increased relaxivity.

In particular, compounds with improved relaxivity could reduce the required dose of the paramagnetic contrast agent and possibly shorten the acquisition time of the imaging process.

SUMMARY OF THE INVENTION

The present invention generally relates to novel macrocyclic chelating ligands useful for the preparation of paramagnetic complexes having particularly favorable characteristics, among others in terms of improved relaxivity.

In general terms, an aspect of the present invention relates to novel dimeric ligands comprising two tetraaza macrocyclic units having a hydroxylated residue on a nitrogen atom of the macrocyclic chelating cage linked to one another through an aminic moiety.

The invention further relates to respective chelated complexes of said chelating ligands with a paramagnetic metal ion and, especially, with $Gd^{3+}$, or of a physiologically acceptable salt thereof.

A further aspect of the invention relates to the use of such chelated complexes as contrast agents, in particular for the diagnostic imaging of a human or animal body organ or tissue by use of the MRI technique.

In a further aspect the invention relates to a manufacturing process for the preparation of the provided ligands, their complex compounds with a paramagnetic metal ion, and the pharmaceutical acceptable salt thereof and their use in the preparation of a diagnostic agent.

According to another aspect, the invention relates to a pharmaceutically acceptable composition comprising at least one paramagnetic complex compound of the invention, or a pharmaceutical salt thereof, in admixture with one or more physiologically acceptable carriers or excipients. Said compositions are useful in particular as MRI contrast media, to provide diagnostically useful images of human or animal body organs or tissues.

Therefore, in another aspect, the present invention refers to a method for the diagnostic imaging of a body organ, tissue or region by use of MRI technique that comprises the use of an effective dose of a compound of the invention.

DETAILED DESCRIPTION OF THE INVENTION

An object of the present invention are chelating ligands of formula (I)

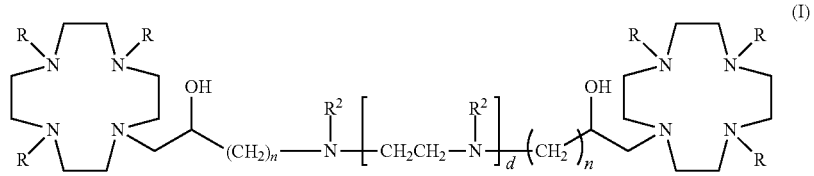

where:
R is —CH($R^1$)—COOH, where:
$R^1$ is H or a $C_1$-$C_3$ alkyl chain that is optionally substituted by a $C_1$-$C_3$ alkoxy or $C_1$-$C_3$ hydroxyalkoxy group;
n is 1 or 2;
d is 0 or 1;
$R^2$ is a $C_1$-$C_5$ alkyl substituted by from 1 to 3 groups X where:
  X is a group of formula —O—[CH($CH_2$O—)$_2$]$_s$($R^3$)$_{s+1}$ or —O—($CH_2CH_2$O—)$_r$—$R^3$, in which:
  $R^3$ is H or a $C_1$-$C_3$ alkyl group, bound to the respective oxygen atom(s) of terminal units —CH($CH_2$O—) or —($CH_2CH_2$O—) of X;
  r is 1, 2, 3, 4, 5, 6, 7 or 8; and
  s is 1, 2 or 3;
with the proviso that when the $C_1$-$C_5$ alkyl in $R^2$ is substituted by a single group X, r and s are not 1.
Preferably in the above compounds of formula (I) $R^1$ is H.

In the present description, and unless otherwise provided, the expression "alkyl" comprises within its meaning any linear or branched hydrocarbon chain derived from the corresponding hydrocarbon by removal of one hydrogen atom, preferably comprising up to 30 carbon atoms. In particular "$C_1$-$C_{30}$ alkyl" comprises within its meaning a linear or branched hydrocarbon chain comprising from 1 to 30 carbon atoms such as: methyl, ethyl, propyl, iso-propyl, butyl, iso-butyl, tert-butyl, pentyl, iso-pentyl, tert-pentyl, hexyl, iso-hexyl, heptyl, iso-heptyl, octyl, and the like. Similarly, the term "$C_1$-$C_3$ alkyl" comprises within its meaning a linear or branched hydrocarbon chain comprising from 1 to 3 carbon atoms such as, for instance, methyl, ethyl, propyl and iso-propyl; the term "$C_1$-$C_5$ alkyl" comprises within its meaning a linear or branched chain comprising from 1 to 5 carbon atoms such as: methyl, ethyl, propyl, iso-propyl, butyl, iso-butyl, tert-butyl, pentyl, iso-pentyl, tert-pentyl, and the like.

The term "hydroxyalkyl" comprises within its meaning any of the above corresponding alkyl moiety wherein one or more hydrogen atoms are replaced by hydroxyl groups. Suitable examples include $C_1$-$C_3$ hydroxyalkyl such as hydroxymethyl (—$CH_2OH$), hydroxyethyl (—$CH_2CH_2OH$), hydroxypropyl (—$CH_2CH_2CH_2OH$), dihydroxypropyl, (—CH($CH_2OH$)$_2$ and —$CH_2$CHOHCH$_2$OH) and the like.

The term "alkoxy" comprises within its meaning an alkyl moiety as above defined further comprising one or more oxygen atoms; examples include, for instance, alkyl-oxy (or -Oalkyl) groups such as methoxy, ethoxy, n-propoxy, iso-propoxy and the like, and alkyl-(poly)oxy in which the alkyl chain is interrupted by one or more, e.g. up to 10, oxygen atoms, for instance including linear alkyl(poly)oxy e.g. of formula —O—($CH_2CH_2$O—)$_r$$R^3$ in which r is an integer from 1 to 8 an $R^3$ is a $C_1$-$C_3$ alkyl e.g. ethyl and, preferably methyl, or a branched alkyl(poly)oxy, e.g. of formula —O—[CH($CH_2$O—)$_2$]$_s$($R^3$)$_{s+1}$ in which s is 1, 2 or 3 and $R^3$ is as above said.

Suitable examples of linear alkyl(poly)oxy for instance include the groups of formula —$OCH_2CH_2OCH_3$, —$OCH_2CH_2OCH_2CH_2OCH_3$, —$OCH_2CH_2OCH_2CH_2OCH_2CH_2OCH_3$, —$OCH_2CH_2OCH_2CH_2OCH_2CH_3$, —$OCH_2CH_2OCH_2CH_3$, —$OCH_2CH_2OCH_2CH_2OCH_2CH_2OCH_2CH_3$, —$OCH_2CH_2OCH_2CH_2OCH_2CH_2OCH_2CH_2OCH_3$, and the like; while examples of branched alkyl(poly)oxy for instance include the groups of formula —OCH($CH_2OCH_3$)$_2$, —OCH($CH_2$OCH($CH_2OCH_3$)$_2$)$_2$, —OCH($CH_2OCH_2CH_3$)$_2$, —OCH($CH_2$OCH($CH_2OCH_2CH_3$)$_2$)$_2$,

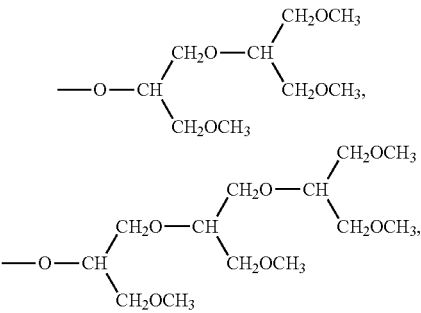

and the like.

The term "hydroxyalkoxy" comprises within its meaning any of the above alkyloxy residues further comprising one or more hydroxyl (—OH) in the alkyl chain. Suitable example for instance include the groups of the above general formulas —O[CH($CH_2$O—)$_2$]$_s$($R^3$)$_{s+1}$ and —O—($CH_2CH_2$O—)$_r$$R^3$ in which $R^3$ is H, such as, for example,

—OCH₂CH₂OCH₂CH₂OH, —OCH(CH₂OH)₂,

—OCH₂CH₂OCH₂CH₂OCH₂CH₂OH,

—OCH₂CH₂OCH₂CH₂OCH₂CH₂OCH₂CH₂OH,

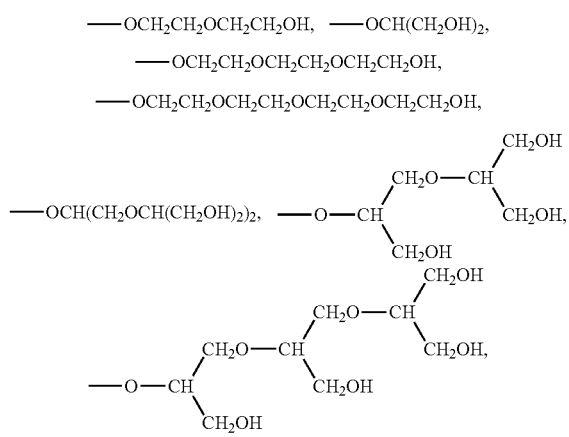

and the like.

In the present description the term "protecting group" designates a protective group adapted for preserving the function of the group to which it is bound. Specifically, protective groups are used to preserve amino, hydroxyl or carboxyl functions. Appropriate carboxyl protective groups may thus include, for example, benzyl, alkyl e.g. tert-butyl or benzyl esters, or other substituents commonly used for the protection of such functions, which are all well known to those skilled in the art [see, for a general reference, T. W. Green and P. G. M. Wuts; *Protective Groups in Organic Synthesis*, Wiley, N.Y. 1999, third edition].

Moreover, the terms "moiety" or "moieties", "residue" or "residues" are herewith intended to define the residual portion of a given molecule once properly attached or conjugated, either directly or through any suitable linker, to the rest of the molecule.

The term "unit(s)", particularly when referred to —[CH(CH₂O—)₂] or —(CH₂CH₂O—), refers to groups of atoms which may be repeated two or more times in a sequence. The term "terminal unit(s)" refers to the unit terminating said sequence.

The compounds of the above formula (I) may have one or more asymmetric carbon atom, otherwise referred to as a chiral carbon atom, and may thus give rise to diastereomers and optical isomers. Unless otherwise provided, the present invention further includes all such possible diastereomers as well as their racemic mixtures, their substantially pure resolved enantiomers, and pharmaceutical acceptable salts thereof.

The present invention further relates to compounds of the above formula (I) in which each of the carboxylic groups R linked to the nitrogen atoms of the tetraaza macrocycles may be in the form of a pharmaceutically acceptable salt, or of a derivative in which the acidic group is suitably protected with an appropriate protecting group (Pg) as above defined, e.g., preferably, of a $C_1$-$C_5$ alkyl ester and, more preferably, of a tert-butyl ester, finding for instance application as such, or as suitable precursor or intermediate compound in the preparation of a desided compound of formula (I) or of a suitable paramagnetic complex or salt thereof.

In one embodiment, the invention relates to dimeric compounds of formula (I) in which d is 0.

Suitable examples include dimers of formula (II)

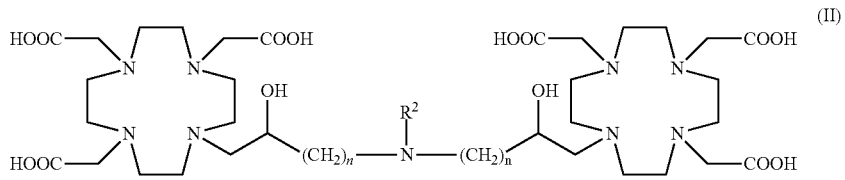

in which:

n is 1 or 2; and $R^2$ is as defined for compounds of formula (I).

In one embodiment, in the above compounds of formula (II) $R^2$ is a $C_1$-$C_5$ alkyl substituted by a single group X.

Suitable examples include dimeric compounds in which $R^2$ is a group of formula —(CH₂)$_p$—X where p is an integer from 1 to 5 and X is a group as said for compounds of formula (I), in which r and s are not 1.

In particular, in one embodiment the invention relates to dimeric compounds of formula (III)

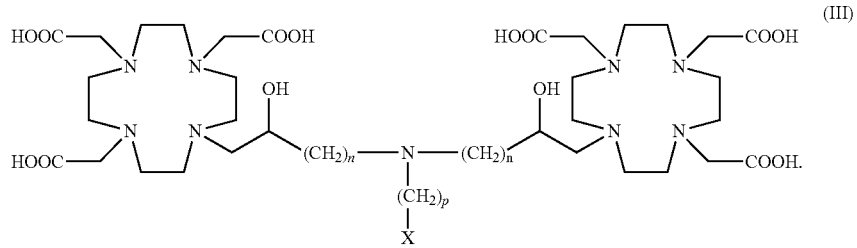

in which n is 1 or 2, and p is an integer from 1 to 5, preferably from 1 to 3.

In one embodiment in the compounds of the above formula (III) X is the group of formula —O—$(CH_2CH_2O—)_rR^3$.

Suitable examples include compounds of formula (III A)

Preferably, in the above compounds of formula (III B), p is 1, 2, or 3, more preferably 1 or 2, and $R^3$ is H or a $C_1$-$C_3$ alkyl, such as ethyl or methyl.

In another embodiment, the invention relates to compounds of formula (II) in which $R^2$ is a $C_1$-$C_5$ alkyl substituted by two or three groups X.

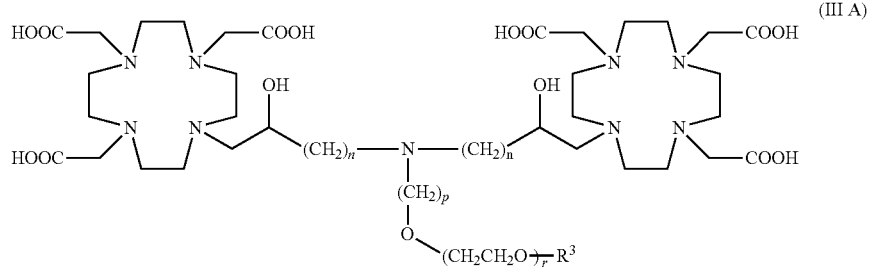

(III A)

in which n and $R^3$ are as defined for compounds of formula (I), p is an integer from 1 to 5, preferably from 1 to 3, and r is an integer from 2 to 8.

Preferably in the above compounds of formula (III A)
n is 1 or 2;
p is 1, 2, or 3, preferably, is 1 or 2 and, most preferably, is 2;
r is an integer from 2 to 8 and, preferably from 2 to 5; and
$R^3$ is H, or a $C_1$-$C_3$ alkyl, such as ethyl or methyl.

More preferably, in the above compounds p is 2; r is from 2 to 5; and $R^3$ is H or methyl.

In a particularly preferred embodiment, the invention relates to dimeric compounds of formula (III A) in which $R^3$ is H, p is 2 and r is from 2 to 4, more preferably 3.

In another embodiment, the invention relates to compounds of formula (III) in which X is a group of formula —O—$[CH(CH_2O—)_2]_s(R^3)_{s+1}$.

Suitable examples include dimeric compounds of formula (III B)

Suitable examples include compounds of formula (II) in which $R^2$ is a linear or branched disubstituted $C_1$-$C_5$ alkyl, e.g. selected from

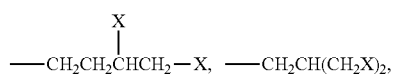

and, preferably, from

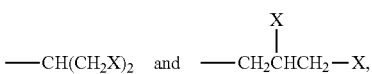

or a linear or branched trisubstituted $C_1$-$C_5$ alkyl, preferably selected from

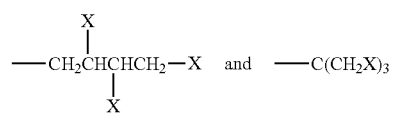

where X is as above said.

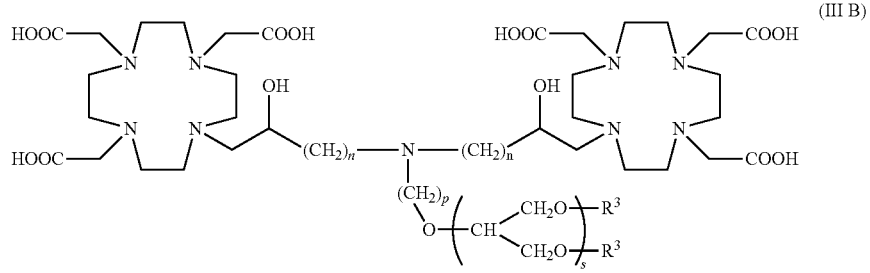

(III B)

in which p is an integer from 1 to 5 and, preferably, from 1 to 3; s is 2 or 3 and, preferably, is 2; and n and $R^3$ are as defined for the compounds of formula (I).

In particular, in another embodiment the invention relates to dimeric compounds comprising two alkoxy or hydroxyalkoxy groups, having the following formula (IV)

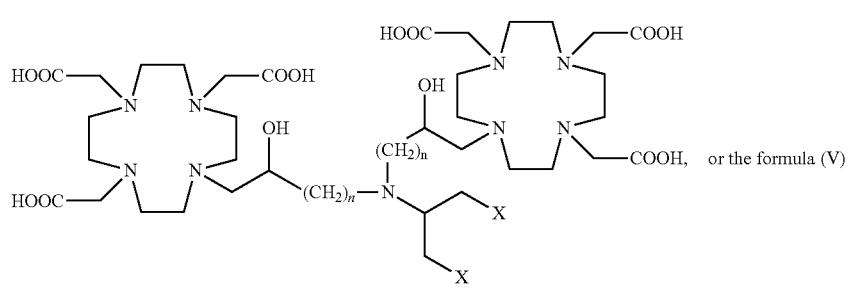
(IV)
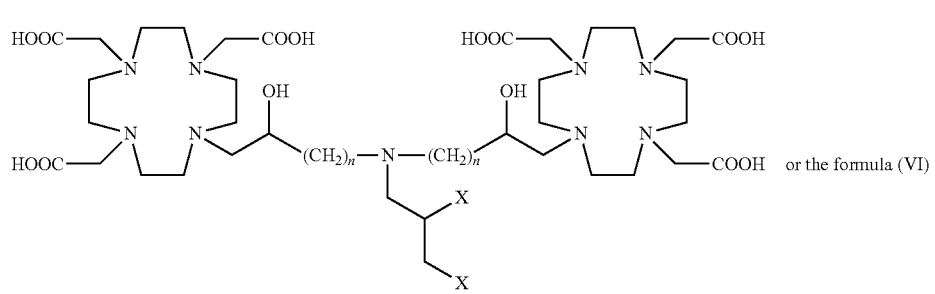
(V)
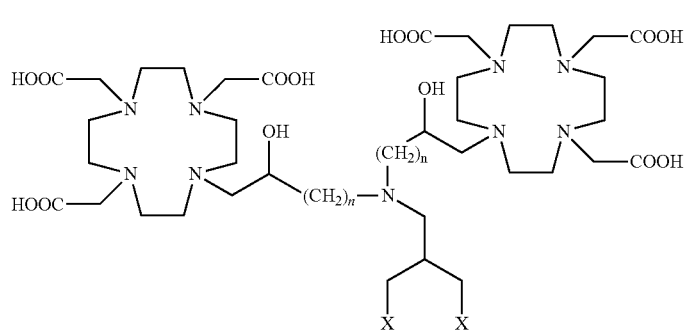
(VI)
in which n is 1 or 2 and X is as said for compounds of formula (I).
In one embodiment, the invention relates to compounds according to the above formulas from (IV) to (VI) in which X is a group of formula —O—$(CH_2CH_2O)_r$—$R^3$.
Preferred among them are compounds of formula (IV A)
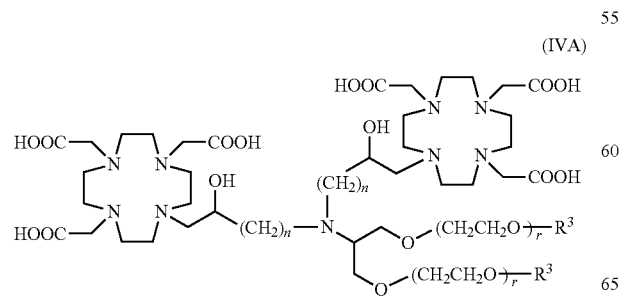
(IVA)

and compounds of formula (V A)

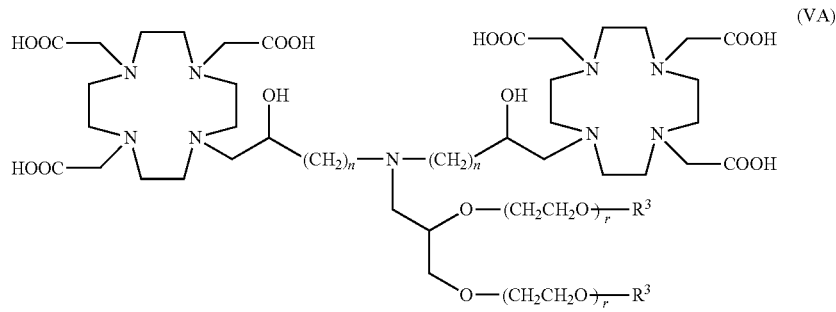

in which:

r is an integer from 1 to 8, preferably from 1 to 5 and, more preferably, is 2, 3 or 4; n is 1 or 2, and $R^3$ is H or a $C_1$-$C_3$ alkyl, such as ethyl or methyl.

In one alternative embodiment, the invention relates to compounds according to the above formulas from (IV) to (VI) in which X is a group of formula —O—[CH(CH$_2$O—)$_2$]$_s$(R$^3$)$_{s+1}$.

Among them, preferred are the compounds of formula (IV B)

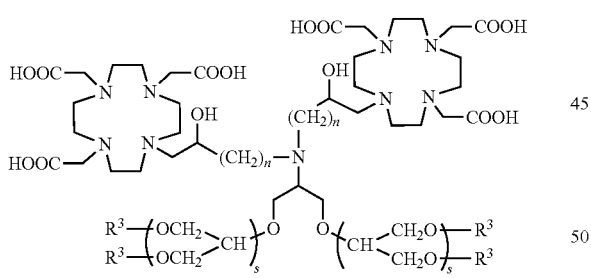

and of formula (VI B)

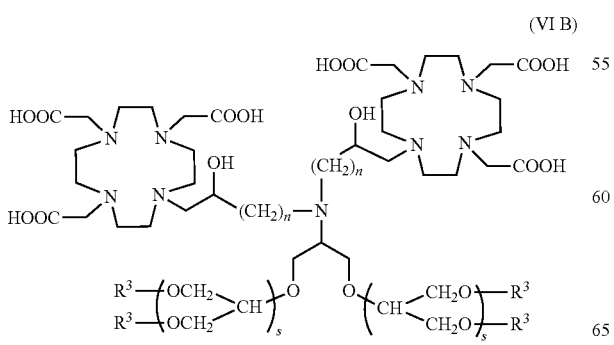

in which n and $R^3$ are as said for compounds of formula 1 and s is 2 or, more preferably, is 1.

In an additional embodiment, the invention relates to dimeric compounds of formula (I) in which d is 1.

Suitable examples include dimers of formula (VII)

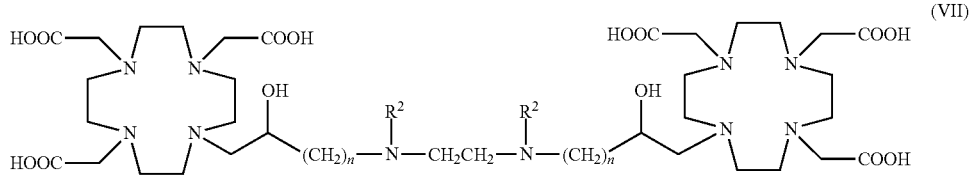

in which the two $R^2$ groups, having the same meaning, are as defined for compounds of formula (I).

Suitable examples include the compounds according to the above formula (VII) in which $R^2$ is as in each of the compounds of formula from (III) to (VI), including the compounds according to each of the corresponding formulas (III A) to (VI A) and (III B) to (VI B).

Preferred among them are the dimeric compounds having the following formula (VIII)

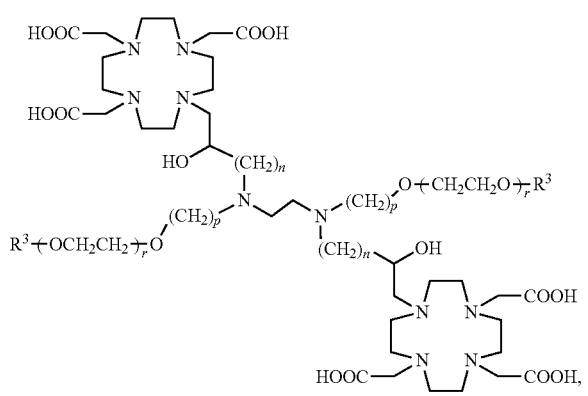

the formula (IX)

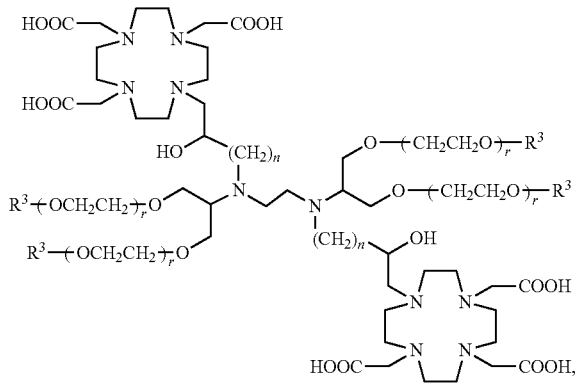

(IX)

and the formula (X)

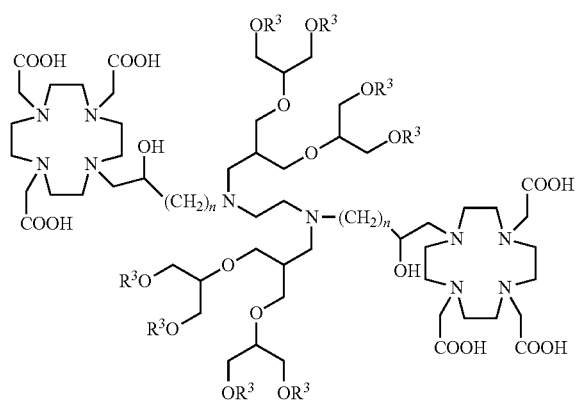

(X)

in which p is an integer from 1 to 5, preferably from 1 to 3, and, most preferably, is 2;

r is an integer from 1 to 8, preferably from 1 to 5 and, more preferably, is 2, 3 or 4; n is 1 or 2, and $R^3$ is H or a $C_1$-$C_3$ alkyl, such as ethyl or methyl.

In one preferred embodiment, in the above compounds of formula (I) hence encompassing those of formulae from (II) to (X), $R^3$ (in $R^2$ or X groups) is a $C_1$-$C_3$ alkyl such as ethyl or, more preferably methyl, and the invention relates to dimeric compounds comprising one or more alkyl(poly)oxy groups of formula —O—($CH_2CH_2O$—)$_r$$CH_3$ in which r is an integer from 1 to 8 and more preferably is 2, 3, 4 or 5, or of formula —O—[CH($CH_2O$—)$_2$]$_s$$CH_3$, in which s is 1 or 2.

In a particularly preferred embodiment, in the above compounds of formula (I), hence encompassing those of formulae from (II) to (X), $R^3$ is H and the invention relates to dimeric compounds comprising one or more hydroxy-alkoxy group(s) of formula —O—($CH_2CH_2O$—)$_r$H in which r is an integer from 1 (or 2) to 8 and more preferably, is 2, 3, 4 or 5, or of formula —O[CH($CH_2O$—)$_2$]$_s$H in which s is 1 or 2.

Most preferably in the compounds of formula (I), hence encompassing those of formulae from (II) to (X), n is 1.

Particularly preferred compounds are those compounds of formula (I), or salts thereof, selected from the group consisting of:

Compound 1

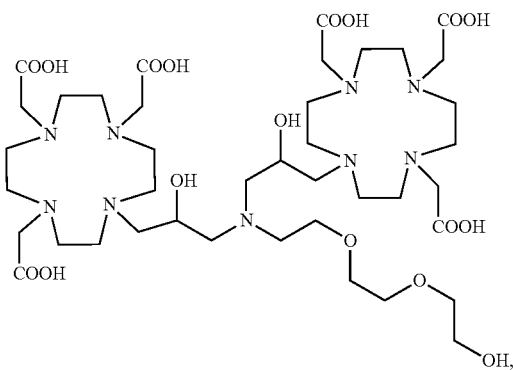

Compound 2

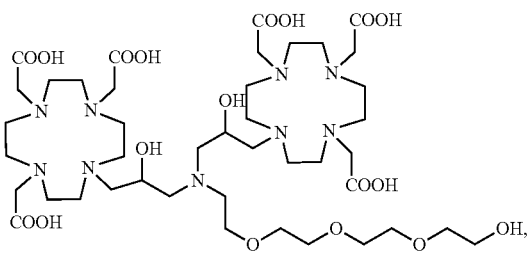

Compound 3

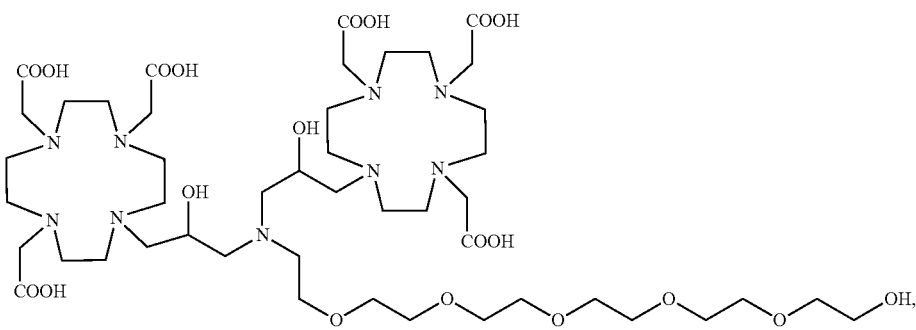

-continued
Compound 4
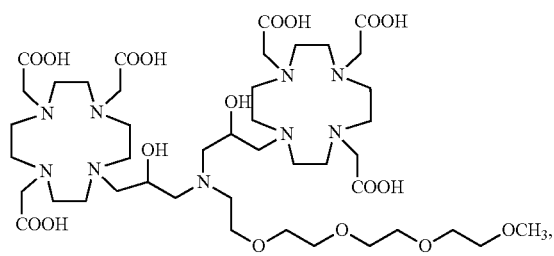
Compound 5
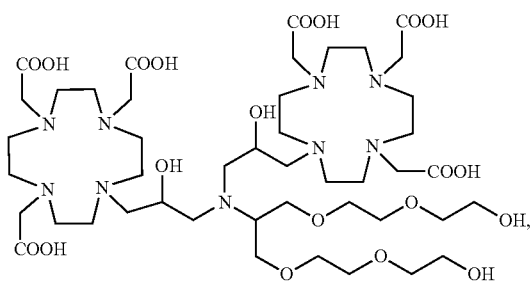
Compound 6
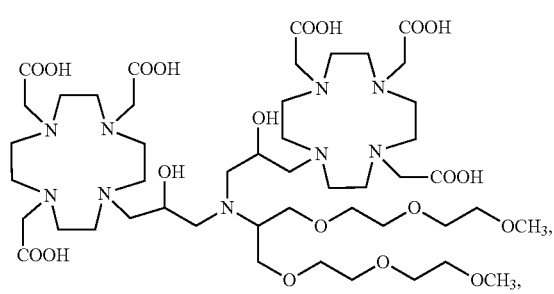
Compound 7
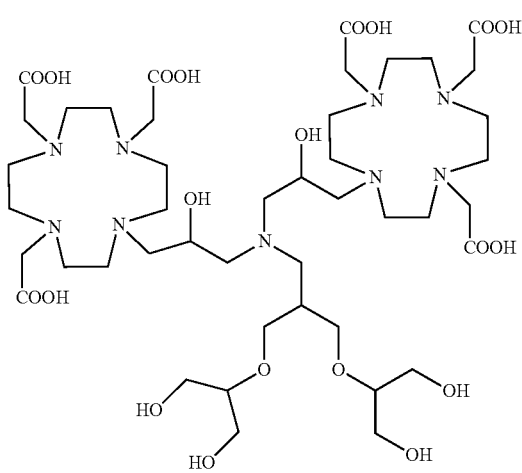
Compound 8
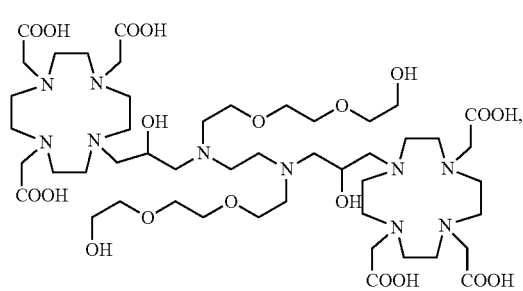
Compound 9
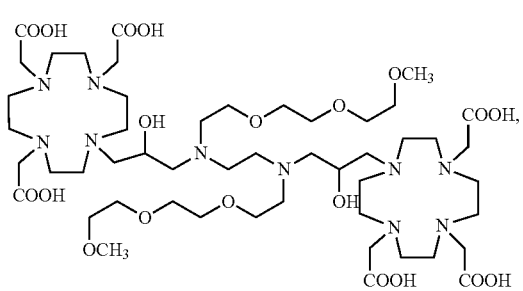
Compound 10
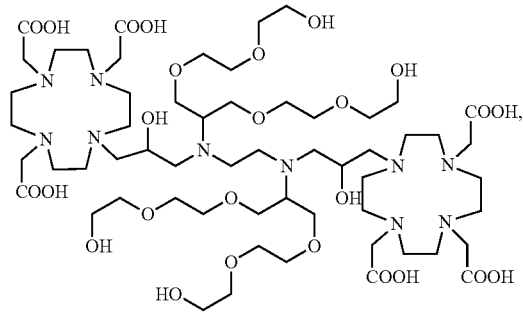
Compound 11
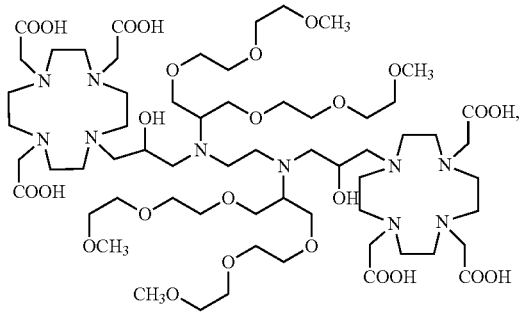

-continued

Compound 12

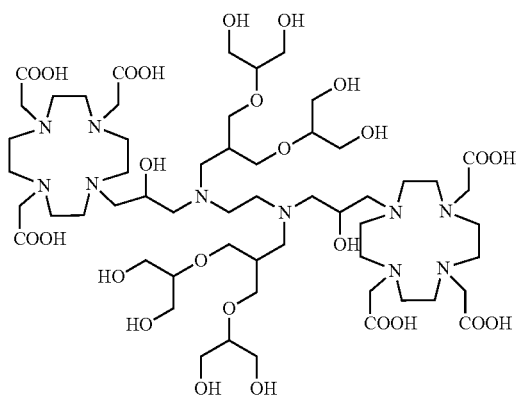

Compound 13

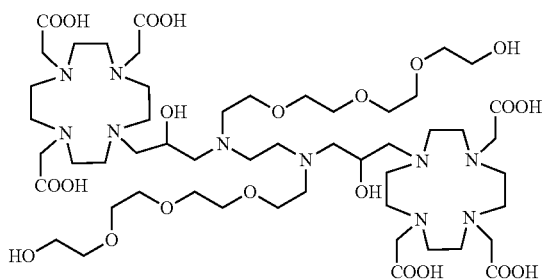

and

In a further aspect the invention relates to chelated complexes of the compounds of formula (I), hence encompassing those of formulae from (II) to (X), with two paramagnetic metal ions, or radionuclides, or of a suitable salt thereof.

Preferably, the paramagnetic metal ions are equal to each other, and are selected in the group consisting of $Fe^{2+}$, $Fe^{3+}$, $Cu^{2+}$, $Cr^{3+}$, $Gd^{3+}$, $Eu^{3+}$, $Dy^{3+}$, $La^{3+}$, $Yb^{3+}$ or $Mn^{2+}$. More preferably, both the chelated paramagnetic metal ions are $Gd^{3+}$ ions.

Preferred radionuclides according to the invention providing complexes for use in radiotherapy or radiodiagnostics include $^{105}Rh$, $^{117m}Sn$, $^{99m}Tc$, $^{94m}Tc$, $^{203}Pb$, $^{67}Ga$, $^{68}Ga$, $^{44}Sc$, $^{72}As$, $^{110}In$, $^{111}In$, $^{113}In$, $^{90}Y$, $^{97}Ru$, $^{60}Cu$, $^{62}Cu$, $^{64}Cu$, $^{52}Fe$, $^{51}Mn$, $^{140}La$, $^{175}Yb$, $^{153}Sm$, $^{166}Ho$, $^{149}Pm$, $^{177}Lu$, $^{186/188}Re$, $^{165}Dy$, $^{166}Dy$, $^{142}Pr$, $^{159}Gd$, $^{211}Bi$, $^{212}Bi$, $^{213}Bi$, $^{214}Bi$, $^{149}Pm$, $^{67}Cu$, $^{198}Au$, $^{199}Au$, $^{161}Tb$, $^{167}Tm$, and $^{51}Cr$.

The compounds of formula (I) of the invention, and encompassed formulae from (II) to (X), and paramagnetic chelates thereof with bivalent paramagnetic metal ion(s), can also be in the form of a pharmaceutically acceptable salt, particularly as an addition salt with a physiologically compatible base or acid.

The term "pharmaceutically acceptable salt", as used herein, refers to derivatives of the compounds of the invention wherein the parent compound is suitably modified by converting any of the free acid or basic groups, if present, into the corresponding addition salt with any base or acid conventionally intended as being pharmaceutically acceptable.

Preferred cations of inorganic bases which can be suitably used to prepare a salt of the complexes or the ligands of the invention comprise, for instance, ions of alkali or alkaline-earth metals such as potassium, sodium, calcium or magnesium.

Preferred cations of organic bases comprise, for instance, those of primary, secondary and tertiary amines such as, for instance, ethanolamine, diethanolamine, morpholine, glucamine, N-methylglucamine, N,N-dimethylglucamine.

Preferred anions of inorganic acids which can be suitably used to prepare salts of the complexes of the invention comprise the ions of halo acids, for instance chlorides, bromides or iodides, as well as of other suitable ions such as sulfate.

Preferred anions of organic acids comprise those routinely used in pharmaceutical techniques for the preparation of salts of basic substances such as, for instance, acetate, succinate, citrate, fumarate, maleate or oxalate.

Preferred cations and anions of amino acids comprise, for instance, those of taurine, glycine, lysine, arginine, ornithine or of aspartic and glutamic acids.

The preparation of the compounds of formula (I), hence encompassing the compounds of formulae from (II) to (X), and of the chelate complexes thereof, either as such or in the form of physiologically acceptable salts, represent a further object of the invention.

Compounds of formula (I), and the chelated complexes thereof, may be prepared through a general synthetic process comprising the following steps:

a) Obtaining a macrocyclic substrate 1 in a suitable protected form, e.g. in which the carboxylic groups of the substrate are protected as tert-butyl esters;

b) Obtaining a bridging molecule 2, in which any optional functional group(s) not involved with the coupling reaction with the substrate 1 is, optionally, suitably protected;

c) Coupling the bridging molecule 2 with two units of protected substrate 1, to give the desired compound of formula (I) in a suitably protected form or, alternatively, an intermediate thereof 3;

d) Optionally converting the obtained intermediate in the suitably protected compound of formula (I);

e) Removing any protecting group and isolating the chelating ligand of formula (I); and f) Complexing the obtained ligand with a suitable paramagnetic metal ion and isolating the chelate complex, or the salt thereof.

To this extent, and unless otherwise indicated, the term "intermediate" (e.g. with reference to the compound 3 deriving from the reaction of two units of macrocyclic substrate 1 with a bridging molecule 2) refers to a molecule that requires one (or more) further reactions, e.g. deprotection/alkylation reaction(s) converting any optional protected nitrogen atom(s) of the bridging molecule 2 in the corresponding alkylated derivative(s), to give the desired product, i.e. in the specific case of the above general scheme, a suitably protected dimeric compound of formula (I) according to step d). The single steps of the above general process, comprehensive of any variant thereof, particularly when referring to the steps of protection/deprotection and activation of known functional groups, may be carried out according to conventional methods known in the art.

For instance, suitable substrates 1A according to the step a) of the process of the invention, of formula

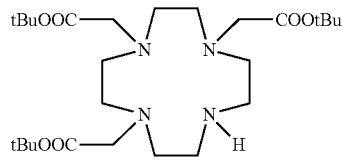

in which all carboxyl groups are suitably protected as tert-butyl esters, may be obtained e.g. as disclosed in *Org. Synth.* 2008, 85, 10.

Appropriate bridging molecules 2 for the use of the invention are commercially available, or may easily be prepared according to procedures known to those skilled in the relevant art. Suitable examples may for instance comprises an amine of formula $NH_2R^2$ or diamine of formula $NH(R^2)-CH_2CH_2-NH(R^2)$ in which $R^2$ is as defined for compounds of formula (I), or suitable functional derivative thereof, or precursor thereof, e.g. having a protecting group Pg on the nitrogen atom(s) in the place of $R^2$, that are commercially available or may be easily obtained according to synthetic procedure known to those skilled in the relevant art.

Examples of specific procedures for the preparation of protected bridging molecules 2, their coupling with the appropriate substrate molecule 1, and optional conversion of the obtained intermediates in the desired compound of formula (I) are provided in the experimental section, together with relevant operational details.

As a general reference on possible protecting groups, and cleavage conditions, e.g. to implement the step e) of the above general synthetic procedure, see the above cited "T. W. Green and P. G. M. Wuts; Protective groups in organic synthesis" Wiley 3$^{rd}$ Ed. Chapters 5 and 7.

The complexation of the compounds of formula (I) e.g. obtained from step f) of former general preparation scheme with a paramagnetic ion and, particularly, with gadolinium, may be performed, for instance, by stoichiometric addition of a suitable Gd(III) derivative, particularly a Gd(III) salt or oxide, to a solution of the ligand, e.g. by working according to well-known experimental methods, for instance as reported in EP 230893.

Optional salification of the chelating ligands of the invention, or of chelates with bivalent metal ions, may be carried out by properly converting any of the free acidic groups into the corresponding pharmaceutically acceptable salts. In this case too, the operative conditions being employed for the optional salification of the compounds of the invention are all within the ordinary knowledge of the skilled person.

Exemplificative implementation of the above general procedure leading to the compounds of the formula (I) and of the chelate complexes thereof, are schematized herein below.

For instance, dimeric compounds according to the invention may conveniently be prepared by using the synthetic procedure schematized in the following general Scheme 1

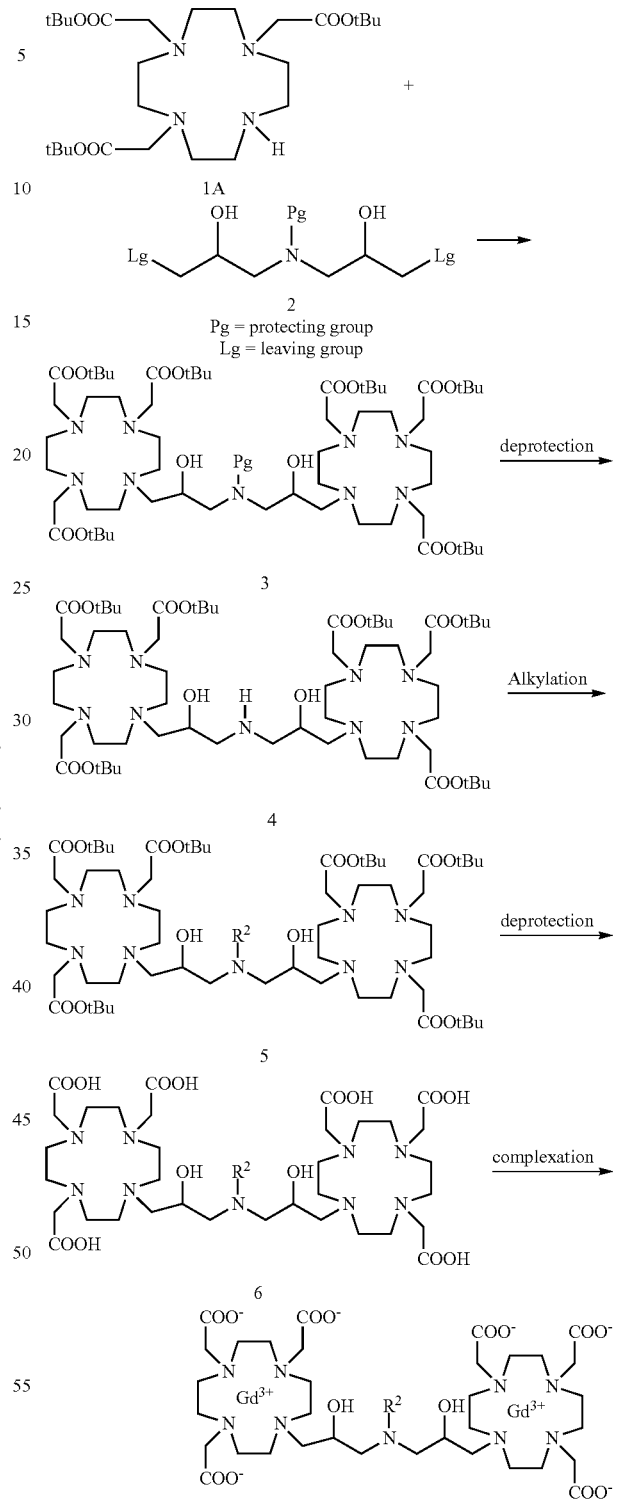

in which the bridging molecule 2 is reacted with two units of substrate 1A to give an intermediate 3 in which the nitrogen atom (of the bridging moiety) is in a protected form, which is first deprotected and then alkylated with the appropriate $R^2$ group to give the protected dimer of formula (II) that after cleavage of carboxyl-protecting groups is complexed with the gadolinium metal ion to give the desired bis-Gd complex of formula (II).

Dimeric compounds according to the formula (II) may alternatively be prepared by using the synthetic procedure schematized in the following Scheme 2

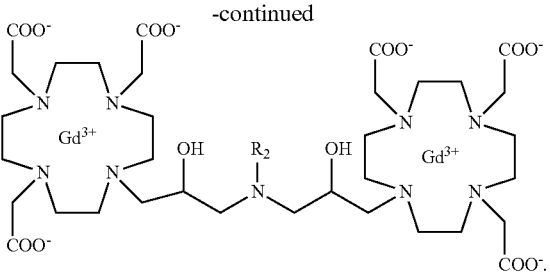

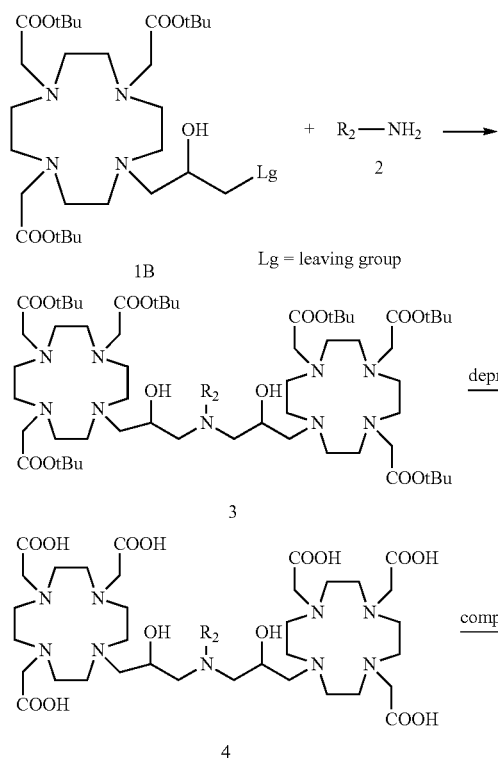

According to this approach, a suitably protected Substrate 1B

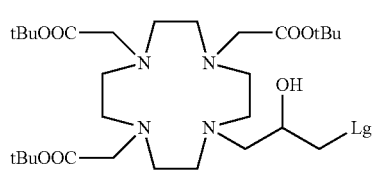

in which Lg represents a leaving group such as OMs, OTs, Br, I and, preferably, Cl is first obtained, e.g. by reaction of the commercially available epichlorydrin with the substrate 1A, as described in details in the experimental section, which is then reacted with the appropriated amine $R^2$—$NH_2$ leading to the compound of formula 3 having protected carboxyls groups, that is then deprotected and complexed as above said.

Compounds of formula (VII) comprising a bridging molecule with two nitrogen atoms may be analogously obtained by using the appropriate bis-aminic molecule 2 e.g. of formula $NH(R^2)$—$CH_2CH_2$—$NH(R^2)$ or a corresponding bridging molecule in which the two nitrogen atoms are in a protected form, e.g. according to the synthetic procedure schematized in the following Scheme 3.

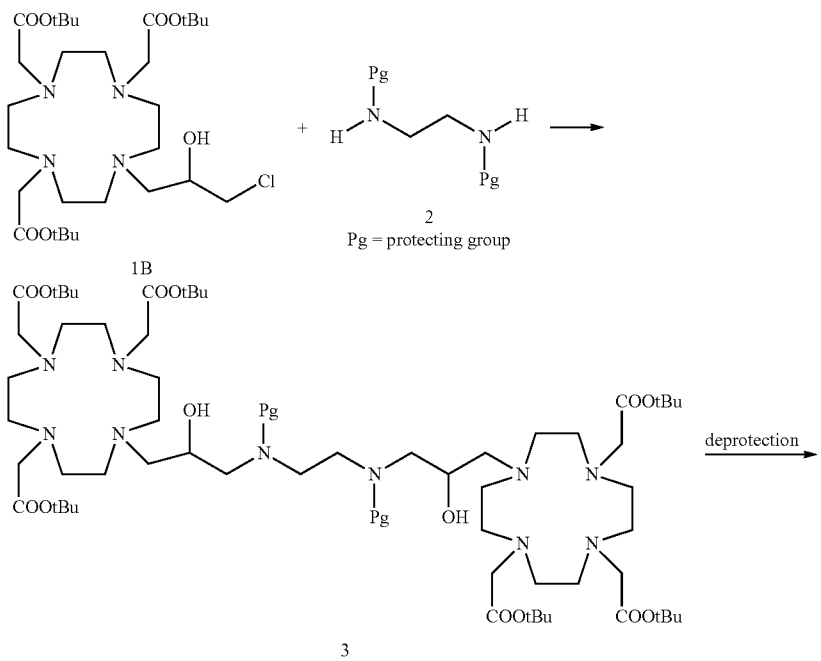

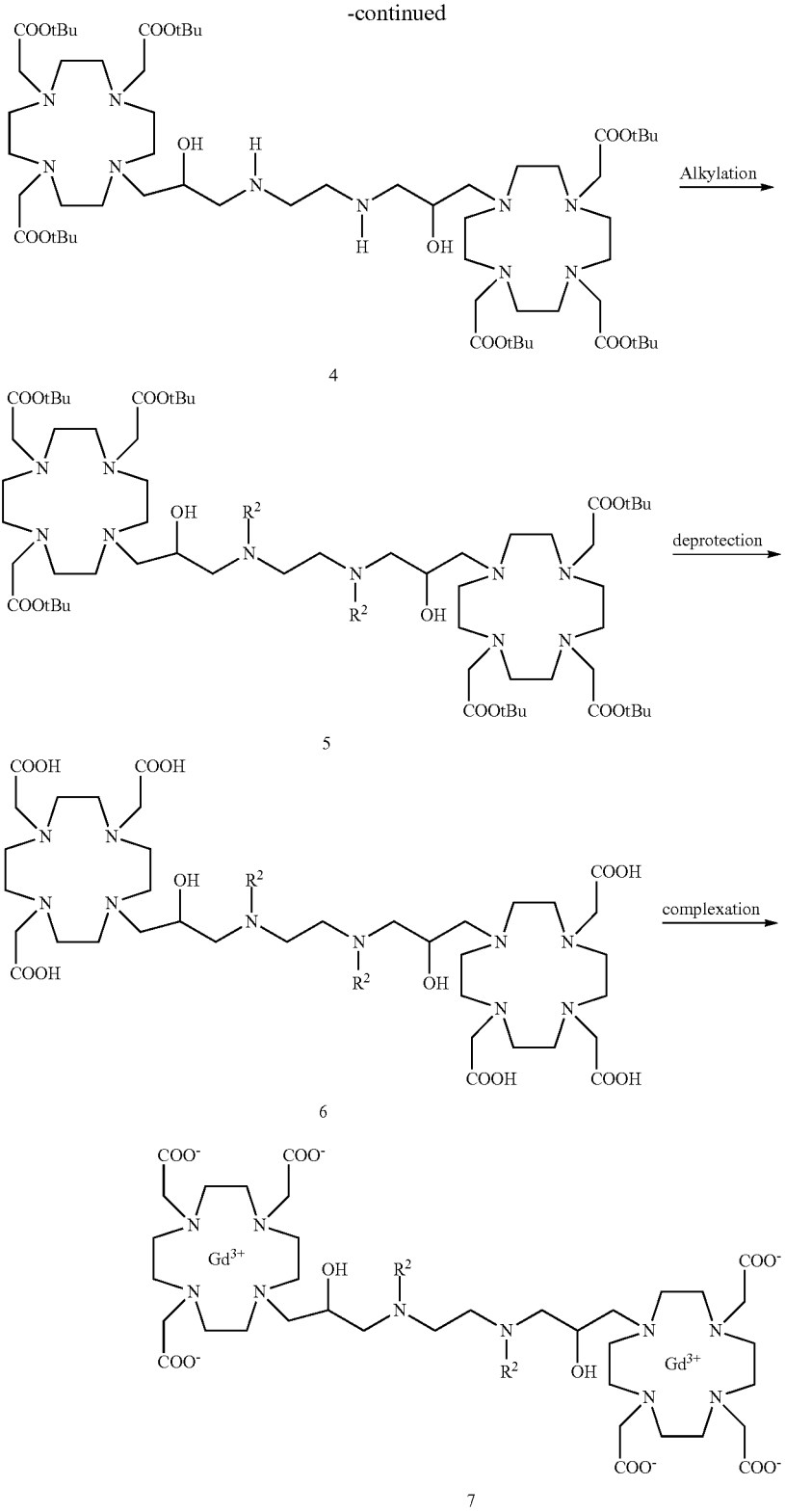

Specific examples of preparation of preferred compounds of formula (I) according to the invention are moreover provided in the following experimental section, constituting a general reference to the operative conditions being employed in the above processes.

Dimers of formula (I) according to the present invention include two tetraaza macrocycles each having a hydroxylated arm on a nitrogen atom of the macrocyclic cage, linking them to each other by means of an aminic moiety comprising one or two —N($R^2$)— group(s).

Dimeric paramagnetic complexes according to the invention, having these peculiar structural components have proved to display high relaxivity and stability.

Relaxivity $r_{1p}$ values measured for some representative complex compounds of formula (I) are provided in Table A of the experimental section, by comparison with $r_{1p}$ values measured, at the same conditions, for some known MRI contrast agents currently used in the diagnostic daily practice, e.g. including Gd-DOTA, marketed as DOTAREM®, and Gd-HPDO3A marketed as ProHance®. By definition, relaxivity data, hence including those of the table A, are expressed in terms of gadolinium concentration (mM).

Interestingly, relaxivity $r_{1p}$ values measured for the dimeric complex compounds of the invention are at least to 2 times higher than that recorded for commercial contrast agent of the market (at the same gadolinium concentration).

In particular, the paramagnetic complex compounds of the formula (I) of the invention display a relaxivity $r_{1p}$ value measured in human plasma, at 37° C. and approx. 1.4 T, which is of at least about 8, preferably higher than 9, and more preferably, higher than 10 mM$^{-1}$s$^{-1}$-(normalized, as said, to the gadolinium).

Moreover, the paramagnetic complex compounds of the invention have proven to display a low if not negligible protein binding with human plasma proteins, including, for instance, the HSA.

In addition, the Applicant has observed that the presence of a hydroxylated pendant arm on each macrocyclic cage of the dimeric compounds of the invention, besides leading to complex compounds having favorable relaxivity and solubility, may also contribute to obtain aqueous solutions of corresponding complex paramagnetic endowed with optimized viscosity.

Advantageously, the high relaxivity displayed by the agents of the invention may allow to reduce their diagnostically effective dose, as compared to current contrast agents. Paramagnetic complexes and, especially, gadolinium complexes of the compounds of formula (I), or the pharmaceutical acceptable salt thereof, thus find advantageous use in the preparation of pharmaceutical formulations intended for a general use in the diagnostic imaging of a human or animal body organ, tissue or region either in vivo or in vitro, ex vivo.

According to a further aspect, the invention relates to the use of the compounds of formula (I) in the form of complexes with a paramagnetic metal ion and, especially, gadolinium, for the preparation of a pharmaceutical formulation for use in the diagnostic imaging, either in vivo or in vitro, ex vivo, of a human or animal body organ, tissue or region or of a biological sample, including cells, biological fluids and biological tissues originating from a live mammal patient, and preferably, human patient, by use of the MRI technique.

A further aspect of the invention concerns a pharmaceutical composition for diagnostic use comprising a compound of formula (I) in the form of paramagnetic metal complex or, when appropriate, (i.e. when the complex is with a bivalent paramagnetic metal ion), of a pharmaceutical salt thereof, in admixture with one or more physiologically acceptable excipients, diluents or solvents. Preferably, the pharmaceutical composition is a contrast-producing composition and, more preferably, a MRI contrast producing composition comprising at least one Gd-complex according to the invention.

In an additional aspect the invention relates to a MRI contrast medium comprising an effective amount of at least one chelated compound according to the invention and, especially, of a gadolinium complex of the formula (I) in combination with one or more pharmaceutically acceptable excipients, diluents or solvents.

To this extent, and unless otherwise provided, the term "effective amount" or "effective dose", as used herein, refers to any amount of a paramagnetic chelated complex of the formula (I) according to the invention or pharmaceutical composition thereof, that is sufficient to fulfil its intended diagnostic purpose(s): i.e., for example, to ex vivo visualize a biological element including cells, biological fluids and biological tissues, or for the in vivo diagnostic imaging of body organs, tissues or regions of a patient.

Unless otherwise indicated, with "individual patient" or "patient" as used herein we refer to a living human or animal patient, and, preferably a human being undergoing MR diagnostic assessment.

Details concerning dosages, dosage forms, modes of administration, pharmaceutically acceptable carriers, excipients, diluents, adjuvants and the like are known in the art.

Interestingly, and as above discussed, suitable dosage of the paramagnetic complexes according to the invention, i.e. allowing to obtain a diagnostically effective visualization of the body organ, tissue or region at least comparable to that obtained in the daily practice with the MRI contrast agents of the market, may include an amount of the paramagnetic complex lower than that currently used with Non-Specific contrast agents of the market.

For instance, satisfactory diagnostic MRI images, providing a physician with adequate diagnostic support, may be obtained with doses of the gadolinium complex compounds identified by the present invention of about 80%, more preferably 70%, and up to 50% of the dose of MRI contrast agent used in the daily practice, which for adult patients commonly is of about 0.1 mmol/kg of patient body weight.

From all the foregoing it can be easily envisaged that the selection of paramagnetic complex compounds of formula (I) identified by the present invention have a wide range of applications as they can be used for intravasal, (for instance intravenous, intraarterial, intracoronaric, intraventricular administration and the like), intrathecal, intraperitoneal, intralymphatic and intracavital administrations. Furthermore, they are suitable for the oral or parenteral administration and, therefore, specifically for the imaging of the gastrointestinal tract.

For instance, for parenteral administration they can be preferably formulated as sterile aqueous solutions or suspensions, whose pH can range from 6.0 to 8.5.

These formulations can be lyophilized and supplied as they are, to be reconstituted before use.

For the gastrointestinal use or for injection in the body cavities, these agents can be formulated as a solution or suspension optionally containing suitable excipients in order, for example, to control viscosity.

For the oral administration they can be formulated according to preparation methods routinely used in the pharmaceutical technique or as coated formulations to gain additional protection against the stomach acidic pH thus preventing, in case of chelated metal ions, their release which may take place particularly at the typical pH values of gastric fluids.

Other excipients, for example including sweeteners and/or flavouring agents, can also be added, according to known techniques of pharmaceutical formulations.

The solutions or suspensions of the compounds of this invention can also be formulated as aerosol to be used in aerosol-bronchography and instillation.

For example, they can be also encapsulated into liposomes or even constitute the liposomes themselves, as set forth above, and thus can be used as uni- or multi-lamellar vesicles.

In a preferred aspect, pharmaceutical compositions according to the invention are properly formulated in isotonic sterile aqueous, optionally buffered, solutions for parenteral administration, and most preferably for intravenous or intra-arterial administration.

More preferably, the said diagnostic composition has a concentration of the paramagnetic complex of the formula (I) of from 0.002 and 1.0 M and is supplied, for instance as a bolus, or as two or more doses separated in time, or as a constant or non-linear flow infusion.

In a further aspect, the invention relates to the use of a pharmaceutical composition including a paramagnetic chelated complex of the formula (I) or, when appropriate, a pharmaceutical acceptable salt thereof, for the diagnostic imaging, both in vitro (ex vivo) and in vivo, of pathological systems, including cells, biological fluids and biological tissues originating from a live mammal patient, and preferably, human patient, as well as of human body organ, regions or tissues, including tumors or cancerous tissues, inflammations, as well as for monitoring the progress and results of therapeutic treatment of the said pathologies.

In an additional aspect, the present invention concerns a method for the in vivo imaging of a body organ, tissue or region by use of the MRI technique, said method comprises enhancing the signal generated by the water protons by use of a paramagnetic chelated complex of the formula (I) according to the invention, or (when appropriate) a physiological acceptable salt thereof.

In one embodiment, said method comprises administering to a human or animal patient to be imaged a diagnostically effective amount of a composition of the invention comprising a compound of formula (I) in the form of complex with a paramagnetic metal ion, and, preferably, with the $Gd^{3+}$ metal ion and then subjecting the administered patient to the diagnostic imaging by use of the MRI technique.

According to a particularly preferred embodiment, the above MRI method is instead performed on human or animal bodies suitably pre-administered with a diagnostically effective amount of a composition of the invention as above defined.

More particularly, according to a preferred embodiment the present invention refers to a method for the in vivo imaging a human or animal body organ or tissue by use of the MRI technique that comprises the steps of:

a) submitting a human or animal pre-administered with a composition of the invention comprising a compound of formula (I) in the form of a paramagnetic complex, or of a pharmaceutically acceptable salt thereof, and positioned in a MRI imaging system, to a radiation frequency selected to excite the non-zero proton spin nuclei of the active paramagnetic substrate; and b) recording a MR signal from said excited nuclei.

In yet another aspect the invention provides a method for the in vitro (ex vivo) imaging of biological samples, including cells, biological fluids and biological tissues originating from a live mammal patient, and preferably, human patient, by use of the MRI technique, that comprises contacting an effective amount of a paramagnetic complex compound of formula (I), or of a physiologically acceptable salt thereof, with the biological sample of interest and then obtaining MRI signals from said samples by use of the MRI technique.

Non-limiting examples of preferred compounds of the invention and intermediates for their preparation is reported in the following section, aimed to illustrate the invention in greater detail without limiting its scope.

EXPERIMENTAL PART

Example 1: Preparation of the Substrate 1B

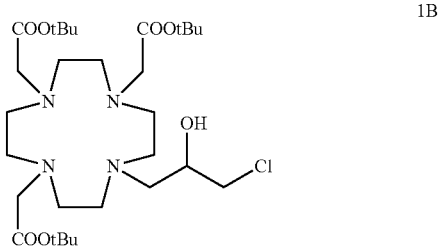

This compound was obtained by using the synthetic procedure shown in Scheme 4

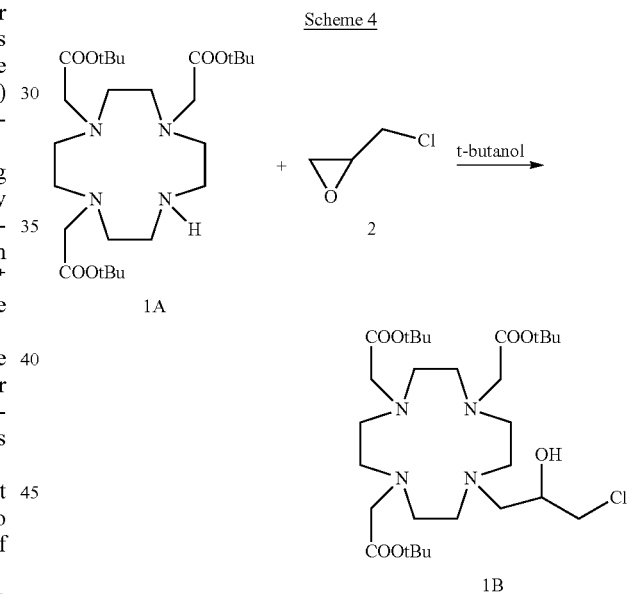

comprising:

a) Preparation of Compound 1B.

Commercially available epichlorohydrin 2 (10.5 mL; 137 mmol) was dissolved in acetonitrile (300 mL) and the resulting solution was slowly added at room temperature to a solution of DO3A tris-t-butyl ester 1A (prepared e.g. as disclosed in Org. Synth. 2008, 85, 10) (14.1 g; 27.4 mmol) in acetonitrile (100 mL). The mixture was stirred for 24 h, then further epichloridrin 2 (5.2 mL; 68 mmol) was added. After additional 24 h the mixture was evaporated and the residue purified by chromatography on silica gel (eluent: $CH_2Cl_2$/MeOH=50:1→1:1) to give compound 1C (10.6 g). Yield 64%.

1H-NMR, 13C-NMR and mass spectrum were consistent with the expected structure.

Example 2: Preparation of the Chelate Complex 1
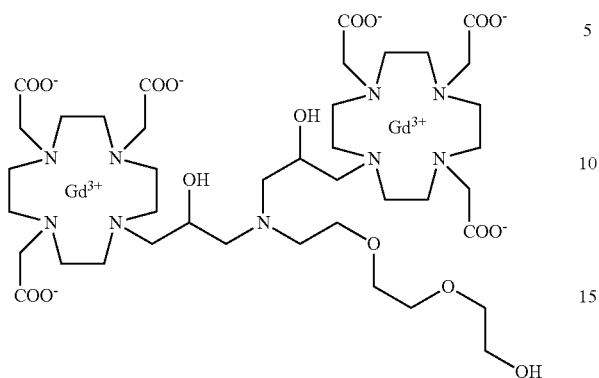
This compound was obtained by using the procedure shown in Scheme 5:
Scheme 5
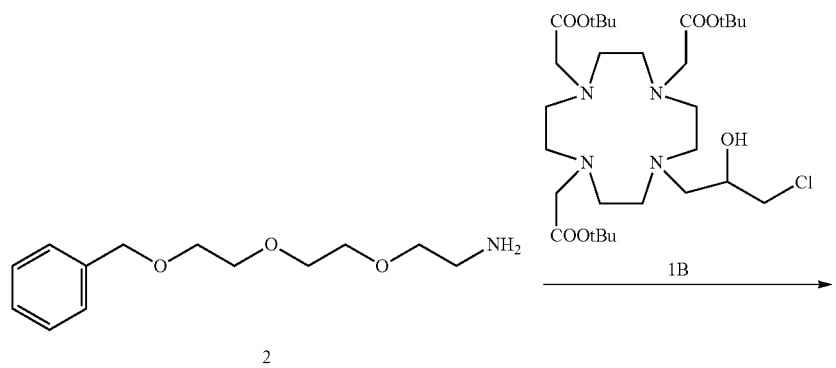
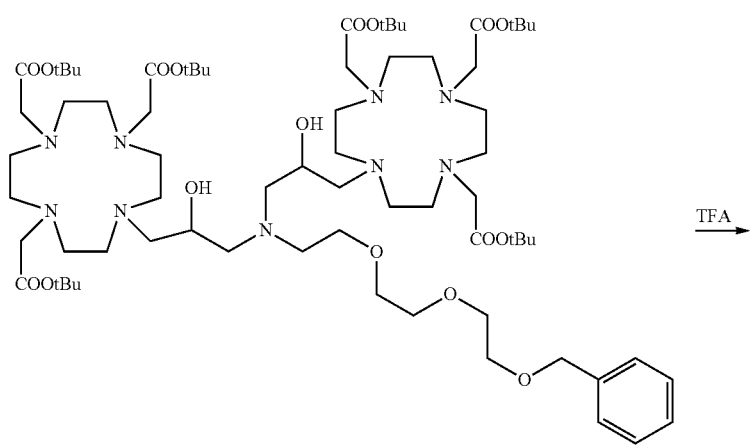

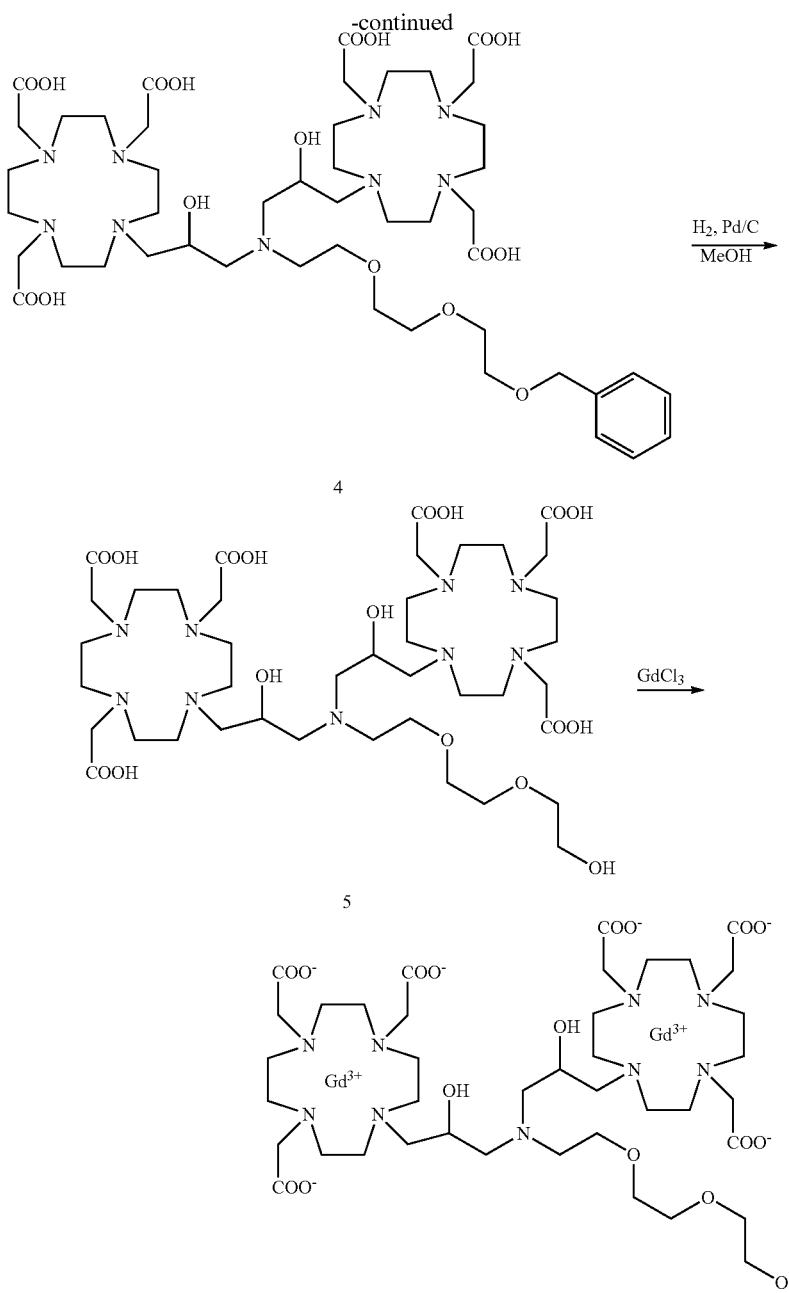

including:

a) Preparation of 3

A mixture of amine 2 (prepared for instance as disclosed in *Eur. J. Med. Chem.* 2015, 102, 153) (6 g; 25 mmol), compound 1B (30.4 g; 50 mmol) and Et$_3$N (10 mL) in acetonitrile (300 mL) was stirred at room temperature for 72 h then evaporated. The residue was purified by flash chromatography on silica gel (eluent: CH$_2$Cl$_2$/MeOH=100:1→1:1) to give compound 3 (18 g). Yield 52%.

1H-NMR, 13C-NMR and mass spectrum were consistent with the expected structure.

b) Preparation of 4

Trifluoroacetic acid (10 mL) was added to a solution of intermediate 3 (15.2 g; 11 mmol) in dichloromethane (100 mL). The mixture stirred for 30 min then was evaporated.

The residue was dissolved in TFA (50 mL) and triisopropylsilane (0.2 mL) was added. The obtained mixture was stirred for 24 h at room temperature, then evaporated and the residue purified by chromatography on Amberlite XE 750 column (eluent: gradient of water/MeCN) obtaining compound 4 (9.2 g). Yield 80%.

1H-NMR, 13C-NMR and mass spectrum were consistent with the expected structure.

c) Preparation of 5

A solution of intermediate 4 (10.5 g; 10 mmol) in methanol (200 mL) was added with 5% palladium on carbon (wet with about 50% water) (1.5 g) and hydrogenated at room temperature for 24 h. The catalyst was filtered and the solution evaporated to give ligand 5 (9.3 g). Yield 97%.

1H-NMR, 13C-NMR and mass spectrum were consistent with the expected structure.

d) Complexation

Ligand 5 (5 g; 5.2 mmol) was dissolved in water (100 mL), gadolinium chloride hexahydrate (3.87 g; 10.4 mmol) was added then 1M NaOH was added to achieve pH 7. The mixture was stirred at 50° C. for 18 h. The solution was then filtered on Millipore HA 0.25 μm filters and evaporated under reduced pressure. The crude product was purified on Amberchrome CG161M column (eluent: gradient of water/acetonitrile). The fractions containing the pure product were pooled and evaporated. The solid product was dried under vacuum to obtain the gadolinium complex as a white powder (5.2 g). Yield 79%.

1H-NMR, 13C-NMR and mass spectrum were consistent with the expected structure.

Example 3: Preparation of the Chelate Complex 2

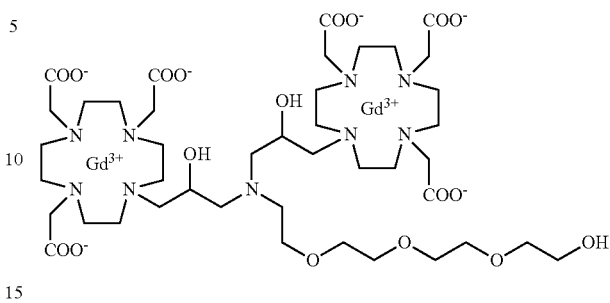

This complex compound was obtained by using the procedure shown in Scheme 6:

Scheme 6

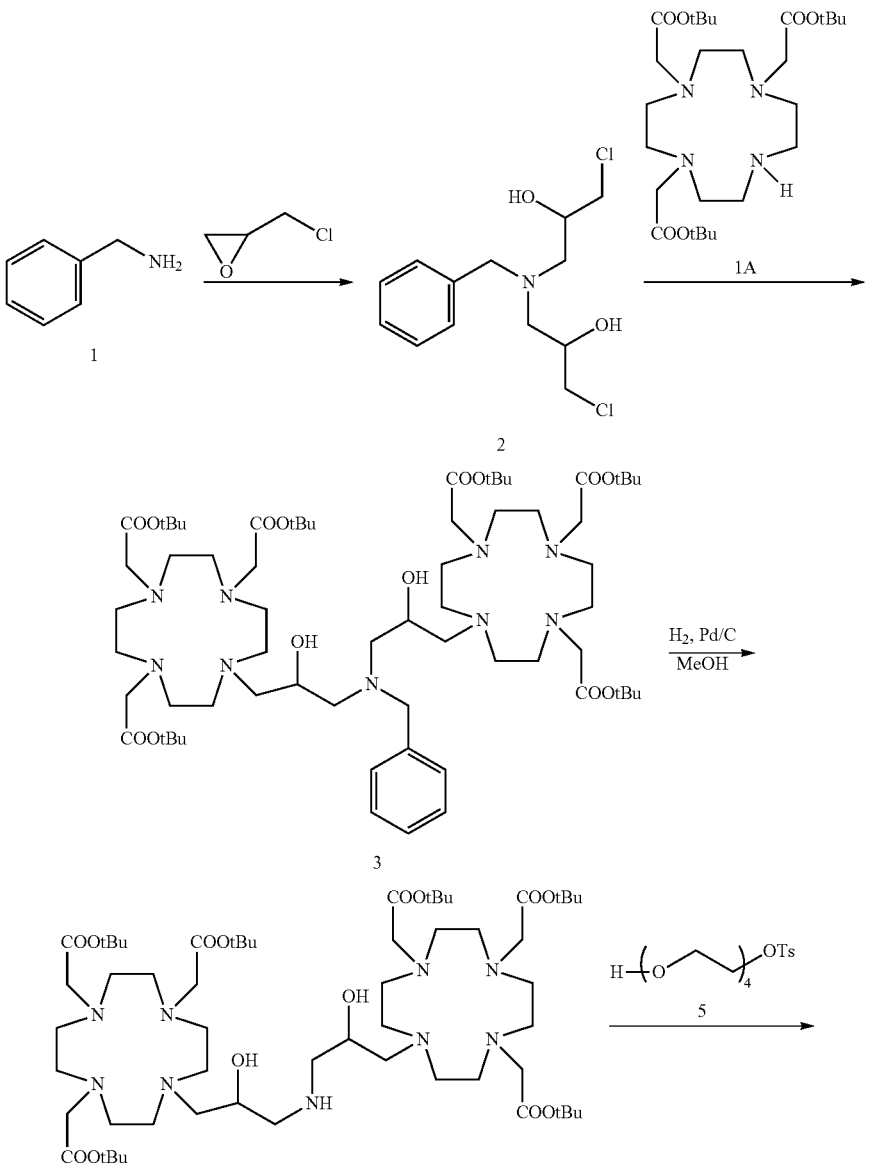

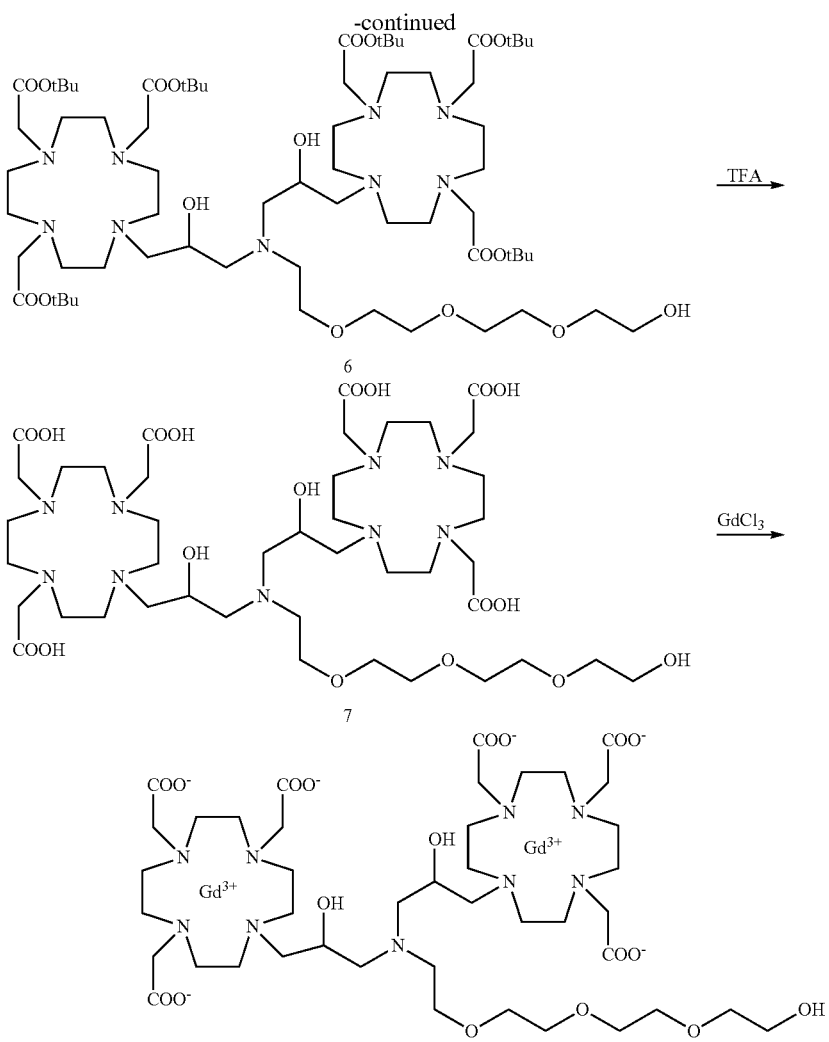

including:

a) Preparation of 2

Commercially available epichlorohydrin (3.3 g; 36 mmol) was added to a solution of commercial available benzylamine 1 (1.64 g; 15 mmol) in EtOH (10 mL). The mixture was stirred at room temperature for 30 h then evaporated to give compound 2 that was directly used for the next reaction without any further purification. Quantitative yield.

1H-NMR, 13C-NMR and mass spectrum were consistent with the expected structure.

b) Preparation of 3

A solution of substrate 1A (15.4 g; 30 mmol) in MeCN (30 mL) was added to a solution of compound 2 (4.38 g; 15 mmol) in MeCN (30 mL) and Et$_3$N (6.3 mL). The mixture was stirred at 55° C. for 96 h, then evaporated. The residue was purified by flash chromatography on silica gel (eluent: CH$_2$Cl$_2$/MeOH=100:1→1:1) to give intermediate 3 (10 g). Yield 53%.

1H-NMR, 13C-NMR and mass spectrum were consistent with the expected structure.

c) Preparation of 4

A solution of intermediate 3 (10 g; 8 mmol) in methanol (80 mL) was added with 5% palladium on carbon (wet with about 50% water) (2.5 g) and hydrogenated at 45° C. for 5 h. Additional catalyst (0.8 g) was added and the mixture hydrogenated at 45° C. for other 4 h. The catalyst was filtered and the solution evaporated to give intermediate 4 (8.9 g). Yield 96%.

1H-NMR, 13C-NMR and mass spectrum were consistent with the expected structure.

d) Preparation of 6

Tetraethylene glycol monotosylate 5 (2.6 g, 7.5 mmol) (commercial product, e.g. Aldrich) was added to a solution of 4 (8.5 g; 7.3 mmol) in MeCN (100 mL) and the mixture was stirred for 72 h. The mixture was evaporated, the residue dissolved in CHCl$_3$ (200 mL) and washed with water (2×100 mL). The organic phase was separated, dried and evaporated. The residue was purified by flash chromatography on silica gel (eluent: CH$_2$Cl$_2$/MeOH=100:1→1:1) to give compound 6 (4.7 g). Yield 48%

1H-NMR, 13C-NMR and mass spectrum were consistent with the expected structure.

e) Preparation of 7

Trifluoroacetic acid (5 mL) was added to a solution of intermediate 6 (8 g; 6.3 mmol) in dichloromethane (50 mL). The mixture stirred for 30 min then was evaporated. The residue was dissolved in TFA (20 mL) and triisopropylsilane (0.1 mL) was added. The obtained mixture was stirred for 24 h at room temperature then evaporated and the residue purified by chromatography on Amberlite XE 750 column (eluent: gradient of water/MeCN) obtaining the ligand 7 (5.3 g). Yield 84%.

1H-NMR, 13C-NMR and mass spectrum were consistent with the expected structure.

f) Complexation

Ligand 7 (4.5 g; 4.5 mmol) was dissolved in water (100 mL), gadolinium chloride hexahydrate (3.35 g; 9 mmol) was added, then 1M NaOH was added to achieve pH 7. The mixture was stirred at 50° C. for 18 h. The solution was then filtered on Millipore HA 0.25 μm filters and evaporated under reduced pressure. The crude product was purified on Amberchrome CG161M column (eluent: gradient of water/acetonitrile). The fractions containing the pure product were pooled and evaporated. The solid product was dried under vacuum to obtain the gadolinium complex as a white powder (4.4 g). Yield 75%.

Mass spectrum and elemental analysis were consistent with the expected structure.

Example 4: Preparation of the Chelate Complex 3

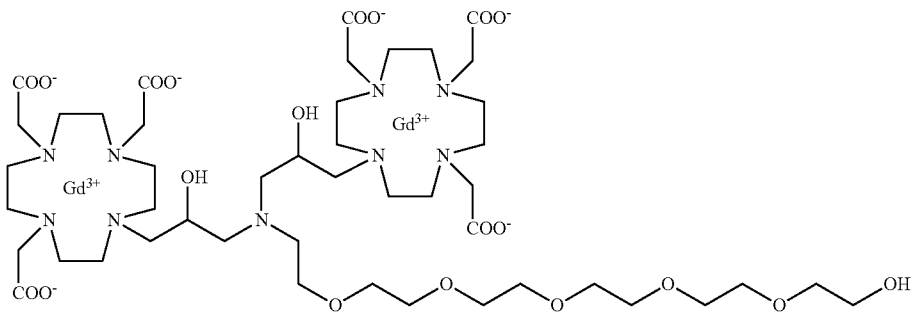

This complex compound was obtained by using the procedure shown in Scheme 7:

Scheme 7

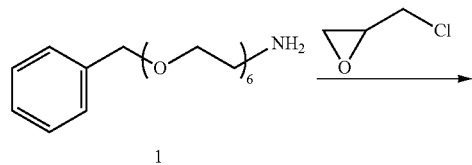

1

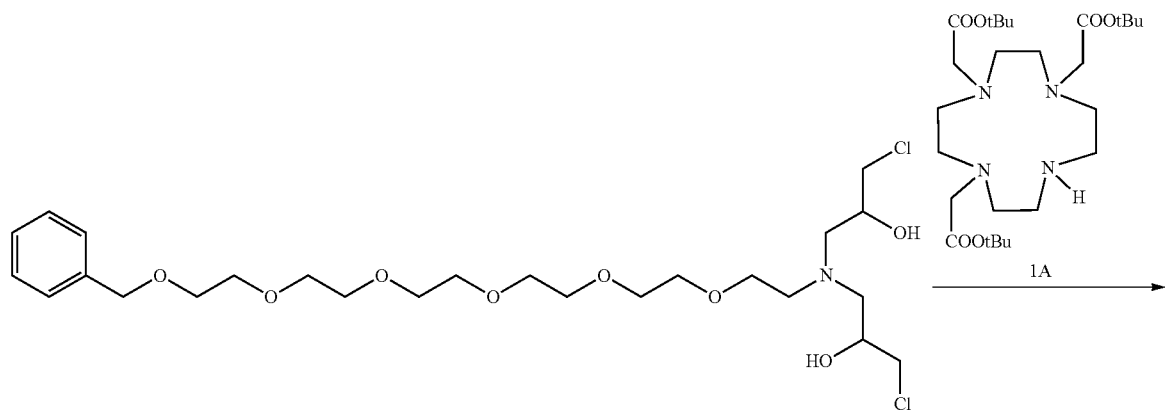

2

-continued

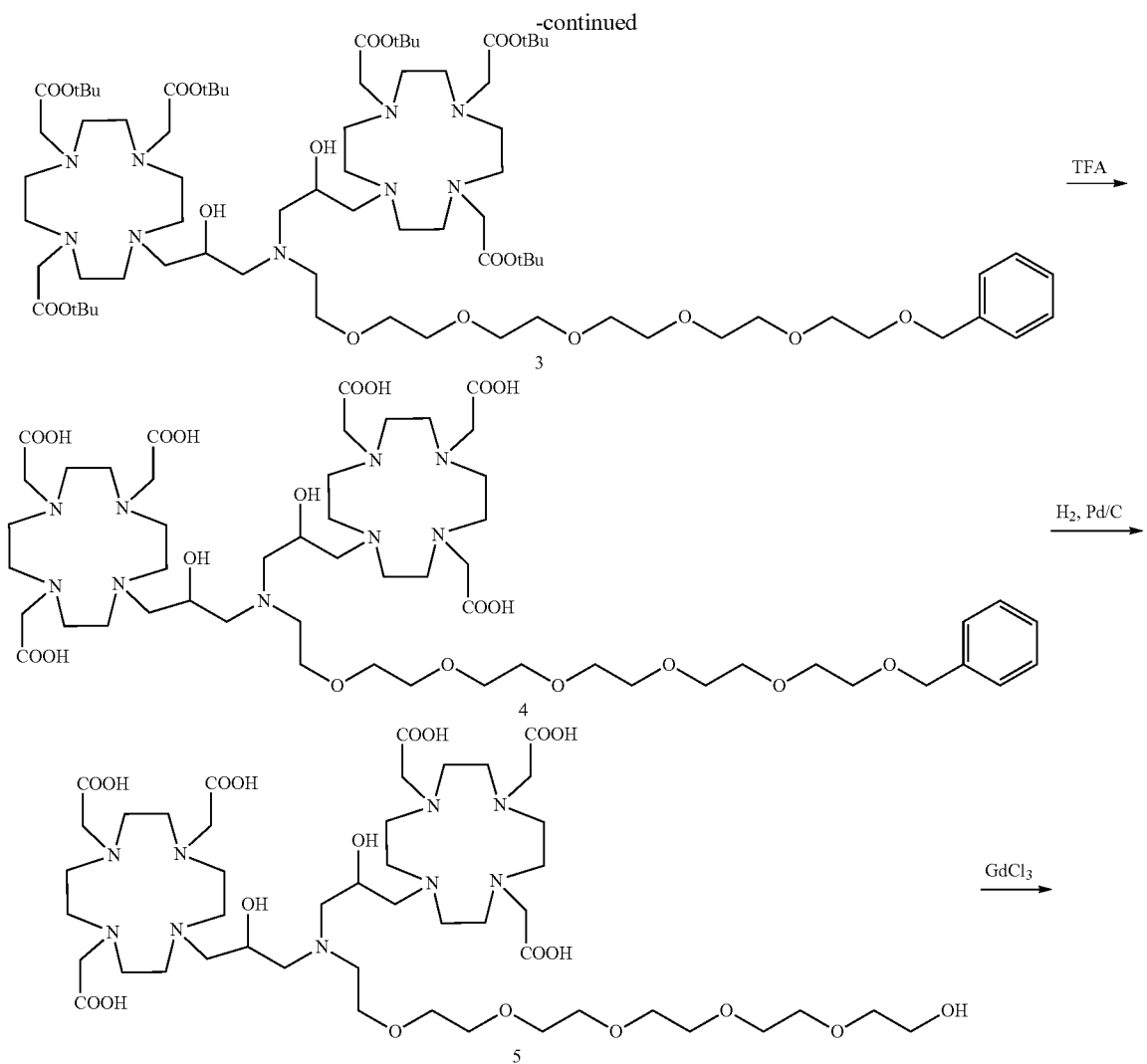

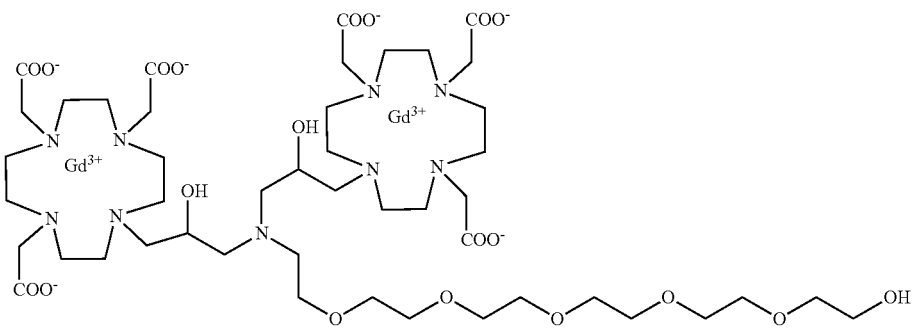

including:

a) Preparation of 2

A mixture of amine 1 (prepared for instance as disclosed in *Tetrahedron Lett.* 1983, 24, 1609) (11.2 g; 30 mmol) and epichlorohydrin (5.6 g; 60 mmol) in EtOH (20 mL) was stirred at room temperature for 24 h then evaporated to give compound 2 that was directly used for the next reaction without any further purification. Quantitative yield.

1H-NMR, 13C-NMR and mass spectrum were consistent with the expected structure.

b) Preparation of 3

A mixture of substrate 1A (15.4 g; 30 mmol) in MeCN (50 mL) was added to a solution of compound 2 (8.3 g; 15 mmol) in MeCN (50 mL) and Et$_3$N (6 mL). The mixture was stirred at 55° C. for 96 h then evaporated. The residue was purified by flash chromatography on silica gel (eluent: CH$_2$Cl$_2$/MeOH=100:1→1:1) to give intermediate 3 (10.9 g). Yield 48%.

1H-NMR, 13C-NMR and mass spectrum were consistent with the expected structure.

c) Preparation of 4

Trifluoroacetic acid (10 mL) was added to a solution of intermediate 3 (9 g; 6 mmol) in dichloromethane (50 mL). The mixture stirred for 30 min then was evaporated. The residue was dissolved in TFA (25 mL) and triisopropylsilane (0.1 mL) was added. The obtained mixture was stirred for 24 h at room temperature then evaporated and the residue purified by chromatography on Amberlite XE 750 column (eluent: gradient of water/MeCN) obtaining compound 4 (5.9 g). Yield 83%.

1H-NMR, 13C-NMR and mass spectrum were consistent with the expected structure.

d) Preparation of 5

A solution of intermediate 4 (5.5 g; 4.7 mmol) in methanol (100 mL) was added with 5% palladium on carbon (wet with about 50% water) (1.5 g) and hydrogenated at room temperature for 24 h. The catalyst was filtered and the solution evaporated to give ligand 5 (5 g). Yield 98%.

1H-NMR, 13C-NMR and mass spectrum were consistent with the expected structure.

e) Complexation

Ligand 5 (5 g; 4.6 mmol) was dissolved in water (100 mL), gadolinium chloride hexahydrate (3.42 g; 9.2 mmol) was added then 1M NaOH was added to achieve pH 7. The mixture was stirred at 50° C. for 18 h. The solution was then filtered on Millipore HA 0.25 μm filters and evaporated under reduced pressure. The crude product was purified on Amberchrome CG161M column (eluent: gradient of water/ acetonitrile). The fractions containing the pure product were pooled and evaporated. The solid product was dried under vacuum to obtain the gadolinium complex as a white powder (5.6 g). Yield 87%.

Mass spectrum and elemental analysis were consistent with the expected structure.

Example 5: Preparation of the Chelate Complex 4

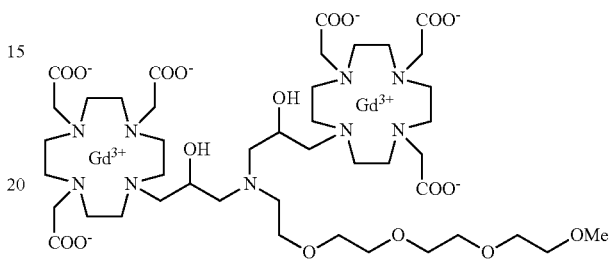

This complex compound was obtained by using the procedure shown in Scheme 8:

Scheme 8

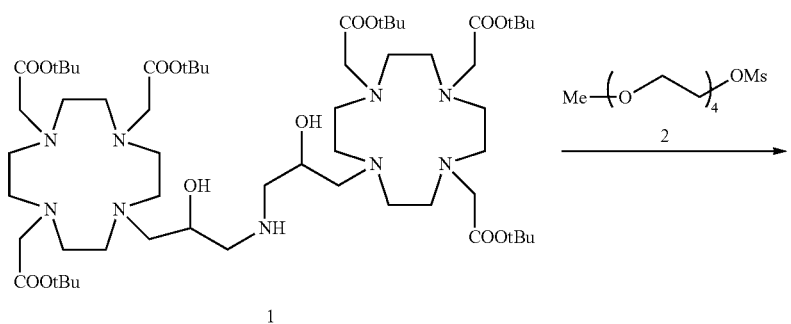

1

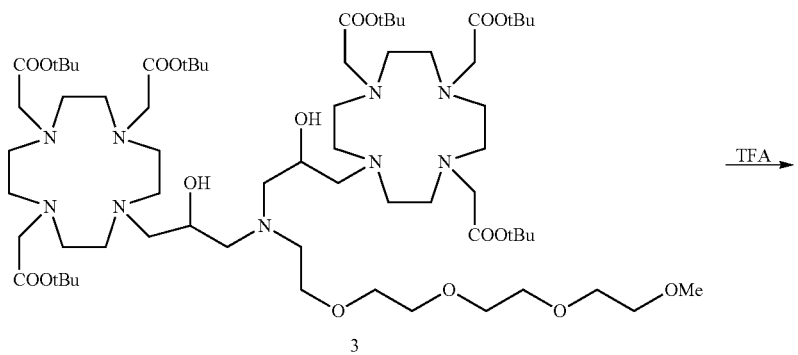

3

-continued

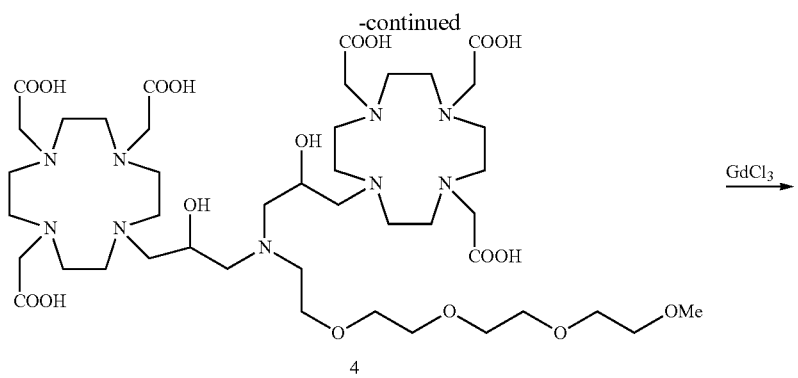

4

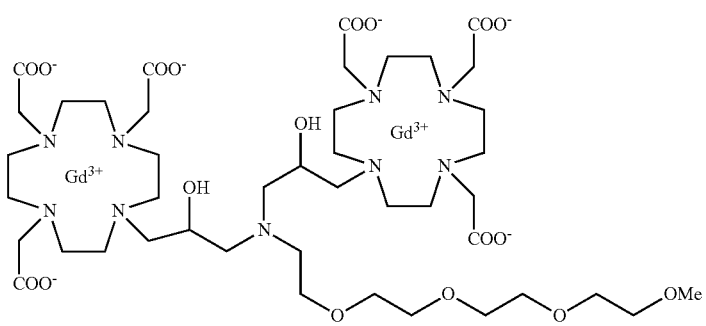

including:

a) Preparation of 3

Compound 2 (*Synlett* 2005, 2342) (2.9 g, 10 mmol) was added to a solution of 1 (prepared as described in Example 3) (11.6 g; 10 mmol) in MeCN (100 mL) and the mixture was stirred at reflux for 48 h. The mixture was evaporated, the residue dissolved in $CHCl_3$ (200 mL) and washed with water (2×100 mL). The organic phase was separated, dried and evaporated. The residue was purified by flash chromatography on silica gel (eluent: $CH_2Cl_2$/MeOH=100:1→1:1) to give compound 3 (7.4 g). Yield 55%.

1H-NMR, 13C-NMR and mass spectrum were consistent with the expected structure.

b) Preparation of 4

Trifluoroacetic acid (10 mL) was added to a solution of intermediate 3 (6.75 g; 5 mmol) in dichloromethane (50 mL). The mixture stirred for 30 min then was evaporated. The residue was dissolved in TFA (25 mL) and triisopropylsilane (0.1 mL) was added. The obtained mixture was stirred for 24 h at room temperature then evaporated and the residue purified by chromatography on Amberlite XE 750 column (eluent: gradient of water/MeCN) obtaining ligand 4 (4.1 g). Yield 81%.

1H-NMR, 13C-NMR and mass spectrum were consistent with the expected structure.

c) Complexation

Ligand 4 (5 g; 4.9 mmol) was dissolved in water (100 mL), gadolinium chloride hexahydrate (3.64 g; 9.8 mmol) was added, then 1M NaOH was added to achieve pH 7. The mixture was stirred at 50° C. for 18 h. The solution was then filtered on Millipore HA 0.25 μm filters and evaporated under reduced pressure. The crude product was purified on Amberchrome CG161M column (eluent: gradient of water/acetonitrile). The fractions containing the pure product were pooled and evaporated. The solid product was dried under vacuum to obtain the gadolinium complex as a white powder (5.2 g). Yield 80%.

Mass spectrum and elemental analysis were consistent with the expected structure.

Example 6: Preparation of the Chelate Complex 5

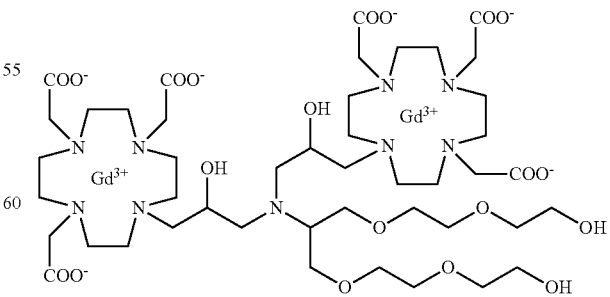

This complex compound was obtained by using the procedure shown in Scheme 9:

Scheme 9
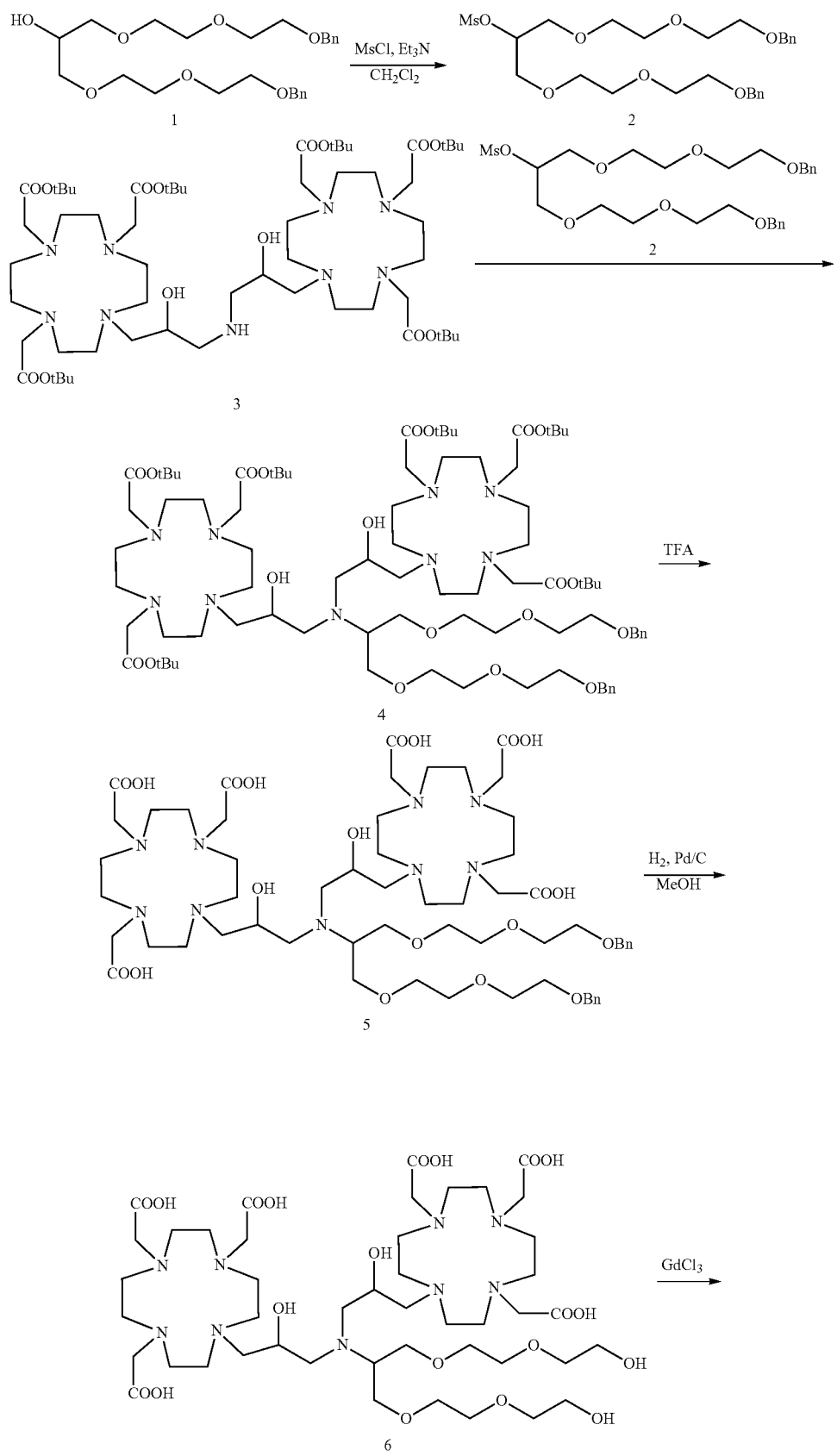

-continued

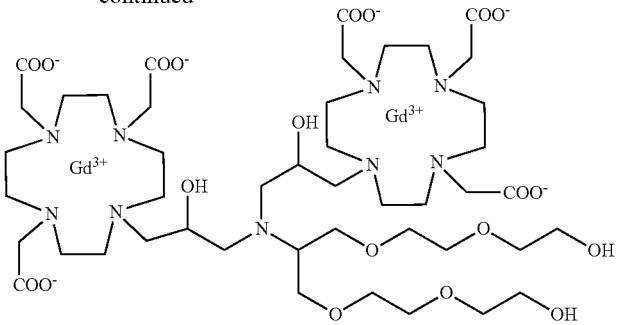

including:

a) Preparation of 2

Methanesulfonyl chloride (2.52 g; 22 mmol) was slowly added to a solution of compound 1 (prepared e.g. as disclosed in EP 1854792) (9 g; 20 mmol) and Et$_3$N (3 mL) in dichloromethane (100 mL) and the solution was stirred for 18 h. The reaction mixture was extracted with water (3×100 mL). The organic phase was evaporated to give compound 2 that was directly used for the next reaction without any further purification. Quantitative yield.

1H-NMR, 13C-NMR and mass spectrum were consistent with the expected structure.

b) Preparation of 4

Compound 2 (5.3 g, 10 mmol) was added to a solution of compound 3 (prepared as described in Example 3) (11.6 g; 10 mmol) in MeCN (100 mL) and the mixture was stirred at reflux for 48 h. The mixture was evaporated, the residue dissolved in CHCl$_3$ (200 mL) and washed with water (2×100 mL). The organic phase was separated, dried and evaporated. The residue was purified by flash chromatography on silica gel (eluent: CH$_2$Cl$_2$/MeOH=100:1→1:1) to give compound 4 (8.1 g). Yield 51%.

1H-NMR, 13C-NMR and mass spectrum were consistent with the expected structure.

c) Preparation of 5

Trifluoroacetic acid (10 mL) was added to a solution of compound 4 (7.95 g; 5 mmol) in dichloromethane (50 mL). The mixture stirred for 30 min then was evaporated. The residue was dissolved in TFA (25 mL) and triisopropylsilane (0.1 mL) was added. The obtained mixture was stirred for 24 h at room temperature then evaporated and the residue purified by chromatography on Amberlite XE 750 column (eluent: gradient of water/MeCN) obtaining compound 5 (5.45 g). Yield 87%.

1H-NMR, 13C-NMR and mass spectrum were consistent with the expected structure.

d) Preparation of 6

A solution of intermediate 5 (5 g; 4 mmol) in methanol (100 mL) was added with 5% palladium on carbon (wet with about 50% water) (1.5 g) and hydrogenated at room temperature for 24 h. The catalyst was filtered and the solution evaporated to give ligand 6 (4.15 g). Yield 97%.

1H-NMR, 13C-NMR and mass spectrum were consistent with the expected structure.

e) Complexation

Ligand 6 (4 g; 3.7 mmol) was dissolved in water (100 mL), gadolinium chloride hexahydrate (2.75 g; 7.4 mmol) was added then 1M NaOH was added to achieve pH 7. The mixture was stirred at 50° C. for 18 h. The solution was then filtered on Millipore HA 0.25 μm filters and evaporated under reduced pressure. The crude product was purified on Amberchrome CG161M column (eluent: gradient of water/acetonitrile). The fractions containing the pure product were pooled and evaporated. The solid product was dried under vacuum to obtain the gadolinium complex as a white powder (4.6 g). Yield 89%.

Mass spectrum and elemental analysis were consistent with the expected structure.

Example 7: Preparation of the Chelate Complex 6

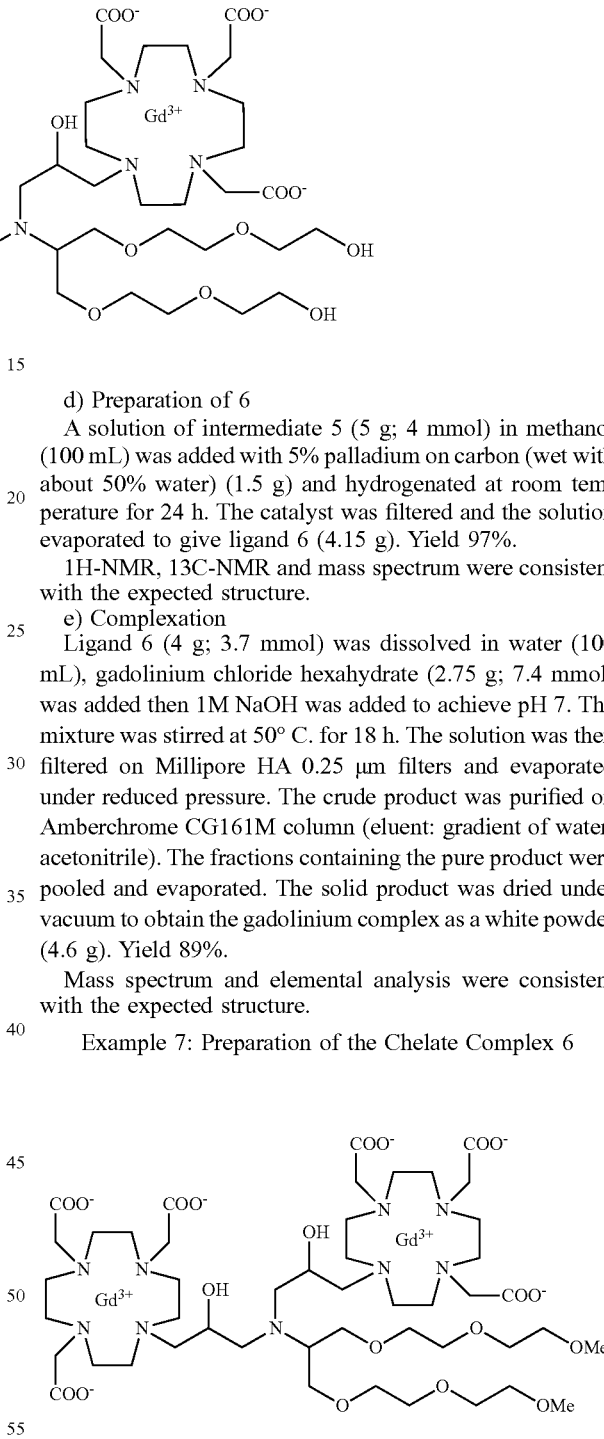

This complex compound was obtained by using the procedure shown in Scheme 10:

Scheme 10

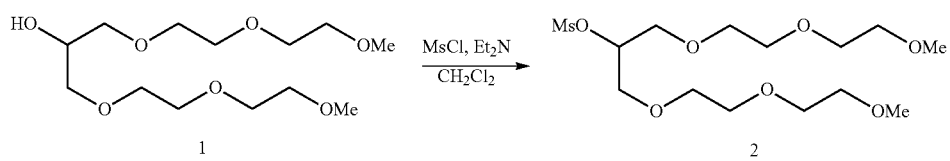

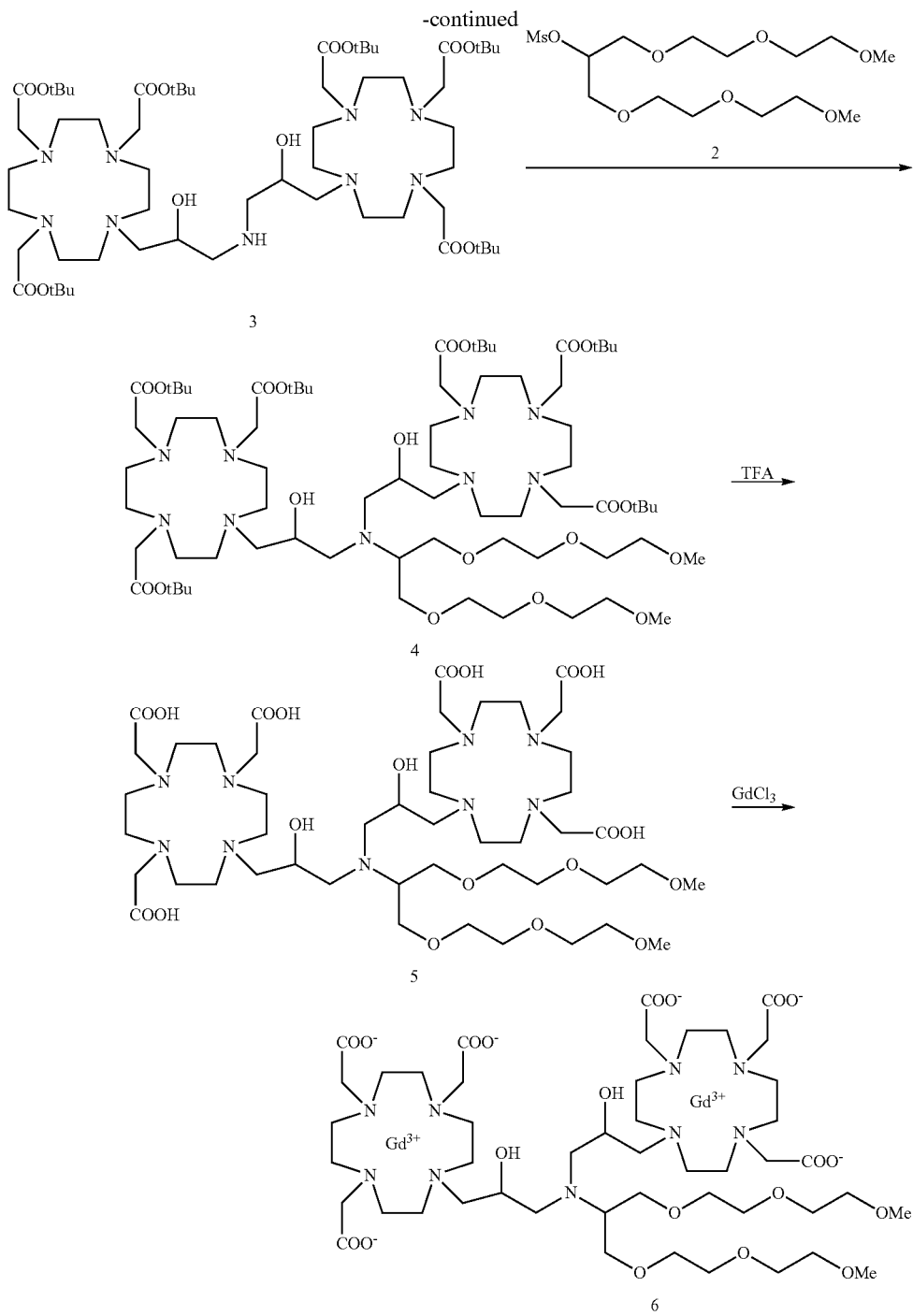

comprising:

a) Preparation of 2

Methanesulfonyl chloride (3.5 g; 30 mmol) was slowly added to a solution of compound 1 (prepared e.g. as described in WO2016/193748) (8.9 g; 30 mmol) and Et₃N (5 mL) in dichloromethane (200 mL) and the solution was stirred for 18 h. The reaction mixture was extracted with water (3×200 mL). The organic phase was evaporated to give compound 2 that was directly used for the next reaction without any further purification. Quantitative yield.

1H-NMR, 13C-NMR and mass spectrum were consistent with the expected structure.

b) Preparation of 4

Compound 2 (5.6 g, 15 mmol) was added to a solution of 3 (prepared as described in Example 3) (17.4 g; 15 mmol) in MeCN (100 mL) and the mixture was stirred at reflux for 48 h. The mixture was evaporated, the residue dissolved in CHCl₃ (200 mL) and washed with water (2×100 mL). The organic phase was separated, dried and evaporated. The residue was purified by flash chromatography on silica gel (eluent: CH₂Cl₂/MeOH=100:1→1:1) to give compound 4 (11.8 g). Yield 55%.

1H-NMR, 13C-NMR and mass spectrum were consistent with the expected structure.

c) Preparation of 5

Trifluoroacetic acid (15 mL) was added to a solution of intermediate 4 (10 g; 7 mmol) in dichloromethane (80 mL). The mixture stirred for 30 min then was evaporated. The residue was dissolved in TFA (50 mL) and triisopropylsilane (0.1 mL) was added. The obtained mixture was stirred for 24 h at room temperature then evaporated and the residue purified by chromatography on Amberlite XE 750 column (eluent: gradient of water/MeCN) obtaining ligand 5 (6.5 g). Yield 84%.

1H-NMR, 13C-NMR and mass spectrum were consistent with the expected structure.

d) Complexation

Ligand 5 (5.5 g; 5 mmol) was dissolved in water (100 mL), gadolinium chloride hexahydrate (3.7 g; 10 mmol) was added then 1M NaOH was added to achieve pH 7. The mixture was stirred at 50° C. for 18 h. The solution was then filtered on Millipore HA 0.25 μm filters and evaporated under reduced pressure. The crude product was purified on Amberchrome CG161M column (eluent: gradient of water/acetonitrile). The fractions containing the pure product were pooled and evaporated. The solid product was dried under vacuum to obtain the gadolinium complex as a white powder (6.2 g). Yield 88%.

Mass spectrum and elemental analysis were consistent with the expected structure.

Example 8: Preparation of the Chelate Complex 7

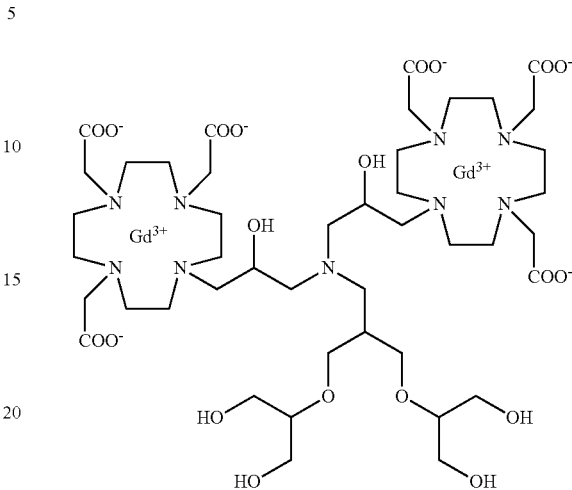

This compound was obtained by using the procedure shown in Scheme 11:

Scheme 11

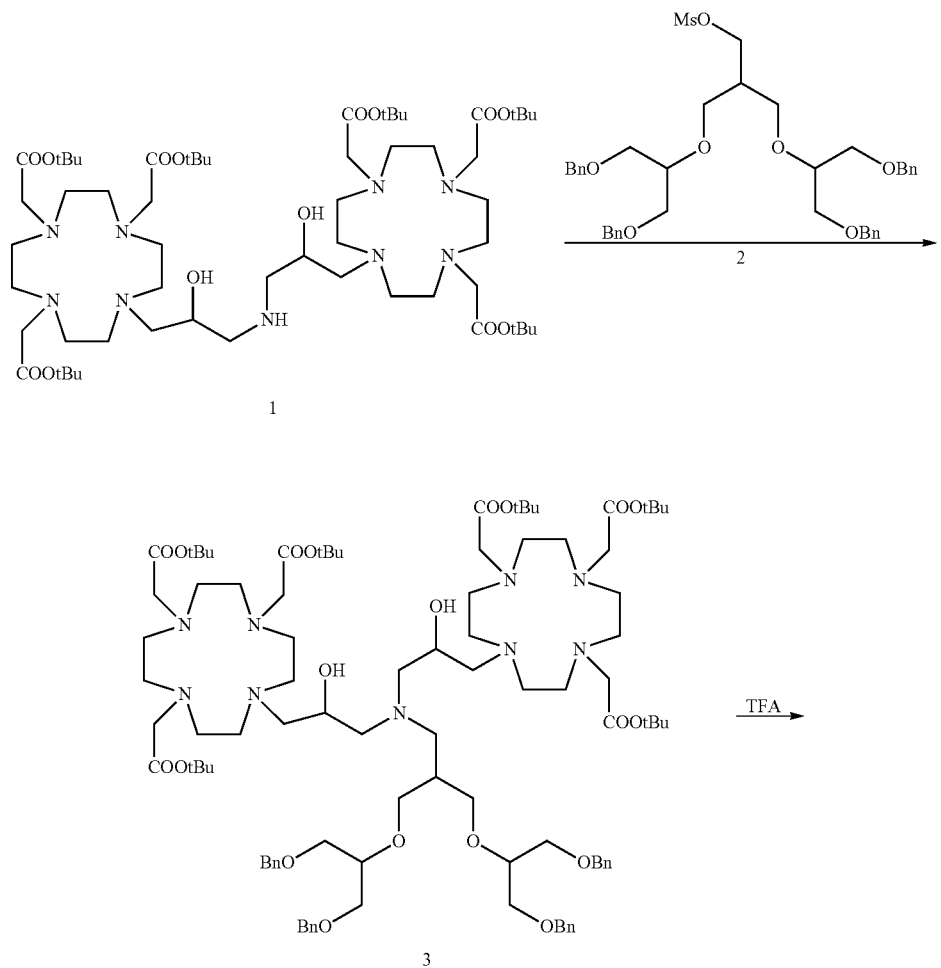

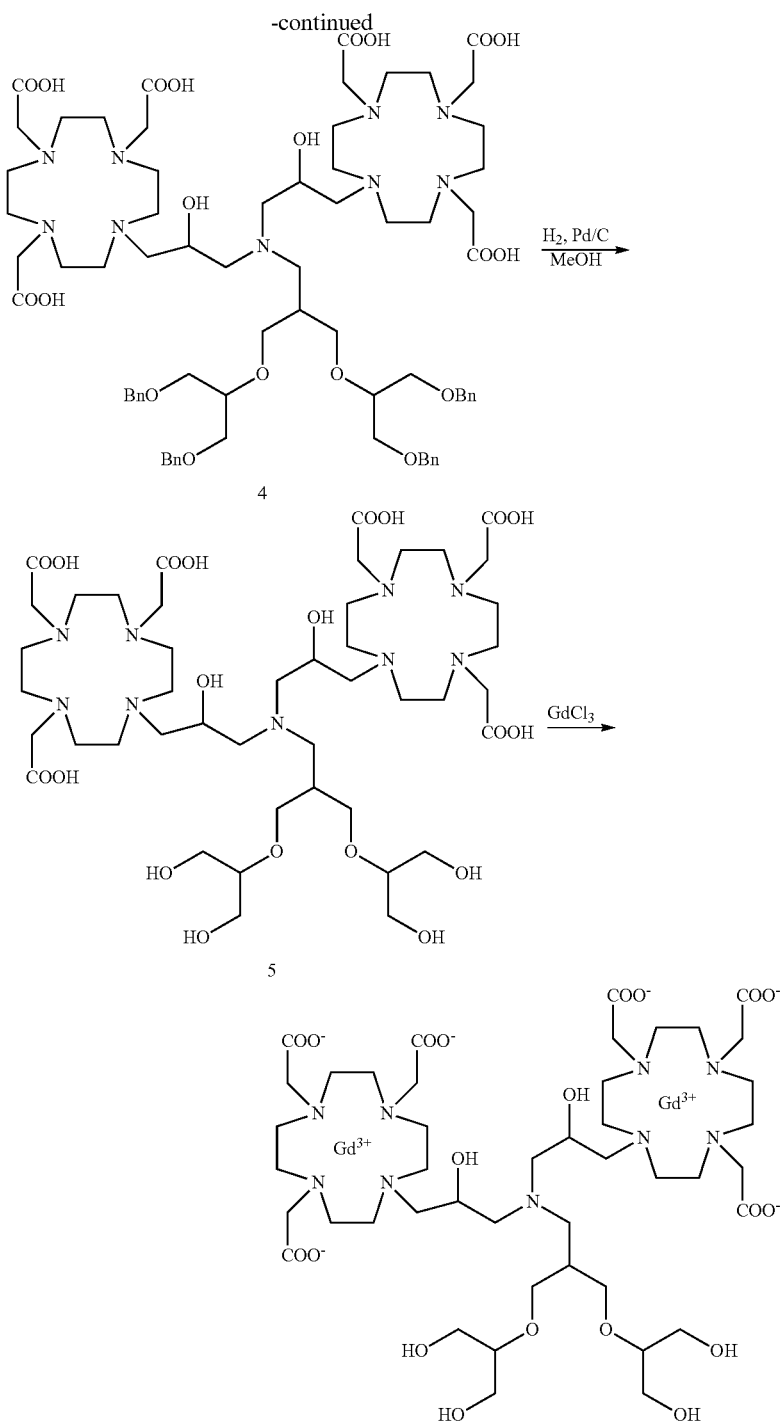

comprising:

a) Preparation of 3

Compound 2 (prepared e.g. as described in *Chem. Commun.* 2005, 474) (10.4 g, 15 mmol) was added to a solution of 1 (prepared as described in Example 3) (17.4 g; 15 mmol) in MeCN (100 mL) and the mixture was stirred at reflux for 48 h. The mixture was evaporated, the residue dissolved in CHCl₃ (200 mL) and washed with water (2×100 mL). The organic phase was separated, dried and evaporated. The residue was purified by flash chromatography on silica gel (eluent: CH$_2$Cl$_2$/MeOH=100:1→1:1) to give compound 3 (15.5 g). Yield 59%.

1H-NMR, 13C-NMR and mass spectrum were consistent with the expected structure.

b) Preparation of 4

Trifluoroacetic acid (10 mL) was added to a solution of intermediate 3 (8.8 g; 5 mmol) in dichloromethane (60 mL). The mixture stirred for 30 min then was evaporated. The residue was dissolved in TFA (50 mL) and triisopropylsilane (0.1 mL) was added. The obtained mixture was stirred for 24 h at room temperature then evaporated and the residue purified by chromatography on Amberlite XE 750 column (eluent: gradient of water/MeCN) obtaining compound 4 (6.4 g). Yield 90%.

1H-NMR, 13C-NMR and mass spectrum were consistent with the expected structure.

c) Preparation of 5

A solution of intermediate 4 (6.1 g; 4.3 mmol) in methanol (100 mL) was added with 5% palladium on carbon (wet with about 50% water) (1.5 g) and hydrogenated at room temperature for 24 h. The catalyst was filtered and the solution evaporated to give ligand 5 (4.5 g). Yield 99%.

1H-NMR, 13C-NMR and mass spectrum were consistent with the expected structure.

d) Complexation

Ligand 5 (4.2 g; 4 mmol) was dissolved in water (100 mL), gadolinium chloride hexahydrate (2.97 g; 8 mmol) was added, then 1M NaOH was added to achieve pH 7. The mixture was stirred at 50° C. for 18 h. The solution was then filtered on Millipore HA 0.25 μm filters and evaporated under reduced pressure. The crude product was purified on Amberchrome CG161M column (eluent: gradient of water/acetonitrile). The fractions containing the pure product were pooled and evaporated. The solid product was dried under vacuum to obtain the gadolinium complex as a white powder (4.9 g). Yield 90%.

Mass spectrum and elemental analysis were consistent with the expected structure.

Example 9: Preparation of the Chelate Complex 8

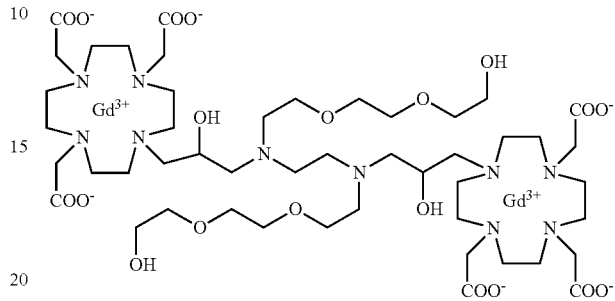

This compound was obtained by using the procedure shown in Scheme 12:

Scheme 12

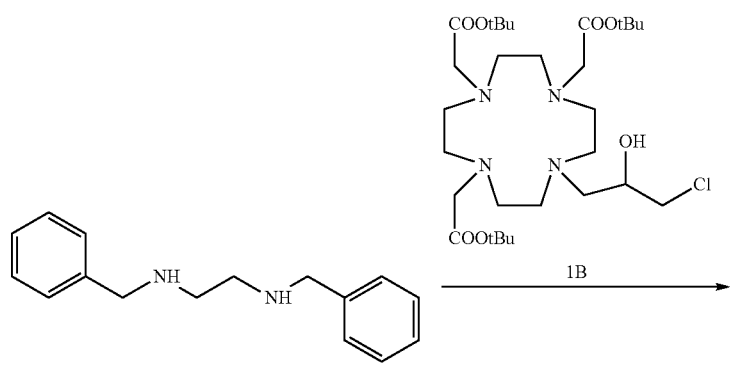

2

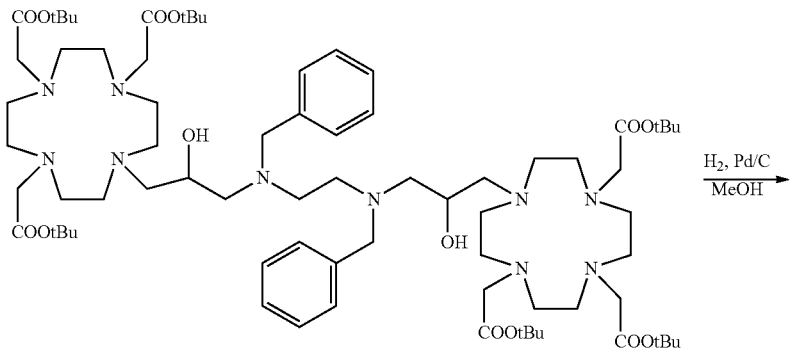

3

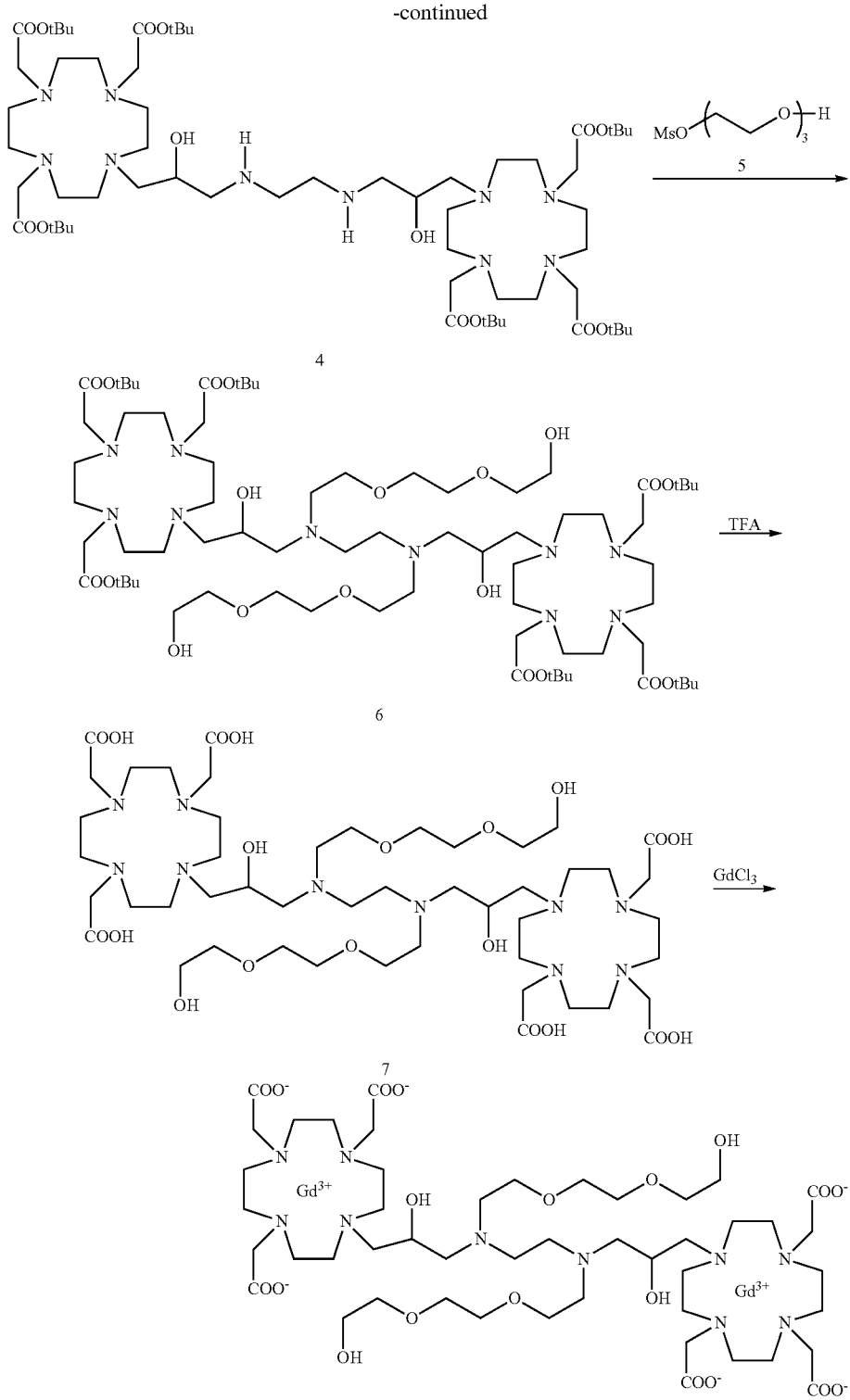

comprising:

a) Preparation of 3

A mixture of commercial available amine 2 (6 g; 25 mmol), compound 1B (30.4 g; 50 mmol) and Et$_3$N (10 mL) in acetonitrile (300 mL) was stirred at room temperature for 72 h then evaporated. The residue was purified by flash chromatography on silica gel (eluent: CH$_2$Cl$_2$/MeOH=100:1→1:2) to give compound 3 (16.2 g). Yield 47%.

1H-NMR, 13C-NMR and mass spectrum were consistent with the expected structure.

b) Preparation of 4

A solution of intermediate 3 (15.2 g; 11 mmol) in methanol (150 mL) was added with 5% palladium on carbon (wet with about 50% water) (4 g) and hydrogenated at 45° C. for 16 h. The catalyst was filtered and the solution evaporated to give intermediate 4 (11.9 g). Yield 90%.

1H-NMR, 13C-NMR and mass spectrum were consistent with the expected structure.

c) Preparation of 6

Triethylene glycol monomesylate 5 (prepared as reported in patent EP2842940) (4.6 g, 20 mmol) was added to a solution of compound 4 (10.8 g; 9 mmol) in MeCN (100 mL) and the mixture was stirred for 72 h. The mixture was evaporated, the residue dissolved in CHCl₃ (200 mL) and washed with water (2×100 mL). The organic phase was separated, dried and evaporated. The residue was purified by flash chromatography on silica gel (eluent: CH₂Cl₂/MeOH=100:1→1:1) to give compound 6 (5.9 g). Yield 45%.

1H-NMR, 13C-NMR and mass spectrum were consistent with the expected structure.

d) Preparation of 7

Trifluoroacetic acid (10 mL) was added to a solution of intermediate 6 (7.3 g; 5 mmol) in dichloromethane (60 mL). The mixture stirred for 30 min then was evaporated. The residue was dissolved in TFA (50 mL) and triisopropylsilane (0.1 mL) was added. The obtained mixture was stirred for 24 h at room temperature then evaporated and the residue purified by chromatography on Amberlite XE 750 column (eluent: gradient of water/MeCN) obtaining ligand 7 (5.4 g). Yield 95%.

1H-NMR, 13C-NMR and mass spectrum were consistent with the expected structure.

e) Complexation

Ligand 7 (4.5 g; 4 mmol) was dissolved in water (100 mL), gadolinium chloride hexahydrate (2.97 g; 8 mmol) was added, then 1M NaOH was added to achieve pH 7. The mixture was stirred at 50° C. for 18 h. The solution was then filtered on Millipore HA 0.25 μm filters and evaporated under reduced pressure. The crude product was purified on Amberchrome CG161M column (eluent: gradient of water/acetonitrile). The fractions containing the pure product were pooled and evaporated. The solid product was dried under vacuum to obtain the gadolinium complex as a white powder (4.8 g). Yield 83%.

Mass spectrum and elemental analysis were consistent with the expected structure.

Example 10: Preparation of the Chelate Complex 9

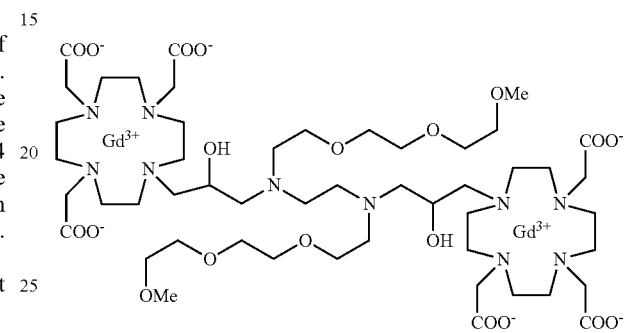

This compound was obtained by using the procedure shown in Scheme 13:

Scheme 13

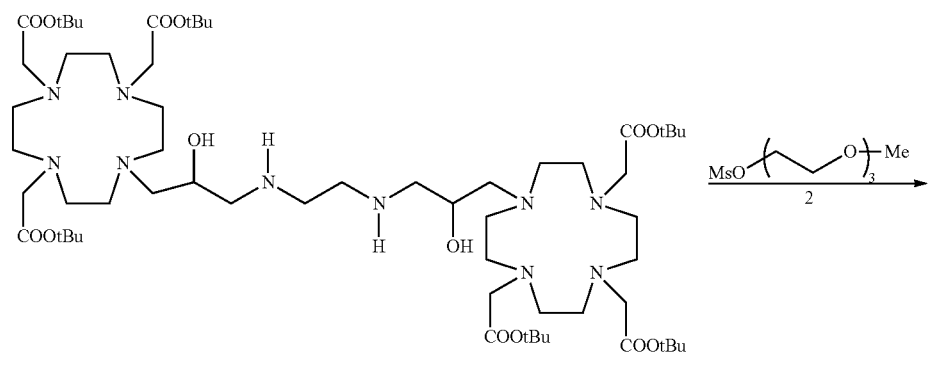

1

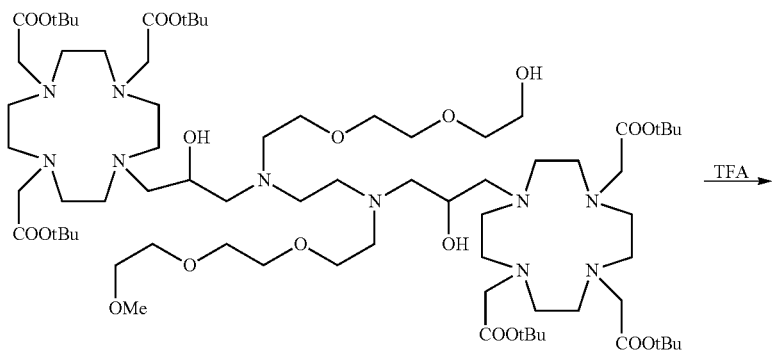

3

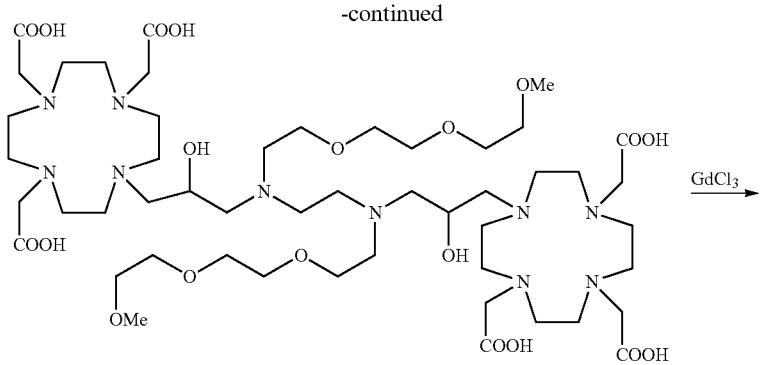

4

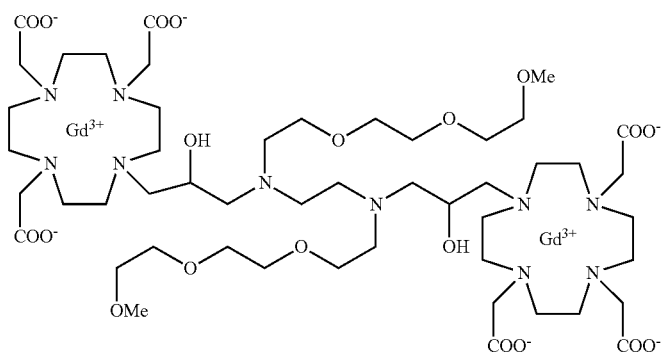

comprising a) Preparation of 3

Compound 2 (prepared e.g. as disclosed *Synlett* 2005, 2342) (5.7 g, 20 mmol) was added to a solution of compound 1 (prepared as described in Example 9) (10.8 g; 9 mmol) in MeCN (100 mL) and the mixture was stirred for 72 h. The mixture was evaporated, the residue dissolved in $CHCl_3$ (200 mL) and washed with water (2×100 mL). The organic phase was separated, dried and evaporated. The residue was purified by flash chromatography on silica gel (eluent: $CH_2Cl_2$/MeOH=100:1-*1:2) to give compound 3 (6.5 g). Yield 48%.

1H-NMR, 13C-NMR and mass spectrum were consistent with the expected structure.

b) Preparation of 4

Trifluoroacetic acid (10 mL) was added to a solution of intermediate 3 (9 g; 6 mmol) in dichloromethane (60 mL). The mixture stirred for 30 min then was evaporated. The residue was dissolved in TFA (50 mL) and triisopropylsilane (0.1 mL) was added. The obtained mixture was stirred for 24 h at room temperature then evaporated and the residue purified by chromatography on Amberlite XE 750 column (eluent: gradient of water/MeCN) obtaining ligand 4 (6.5 g). Yield 94%.

1H-NMR, 13C-NMR and mass spectrum were consistent with the expected structure.

c) Complexation

Ligand 4 (4.6 g; 4 mmol) was dissolved in water (100 mL), gadolinium chloride hexahydrate (2.97 g; 8 mmol) was added then 1M NaOH was added to achieve pH 7. The mixture was stirred at 50° C. for 18 h. The solution was then filtered on Millipore HA 0.25 μm filters and evaporated under reduced pressure. The crude product was purified on Amberchrome CG161M column (eluent: gradient of water/acetonitrile). The fractions containing the pure product were pooled and evaporated. The solid product was dried under vacuum to obtain the gadolinium complex as a white powder (5.1 g). Yield 87%.

Mass spectrum and elemental analysis were consistent with the expected structure.

Example 11: Preparation of the Chelate Complex 10

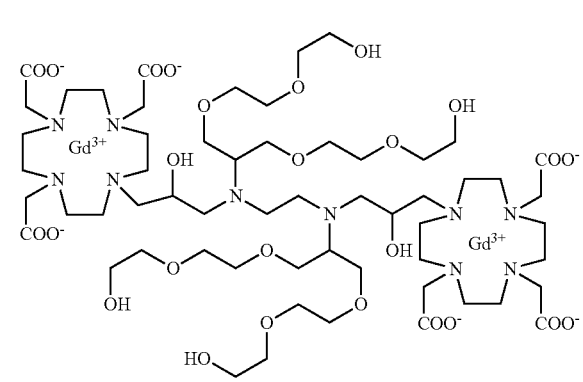

This compound was obtained by using the procedure shown in Scheme 14:

Scheme 14
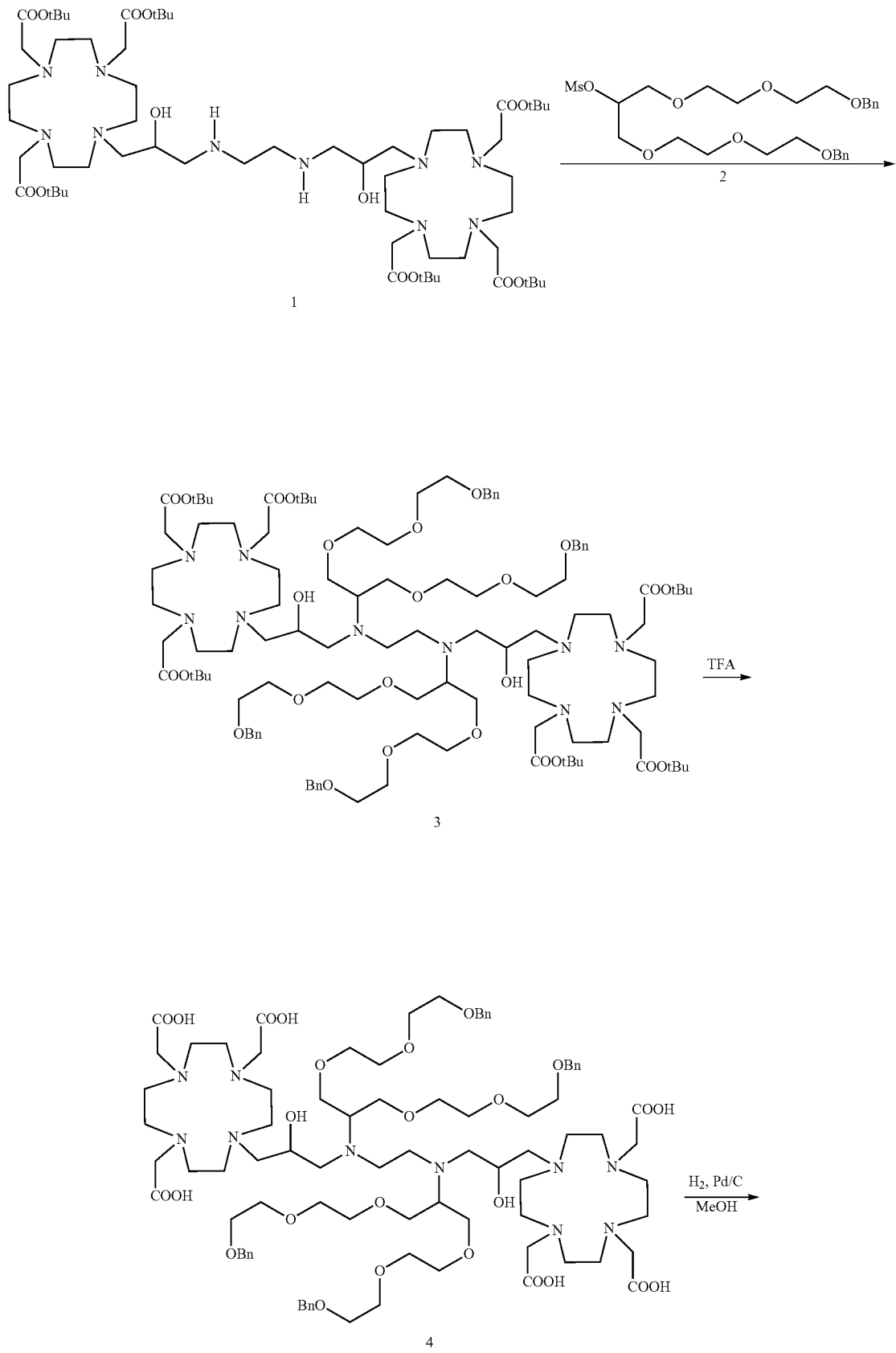

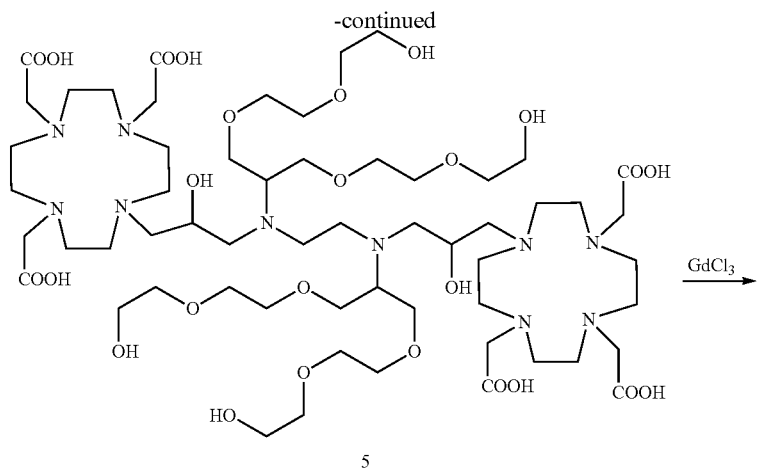

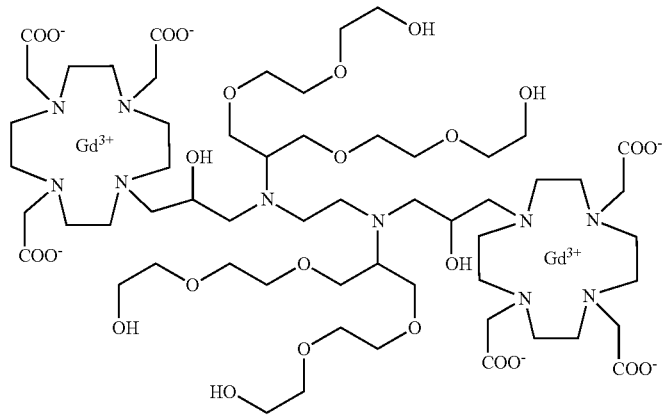

comprising:

a) Preparation of 3

Compound 2 (prepared as described in Example 6) (10.5 g, 20 mmol) was added to a solution of compound 1 (prepared as described in Example 9) (10.8 g; 9 mmol) in MeCN (150 mL) and the mixture was stirred for 72 h. The mixture was evaporated, the residue dissolved in CHCl$_3$ (200 mL) and washed with water (2×100 mL). The organic phase was separated, dried and evaporated. The residue was purified by flash chromatography on silica gel (eluent: CH$_2$Cl$_2$/MeOH=100:1→1:2) to give compound 3 (7 g). Yield 38%.

1H-NMR, 13C-NMR and mass spectrum were consistent with the expected structure.

b) Preparation of 4

Trifluoroacetic acid (15 mL) was added to a solution of intermediate 3 (16.5 g; 8 mmol) in dichloromethane (120 mL). The mixture stirred for 30 min then was evaporated. The residue was dissolved in TFA (50 mL) and triisopropylsilane (0.2 mL) was added. The obtained mixture was stirred for 24 h at room temperature then evaporated and the residue purified by chromatography on Amberlite XE 750 column (eluent: gradient of water/MeCN) obtaining compound 4 (12.4 g). Yield 90%.

1H-NMR, 13C-NMR and mass spectrum were consistent with the expected structure.

c) Preparation of 5

A solution of intermediate 4 (8.6 g; 5 mmol) in methanol (150 mL) was added with 5% palladium on carbon (wet with about 50% water) (2 g) and hydrogenated at room temperature for 24 h. The catalyst was filtered and the solution evaporated to give ligand 5 (6.6 g). Yield 96%.

1H-NMR, 13C-NMR and mass spectrum were consistent with the expected structure.

d) Complexation

Ligand 5 (5.46 g; 4 mmol) was dissolved in water (100 mL), gadolinium chloride hexahydrate (2.97 g; 8 mmol) was added, then 1M NaOH was added to achieve pH 7. The mixture was stirred at 50° C. for 18 h. The solution was then filtered on Millipore HA 0.25 μm filters and evaporated under reduced pressure. The crude product was purified on Amberchrome CG161M column (eluent: gradient of water/acetonitrile). The fractions containing the pure product were pooled and evaporated. The solid product was dried under vacuum to obtain the gadolinium complex as a white powder (6 g). Yield 90%.

Mass spectrum and elemental analysis were consistent with the expected structure.

Example 12: Preparation of the Chelate Complex 11
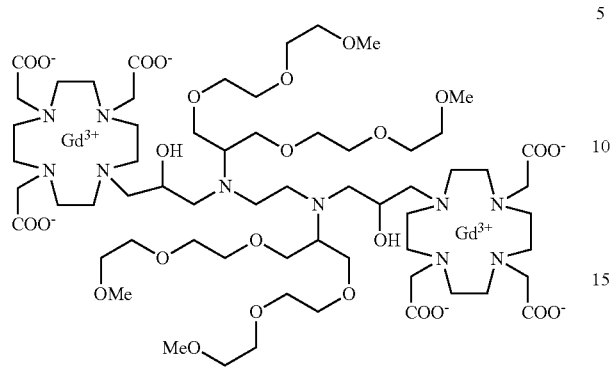
This compound was obtained by using the procedure shown in Scheme 15:
Scheme 15
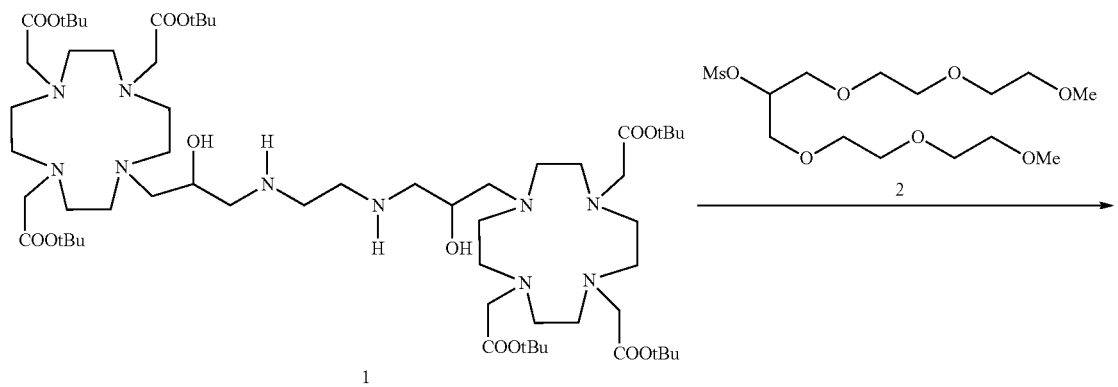
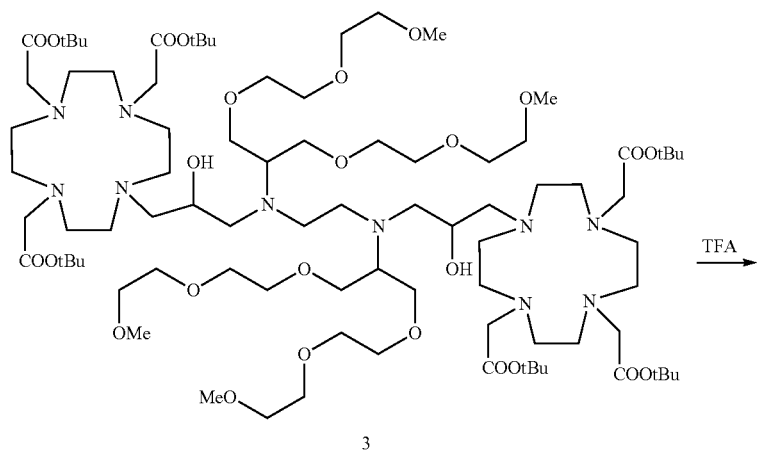

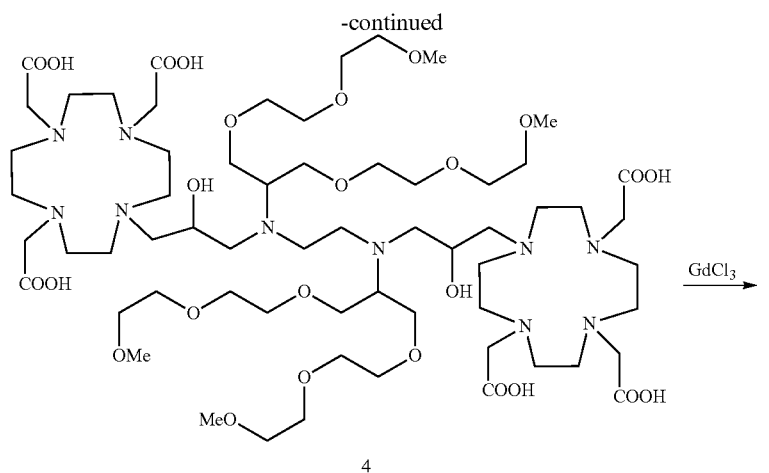

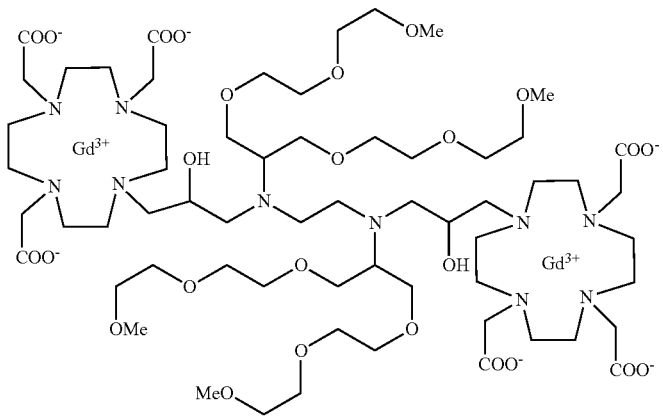

comprising:

a) Preparation of 3

Compound 2 (prepared as described in Example 7) (9.4 g, 25 mmol) was added to a solution of compound 1 (prepared as described in Example 9) (12 g; 10 mmol) in MeCN (150 mL) and the mixture was stirred for 72 h. The mixture was evaporated, the residue dissolved in CHCl$_3$ (200 mL) and washed with water (2×100 mL). The organic phase was separated, dried and evaporated. The residue was purified by flash chromatography on silica gel (eluent: CH$_2$Cl$_2$/MeOH=100:1→1:2) to give compound 3 (5.3 g). Yield 35%.

1H-NMR, 13C-NMR and mass spectrum were consistent with the expected structure.

b) Preparation of 4

Trifluoroacetic acid (15 mL) was added to a solution of intermediate 3 (14 g; 8 mmol) in dichloromethane (120 mL). The mixture stirred for 30 min then was evaporated. The residue was dissolved in TFA (50 mL) and triisopropylsilane (0.2 mL) was added. The obtained mixture was stirred for 24 h at room temperature then evaporated and the residue purified by chromatography on Amberlite XE 750 column (eluent: gradient of water/MeCN) obtaining ligand 4 (10.7 g). Yield 94%.

1H-NMR, 13C-NMR and mass spectrum were consistent with the expected structure.

c) Complexation

Ligand 4 (5.7 g; 4 mmol) was dissolved in water (100 mL), gadolinium chloride hexahydrate (2.97 g; 8 mmol) was added then 1M NaOH was added to achieve pH 7. The mixture was stirred at 50° C. for 18 h. The solution was then filtered on Millipore HA 0.25 µm filters and evaporated under reduced pressure. The crude product was purified on Amberchrome CG161M column (eluent: gradient of water/acetonitrile). The fractions containing the pure product were pooled and evaporated. The solid product was dried under vacuum to obtain the gadolinium complex as a white powder (6.4 g). Yield 92%.

Mass spectrum and elemental analysis were consistent with the expected structure.

Example 13: Preparation of the Chelate Complex 12

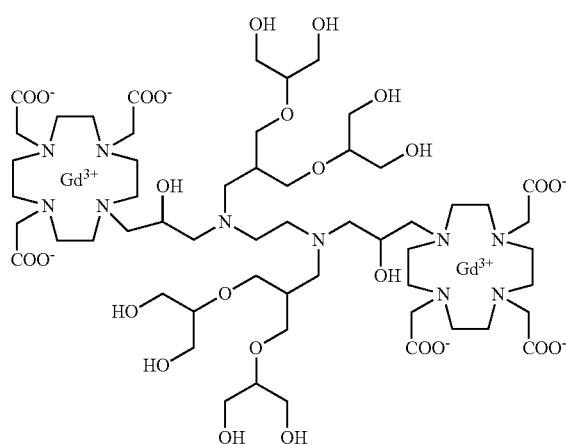

This compound was obtained by using the procedure shown in Scheme 16:
Scheme 16
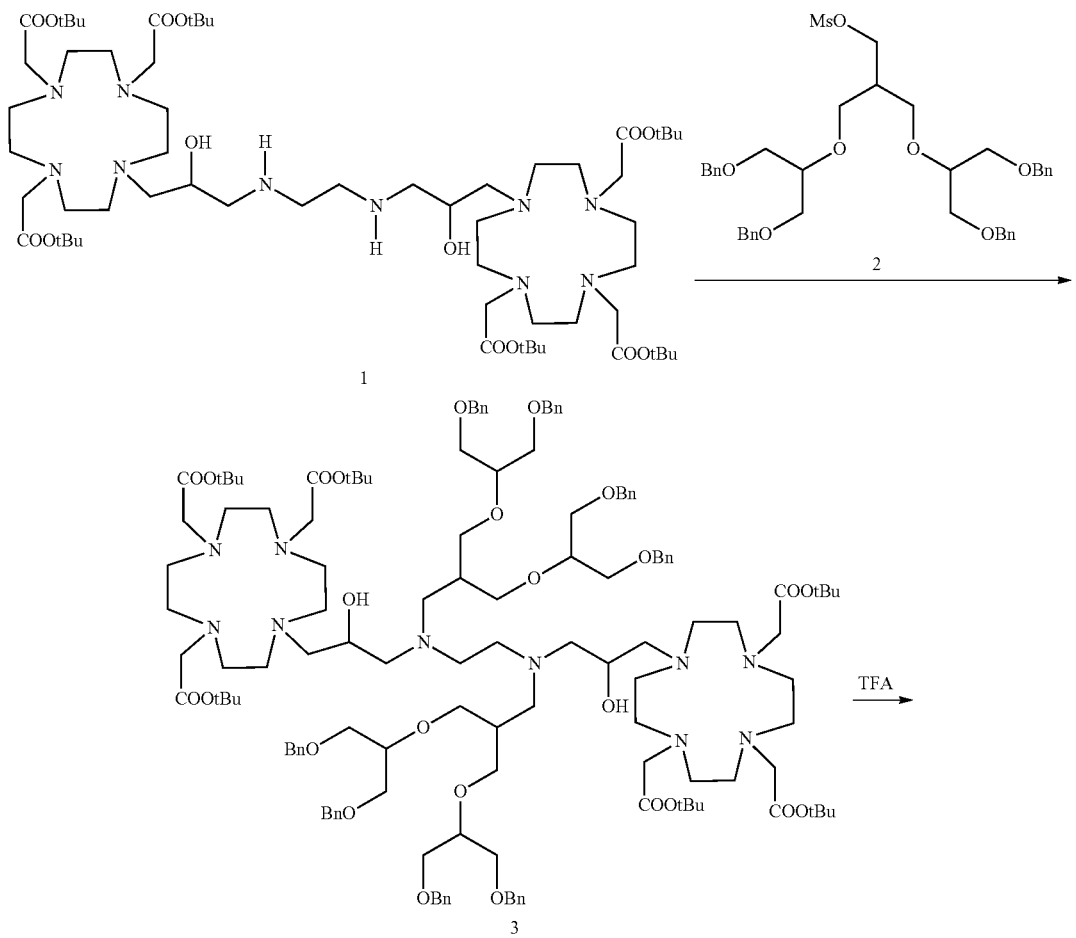
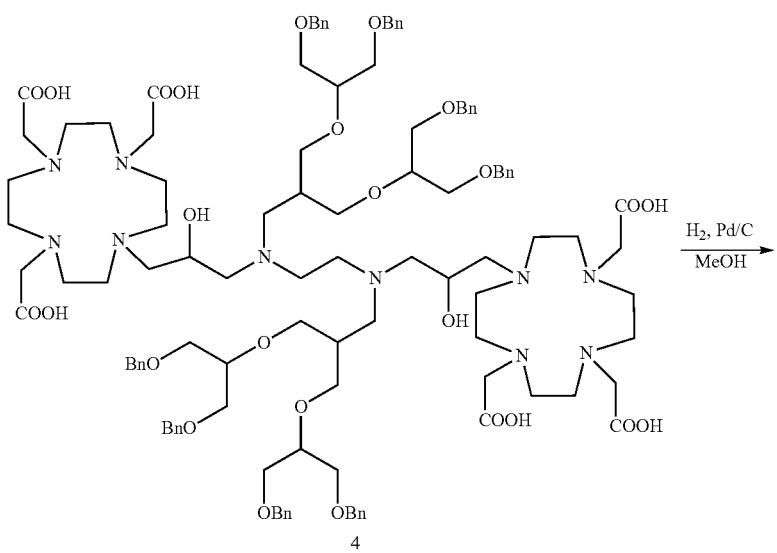

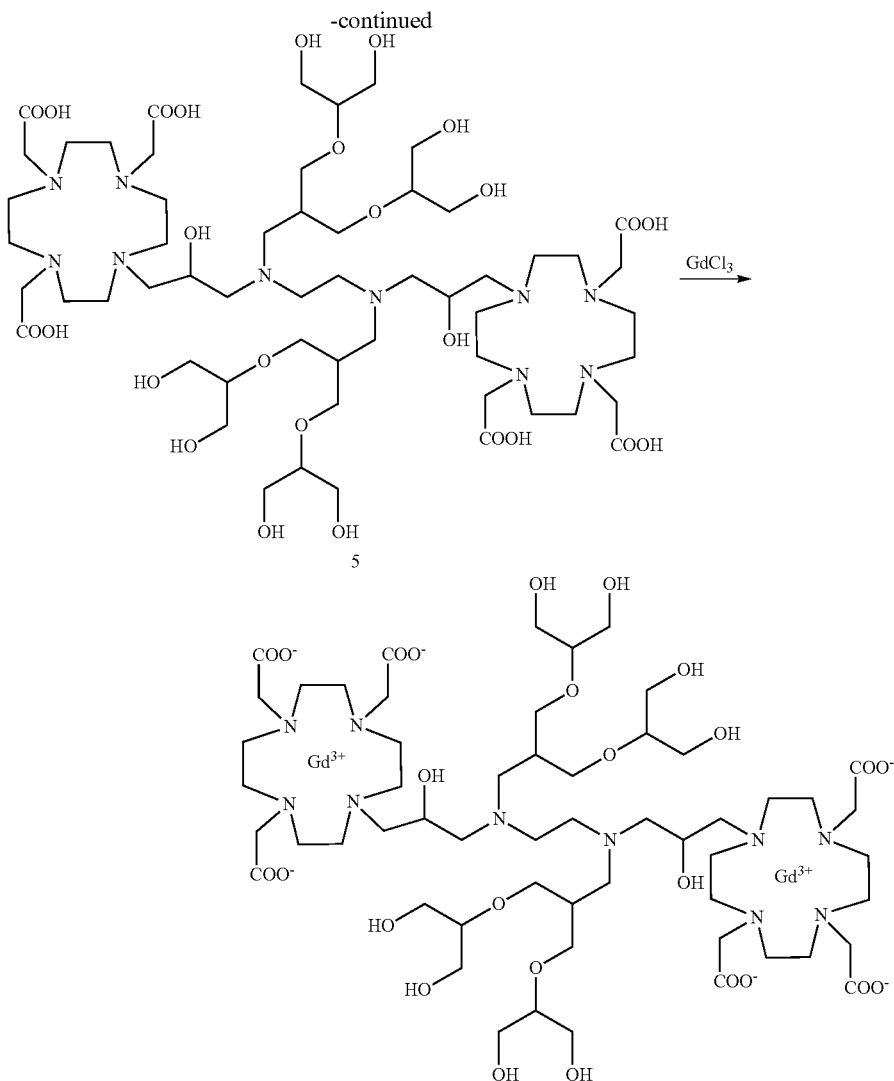

comprising:

a) Preparation of 3

Compound 2 (17.3 g, 25 mmol) was added to a solution of compound 1 (prepared as described in Example 9) (12 g; 10 mmol) in MeCN (200 mL) and the mixture was stirred for 96 h. The mixture was evaporated, the residue dissolved in CHCl$_3$ (300 mL) and washed with water (2×200 mL). The organic phase was separated, dried and evaporated. The residue was purified by flash chromatography on silica gel (eluent: CH$_2$Cl$_2$/MeOH=100:1→1:2) to give compound 3 (7.4 g). Yield 31%.

1H-NMR, 13C-NMR and mass spectrum were consistent with the expected structure.

b) Preparation of 4

Trifluoroacetic acid (20 mL) was added to a solution of intermediate 3 (24 g; 10 mmol) in dichloromethane (150 mL). The mixture stirred for 30 min then was evaporated. The residue was dissolved in TFA (70 mL) and triisopropylsilane (0.2 mL) was added. The obtained mixture was stirred for 24 h at room temperature then evaporated and the residue purified by chromatography on Amberlite XE 750 column (eluent: gradient of water/MeCN) obtaining compound 4 (18.1 g). Yield 88%.

1H-NMR, 13C-NMR and mass spectrum were consistent with the expected structure.

c) Preparation of 5

A solution of intermediate 4 (16.5 g; 8 mmol) in methanol (250 mL) was added with 5% palladium on carbon (wet with about 50% water) (3 g) and hydrogenated at room temperature for 24 h. The catalyst was filtered and the solution evaporated to give ligand 5 (10 g). Yield 93%.

1H-NMR, 13C-NMR and mass spectrum were consistent with the expected structure.

d) Complexation

Ligand 5 (5.35 g; 4 mmol) was dissolved in water (100 mL), gadolinium chloride hexahydrate (2.97 g; 8 mmol) was added, then 1M NaOH was added to achieve pH 7. The mixture was stirred at 50° C. for 18 h. The solution was then filtered on Millipore HA 0.25 μm filters and evaporated under reduced pressure. The crude product was purified on Amberchrome CG161M column (eluent: gradient of water/acetonitrile). The fractions containing the pure product were pooled and evaporated. The solid product was dried under vacuum to obtain the gadolinium complex as a white powder (6.2 g). Yield 94%.

Mass spectrum and elemental analysis were consistent with the expected structure.

Example 14: Preparation of the Chelate Complex 13
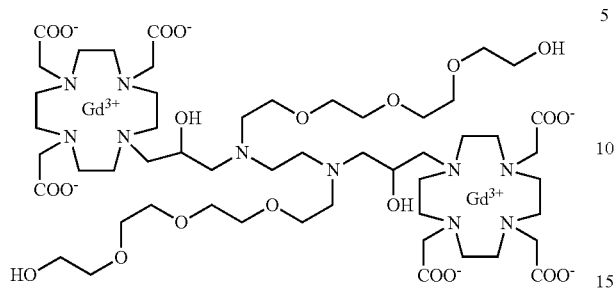
This compound was obtained by using the procedure shown in Scheme 17:
Scheme 17
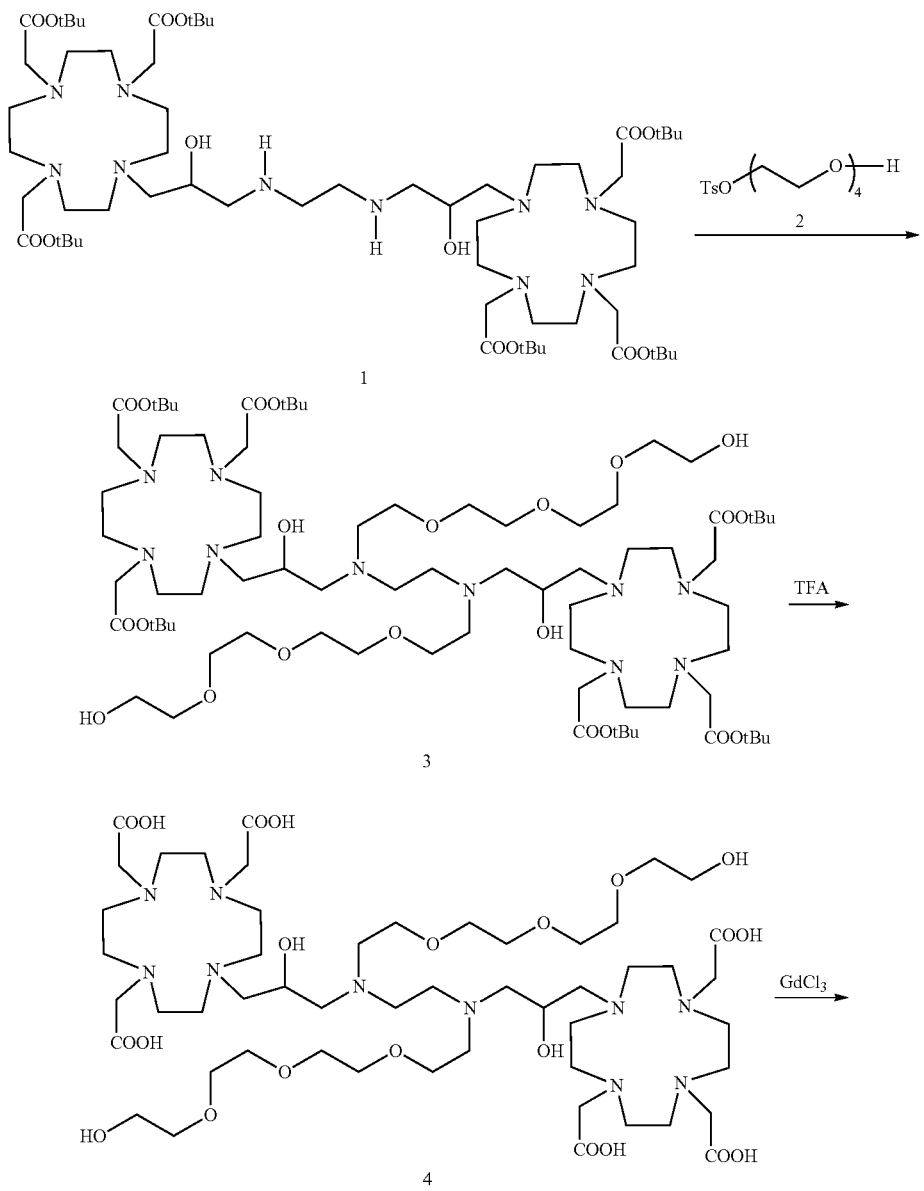

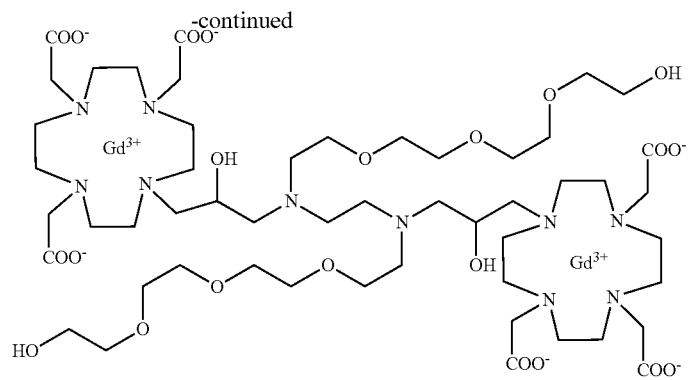
-continued comprising:

c) Preparation of 3

Tetraethylene glycol monotosylate 2 (commercial product, e.g. Aldrich) (5.2 g, 15 mmol) was added to a solution of compound 1 (prepared as reported in Example 9) (9 g; 7.5 mmol) in MeCN (100 mL) and the mixture was stirred at reflux for 72 h. The mixture was evaporated and the residue was purified by flash chromatography on silica gel (eluent: $CH_2Cl_2$/MeOH=100:1→1:1) to give compound 3 (4.8 g). Yield 41%.

1H-NMR, 13C-NMR and mass spectrum were consistent with the expected structure.

d) Preparation of 4

Trifluoroacetic acid (10 mL) was added to a solution of intermediate 3 (7.8 g; 5 mmol) in dichloromethane (60 mL). The mixture stirred for 30 min then was evaporated. The residue was dissolved in TFA (50 mL) and triisopropylsilane (0.1 mL) was added. The obtained mixture was stirred for 24 h at room temperature then evaporated and the residue purified by chromatography on Amberlite XE 750 column (eluent: gradient of water/MeCN) obtaining ligand 4 (5.6 g). Yield 92%.

1H-NMR, 13C-NMR and mass spectrum were consistent with the expected structure.

e) Complexation

Ligand 4 (4.9 g; 4 mmol) was dissolved in water (100 mL), gadolinium chloride hexahydrate (2.97 g; 8 mmol) was added then 1M NaOH was added to achieve pH 7. The mixture was stirred at 50° C. for 18 h. The solution was then filtered on Millipore HA 0.25 μm filters and evaporated under reduced pressure. The crude product was purified on Amberchrome CG161M column (eluent: gradient of water/acetonitrile). The fractions containing the pure product were pooled and evaporated. The solid product was dried under vacuum to obtain the gadolinium complex as a white powder (5.19 g). Yield 85%.

Mass spectrum and elemental analysis were consistent with the expected structure.

Example 15: Relaxometric Properties

The relaxometric properties of some representative complex compounds according to the invention have been determined at different magnetic field strengths, e.g. including 0.47 and 1.41 T, at 37° C., in human plasma and compared with relaxivity values measured, at the same conditions, for some Gd-complex of the market having an analogous cyclic coordination cage.

Materials

Apparatus

The longitudinal water proton relaxation rate ($R_1=1/T_1$) was measured at 0.47 T with a Minispec MQ-20 spectrometer (Bruker Biospin, Germany) operating at a proton Larmor frequency of 20 MHz; MR experiments at 1.41 T were performed using a Minispec MQ-60 spectrometer (Bruker Biospin, Germany) operating at a proton Larmor frequency of 60 MHz.

Methods

Sample Preparation

All test articles were used as supplied and diluted in the selected medium (human plasma) by weighting the required amount of paramagnetic chelated complex to get a starting solution of 5 or 10 mM concentration in gadolinium.

Relaxivity Measurements Five different concentration samples (0.1, 0.25, 0.5, 0.75 and 1 mM in gadolinium) for each medium have been prepared by further dilution of the starting 5 or 10 mM solution.

Relaxation Measurement

Relaxivity measurements were performed at 0.47 T and 1.41 T at a preset temperature sample of 37° C., kept constant by means of a thermostatic bath connected to the sample holder of the spectrometer. The five sample solutions have been preliminary pre-heated at 37° C. in an external thermostatic bath and then left 10 minutes inside the internal bath to assure the stabilization of the temperature. Longitudinal relaxation time $T_1$ was measured by means of a standard inversion recovery sequence, where the inversion time (TI) was varied from 10 ms to at least 5 times $T_1$ in 15 steps. Statistical analysis (mono-exponential fitting for $T_1$ measurement, linear fitting for the evaluation of longitudinal relaxivity) was performed by Mathematica® (Wolfram, USA). Errors on the estimated parameters were evaluated by the fitting procedure.

Results

The relaxivity values $r_{1p}$ of some representative compounds according to the invention, obtained in human plasma at 37° C., are summarized in the following Table A, together with the structure of tested compounds and the strength of the applied magnetic field (in T), and compared with corresponding values measured for two commercial contrast agents in clinical practice having a macrocyclic chelating cage.

By definition, relaxivity data, and hence including those of the table below, are expressed in terms of gadolinium concentration.

TABLE A

| Complex | $r_{1p}$ at 0.47 T 37° C., human plasma | $r_{1p}$ at 1.41 T 37° C., human plasma |
|---|---|---|
| Doratem® | 4.5 | 3.6 |
| ProHance® | 4.9 | 4.15 |
| Chelate complex 1 | 10.9 | 10.4 |
| Chelate Complex 2 | 12.1 | 11.8 |

TABLE A-continued

| Complex | $r_{1p}$ at 0.47 T 37° C., human plasma | $r_{1p}$ at 1.41 T 37° C., human plasma |
|---|---|---|
| 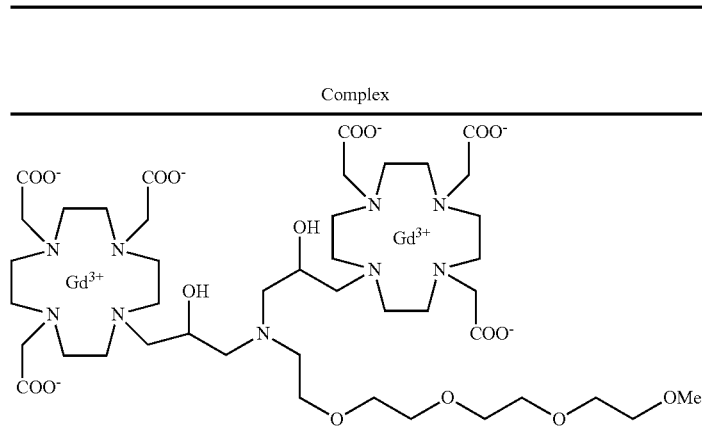 Chelate Complex 4 | 10.6 | 10.3 |
| 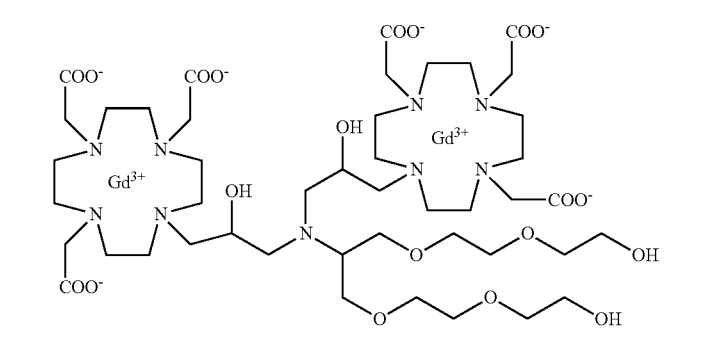 Chelate Complex 5 | 10.1 | 9.8 |
| 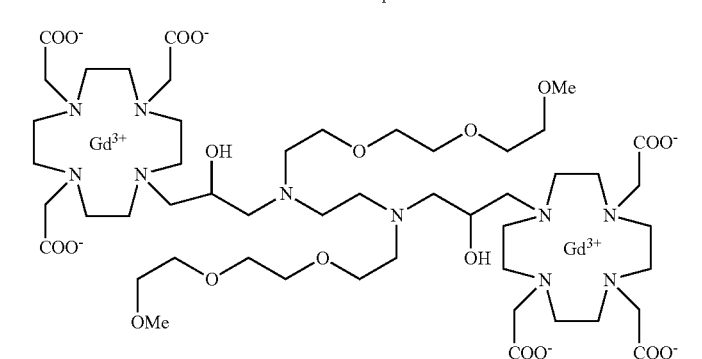 Chelate Complex 9 | 12.1 | 11.5 |

CONCLUSIONS

The relaxivity of the investigated contrast agents ranges between 4.9 (for ProHance) and 12.1 mM$^{-1}$ s$^{-1}$ (for chelate complex 2 and chelate complex 9) at 0.47 T, in plasma, at the same mM Gd$^{3+}$ concentration. These results confirm that the particular selection represented by the paramagnetic complexes and, especially, the Gd$^{3+}$ complexes of the compounds of formula (I) of the invention show an increased relaxivity $r_{1p}$, which is at least about 2 times the relaxivity shown, at the same conditions (i.e. in human plasma, at 37° C.), by the Non Specific contrast agents currently in use in the daily diagnostic practice, such as Dotarem® and ProHance®.

The invention claimed is:
1. A compound of formula (I)

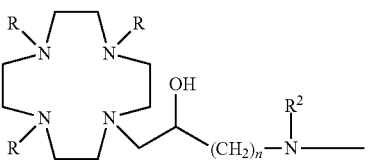
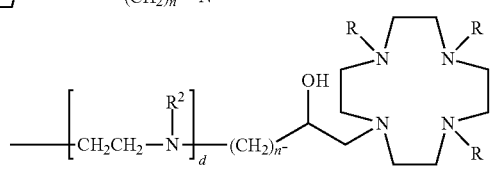

where:

R is —CH(R$^1$)—COOH, where:
 R$^1$ is H or a C$_1$-C$_3$ alkyl chain that is optionally substituted by a C$_1$-C$_3$ alkoxy or C$_1$-C$_3$ hydroxyalkoxy group;

n is 1 or 2;

d is 0 or 1;

R$^2$ is a C$_1$-C$_5$ alkyl substituted by from 1 to 3 groups X where:
 X is a group of formula —O—[CH(CH$_2$O—)$_2$]$_s$(R$^3$)$_{s+1}$ or —O—(CH$_2$CH$_2$O—)$_r$—R$^3$,
 in which:

R$^3$ is H or a C$_1$-C$_3$ alkyl group, bound to the respective oxygen atom(s) of terminal units —CH(CH$_2$O—) or —(CH$_2$CH$_2$O—) of X;

r is 1, 2, 3, 4, 5, 6, 7 or 8; and s is 1, 2 or 3;

with the proviso that when the C$_1$-C$_5$ alkyl in R$^2$ is substituted by a single group X, r and s are not 1, as well as individual diastereoisomers and their racemic mixtures, and solved enantiomers of the same, and the physiologically acceptable salts thereof.

2. The compound according to claim 1 in which R$^1$ is H.

3. The compound according to claim 1 in which, in the formula (I) d is 0, having the formula (II)

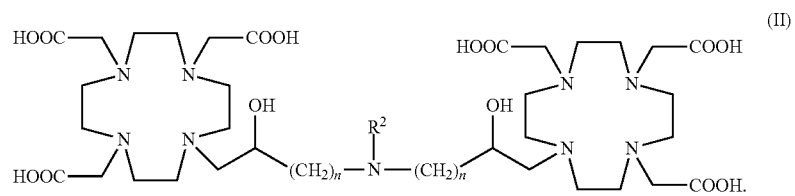

(II)

4. The compound according to claim 3 in which, in the formula (II), R$^2$ is a C$_1$-C$_5$ alkyl substituted by a single group X, having the formula

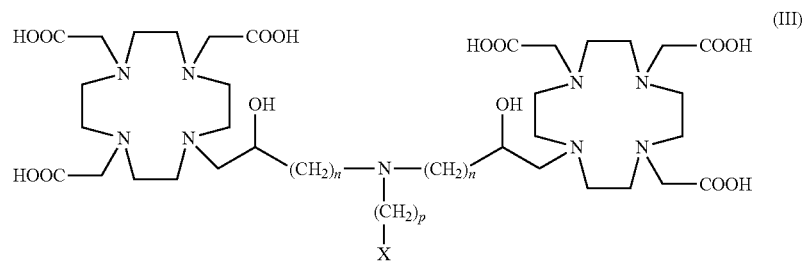

(III)

in which:
p is 1, 2, 3, 4, or 5; and
X is as defined in claim 1.

5. The compound according to claim 4 where X is a group of formula —O—(CH$_2$CH$_2$O—)$_r$R$^3$, having the following formula (III A)

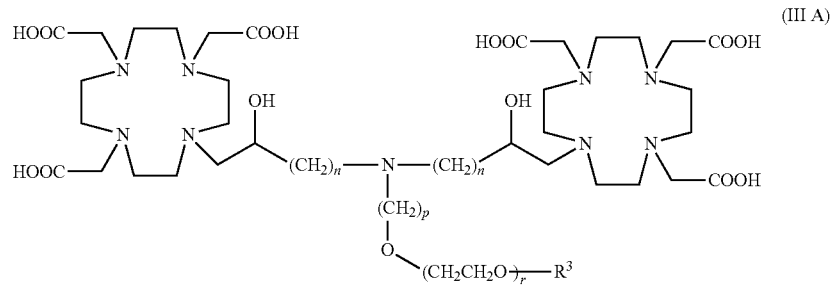

(III A)

in which:
p is 1, 2, or 3;
r is an integer from 2 to 8; and
$R^3$ is H, or a $C_1$-$C_3$ alkyl selected from methyl and ethyl.

6. The compound according to claim 5 in which, in the formula (III A)
p is 2;
r is from 2 to 5; and
$R^3$ is H, or methyl.

7. The compound according to claim 4 where X is a group of formula —O—[CH(CH$_2$O—)$_2$]$_s$(R$^3$)$_{s+1}$, having the following formula (III B)

(III B)

in which:
p is 1, 2, or 3;
s is 2 or 3; and
$R^3$ is H, or a $C_1$-$C_3$ alkyl selected from methyl and ethyl.

8. The compound according to claim 3 in which, in the formula (II), $R^2$ is a $C_1$-$C_5$ alkyl substituted by two groups X, selected from the group consisting of

—CH$_2$CH$_2$CHCH$_2$—X,    —CH$_2$CH(CH$_2$X)$_2$,
       |
       X

—CH(CH$_2$X)$_2$    and    —CH$_2$CHCH$_2$—X,
                                  |
                                  X or a $C_1$-$C_5$ alkyl substituted by three groups X, selected from —CH$_2$CHCHCH$_2$—X    and    —C(CH$_2$X)$_3$
      |    |
      X    X where X is defined in claim 1.

9. The compound according to claim 8, having the formula (IV)

(IV)

the formula (V)

(V)

the formula (VI)

(VI)

in which n and X are as defined in claim 1.

10. The compound according to claim 9, having the formula (IV A)

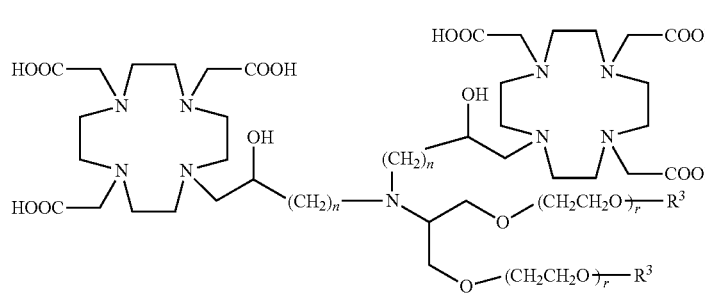

(IV A)

or the formula (V A)

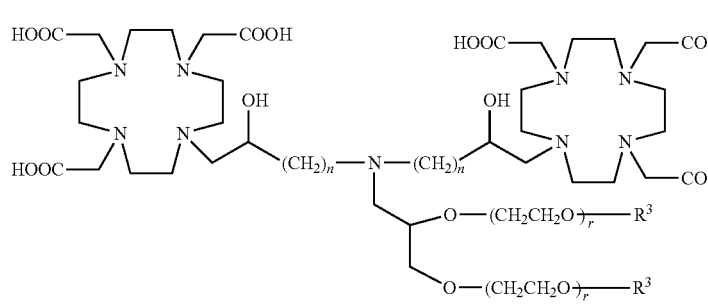

(V A)

in which:
r is an integer from 1 to 8;
n is 1 or 2, and
$R^3$ is H or a $C_1$-$C_3$ alkyl selected from methyl and ethyl.

11. The compound according to claim 9, having the formula (IV B)

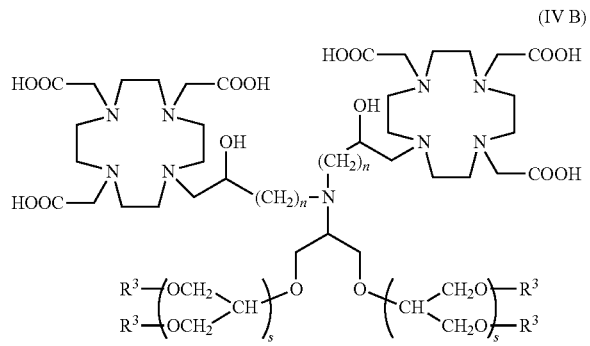

(IV B)

or the formula (VI B)

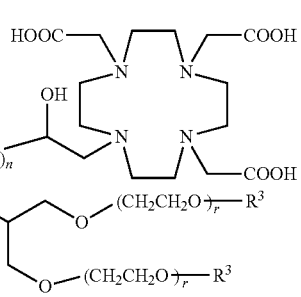

(VI B)

in which:
s is 1 or 2, and
$R^3$ is H or a $C_1$-$C_3$ alkyl selected from methyl and ethyl.

12. The compound according to claim 1 in which, in the formula (I) d is 1, having the formula (VII)

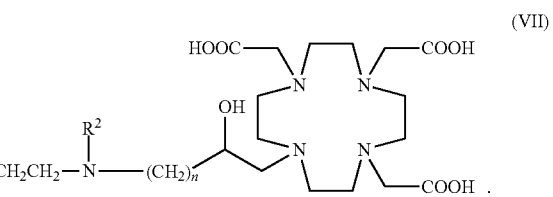

(VII)

13. The compound according to claim 12 having the formula (VIII)

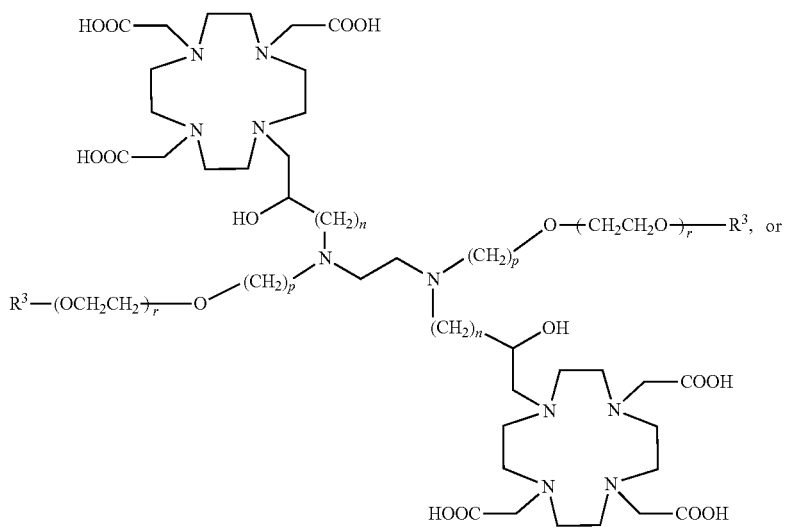

(VIII)

the formula (IX)

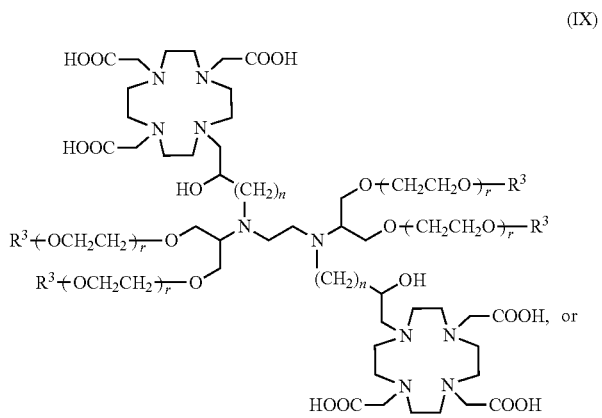

(IX)

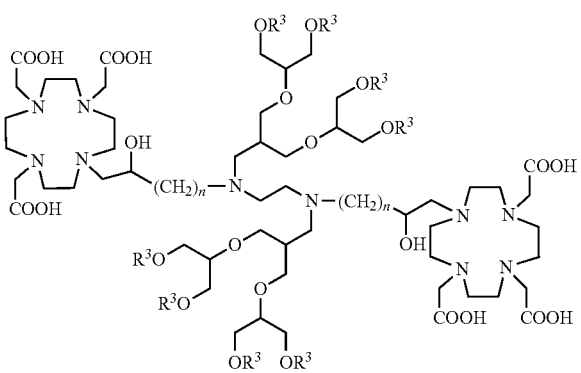

(X)

the formula (X)

in which
p is 1, 2 or 3;
r is an integer from 1 to 8;
n is 1 or 2, and
$R^3$ is H or a $C_1$-$C_3$ alkyl selected from ethyl and methyl.

14. The compound according to claim 1 in which in the formula (I) n is 1 and $R^3$ is H.

15. The compound according to claim 1 in which in the formula (I) n is 1 and $R^3$ is methyl.

16. A chelated complex of a compound according to claim 1 with two paramagnetic metal ions selected from the group consisting of $Fe^{2+}$, $Fe^{3+}$, $Cu^{2+}$, $Cr^{3+}$, $Gd^{3+}$, $Eu^{3+}$, $Dy^{3+}$, $La^{3+}$, $Yb^{3+}$ and $Mn^{2+}$, or a physiologically acceptable salt thereof.

17. The chelated complex according to claim 16, wherein the paramagnetic metal ions are $Gd^{3+}$ ions.

18. The chelated complex according to claim 16 with bivalent metal ion(s), wherein the physiologically acceptable salt is with a cation of (i) an inorganic base selected from an alkali metal and alkaline-earth metal, (ii) an organic base selected from ethanolamine, diethanolamine, morpholine, glucamine, N-methylglucamine, and N,N-dimethylglucamine or (iii) an amino acid selected from lysine, arginine and ornithine.

19. A method of MR imaging comprising:
   administering the chelated complex as defined in claim 16 to a patient;
   submitting the patient to a radiation frequency selected to excite non-zero proton spin nuclei of the chelated complex; and
   recording a MR signal from said nuclei.

20. A pharmaceutical composition comprising a chelated complex of claim 16 in combination with one or more pharmaceutically acceptable carriers, diluents or excipients.

21. The compound according to claim 1 of formula:
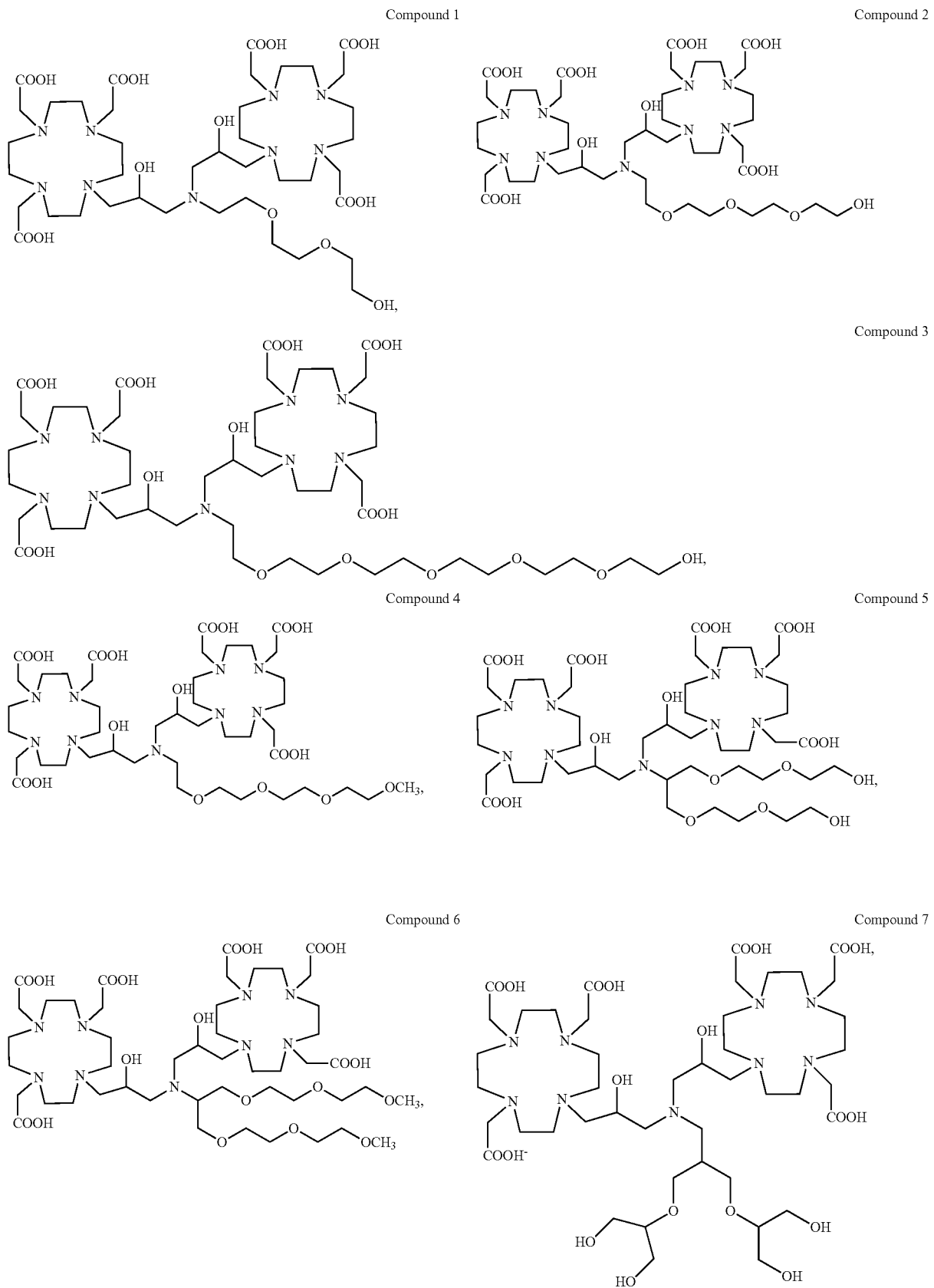

Compound 8
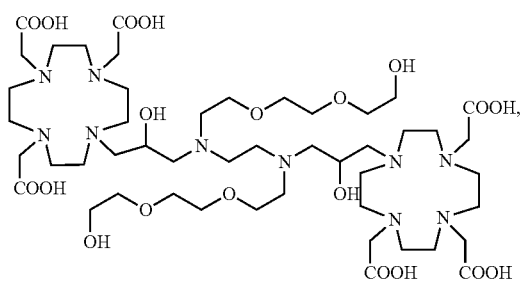
Compound 9
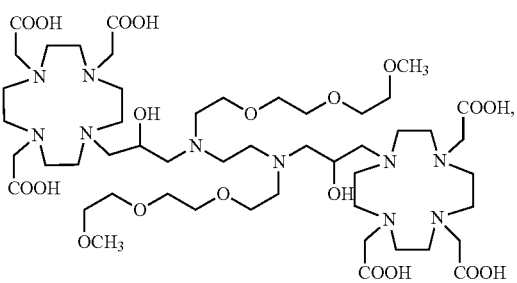
Compound 10
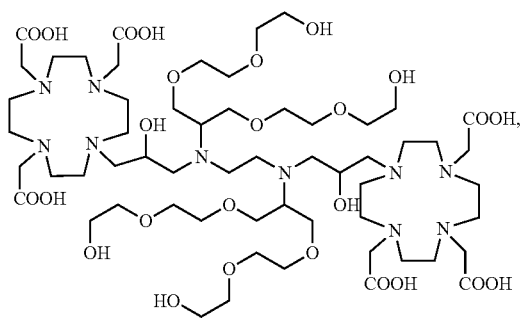
Compound 11
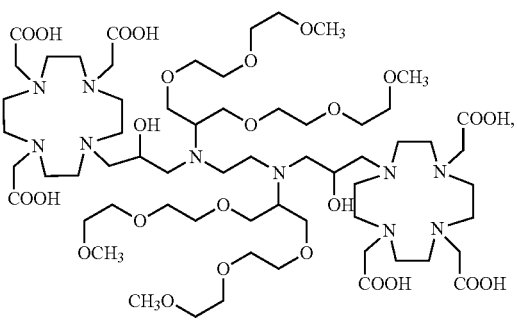
Compound 12
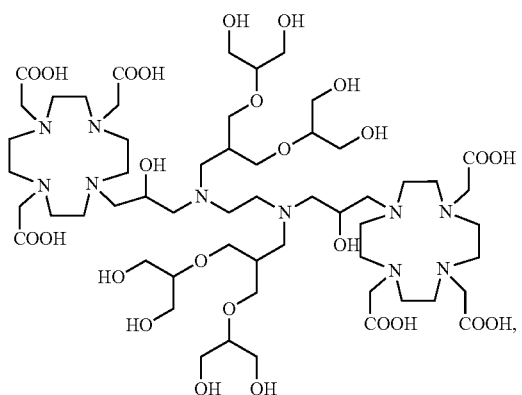
Compound 13
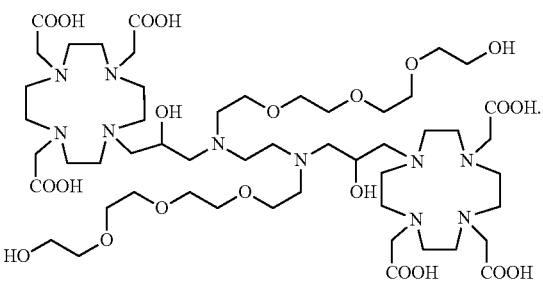
or
22. A compound of formula (1)
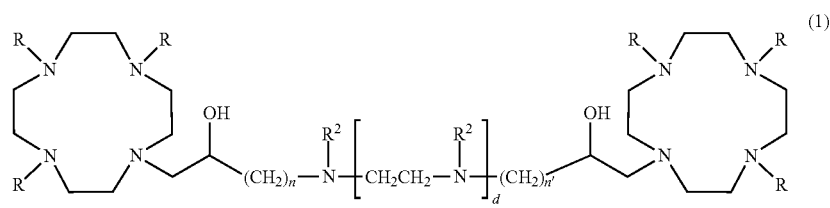

where:

R is $CH(R^1)$—$COOC(CH_3)_3$, where:
  $R^1$ is H or a $C_1$-$C_3$ alkyl chain that is optionally substituted by a $C_1$-$C_{03}$ alkoxy or a $C_1$-$C_3$ hydroxyalkoxy group;

n is 1 or 2;

d is 0 or 1;

$R^2$ is a $C_1$-$C_5$ alkyl substituted by from 1 to 3 groups X where:
  X is a group of formula —O—$[CH(CH_2O—)_2]_s(R^3)_{s+1}$ or —O—$(CH_2CH_2O—)_rR^3$,
  in which:
  $R^3$ is H or a $C_1$-$C_3$ alkyl group, bound to the respective oxygen atom(s) of terminal units —$(CH(CH_2O—)$ or —$(CH_2CH_2O—)$ of X;
  r is 1, 2, 3, 4, 5, 6, 7 or 8; and
  s is 1, 2, or 3;

with the proviso that when the $C_1$-$C_5$ alkyl in $R^2$ is substituted by a single group X, r and s are not 1.

\* \* \* \* \*

UNITED STATES PATENT AND TRADEMARK OFFICE
CERTIFICATE OF CORRECTION

PATENT NO. : 10,793,533 B2
APPLICATION NO. : 16/468035
DATED : October 6, 2020
INVENTOR(S) : Valeria Boi et al.

Page 1 of 2

It is certified that error appears in the above-identified patent and that said Letters Patent is hereby corrected as shown below:

In the Specification

Column 11, the structure of formula (VI B) should read

"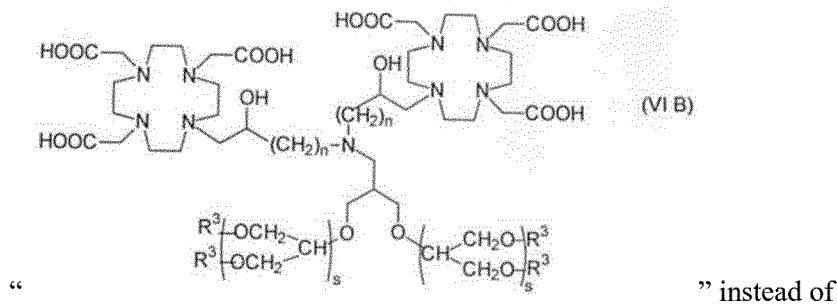" instead of

"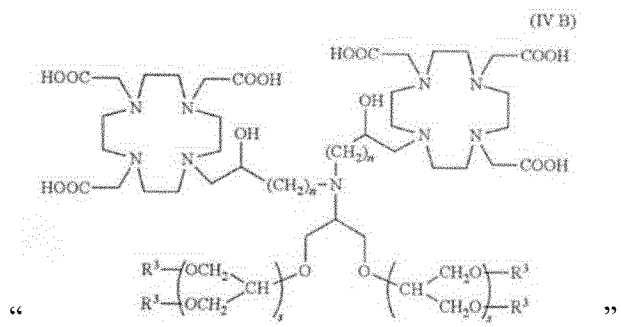"

In the Claims

Claim 11, Column 88, the structure of formula (VI B) should read

Signed and Sealed this
Fifth Day of January, 2021

Andrei Iancu
*Director of the United States Patent and Trademark Office*

CERTIFICATE OF CORRECTION (continued)
U.S. Pat. No. 10,793,533 B2

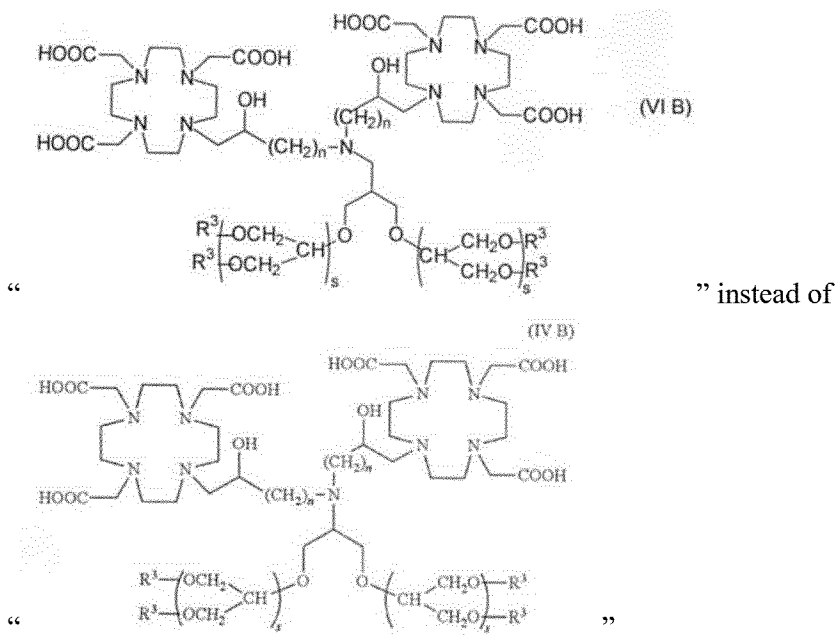

Claim 22, Column 95, Line 4 should read "a $C_1$-$C_3$ alkoxy" instead of "a $C_1$-$C_{03}$ alkoxy"

Claim 22, Column 95, Line 14 should read "units -CH(CH$_2$O-)" instead of "units –(CH(CH$_2$O-)"